United States Patent
Desai

(10) Patent No.: US 10,413,531 B2
(45) Date of Patent: *Sep. 17, 2019

(54) METHODS OF TREATING BLADDER CANCER

(71) Applicant: Abraxis BioScience, LLC, Summit, NJ (US)

(72) Inventor: Neil P. Desai, Pacific Palisades, CA (US)

(73) Assignee: Abraxis BioScience, LLC, Summit, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 15/938,952

(22) Filed: Mar. 28, 2018

(65) Prior Publication Data

US 2018/0214425 A1 Aug. 2, 2018

Related U.S. Application Data

(63) Continuation of application No. 14/772,725, filed as application No. PCT/US2014/026564 on Mar. 13, 2014, now Pat. No. 9,962,373.

(60) Provisional application No. 61/786,167, filed on Mar. 14, 2013, provisional application No. 61/786,175, filed on Mar. 14, 2013.

(51) Int. Cl.
| | |
|---|---|
| *A61K 9/00* | (2006.01) |
| *A61K 31/00* | (2006.01) |
| *A61K 45/00* | (2006.01) |
| *A61K 31/436* | (2006.01) |
| *A61K 39/04* | (2006.01) |
| *A61K 45/06* | (2006.01) |
| *A61K 9/51* | (2006.01) |
| *A61K 39/00* | (2006.01) |

(52) U.S. Cl.
CPC .......... *A61K 31/436* (2013.01); *A61K 9/0019* (2013.01); *A61K 9/0034* (2013.01); *A61K 9/5169* (2013.01); *A61K 39/04* (2013.01); *A61K 45/06* (2013.01); *A61K 2039/585* (2013.01)

(58) Field of Classification Search
CPC .............. A61K 31/436; A61K 2300/00; A61K 2039/585; A61K 39/04; A61K 45/06; A61K 9/0019; A61K 9/0034; A61K 9/5169

See application file for complete search history.

(56) References Cited

U.S. PATENT DOCUMENTS

| | | | |
|---|---|---|---|
| 5,362,478 A | 11/1994 | Desai et al. | |
| 5,439,686 A | 8/1995 | Desai et al. | |
| 5,498,421 A | 3/1996 | Grinstaff et al. | |
| 5,505,932 A | 4/1996 | Grinstaff et al. | |
| 5,508,021 A | 4/1996 | Grinstaff et al. | |
| 5,512,268 A | 4/1996 | Grinstaff et al. | |
| 5,560,933 A | 10/1996 | Soon-Shiong et al. | |
| 5,635,207 A | 6/1997 | Grinstaff et al. | |
| 5,639,473 A | 6/1997 | Grinstaff et al. | |
| 5,650,156 A | 7/1997 | Grinstaff et al. | |
| 5,665,382 A | 9/1997 | Grinstaff et al. | |
| 5,665,383 A | 9/1997 | Grinstaff et al. | |
| 5,916,596 A | 6/1999 | Desai et al. | |
| 5,997,904 A | 12/1999 | Magdassi et al. | |
| 6,096,331 A | 8/2000 | Desai et al. | |
| 6,506,405 B1 | 1/2003 | Desai et al. | |
| 6,528,067 B1 | 3/2003 | Magdassi et al. | |
| 6,537,579 B1 | 3/2003 | Desai et al. | |
| 6,565,842 B1 | 5/2003 | Desai et al. | |
| 6,652,884 B2 | 11/2003 | Falciani | |
| 6,749,868 B1 | 6/2004 | Desai et al. | |
| 6,753,006 B1 | 6/2004 | Desai et al. | |
| 7,758,891 B2 | 7/2010 | Desai et al. | |
| 7,771,751 B2 | 10/2010 | Desai et al. | |
| 7,820,788 B2 | 10/2010 | Desai et al. | |
| 7,923,536 B2 | 4/2011 | Desai et al. | |
| 7,981,445 B2 | 7/2011 | De et al. | |
| 8,034,375 B2 | 10/2011 | Desai et al. | |
| 8,034,765 B2 | 10/2011 | De et al. | |
| 8,137,684 B2 | 3/2012 | Desai et al. | |
| 8,138,229 B2 | 3/2012 | Desai et al. | |
| 8,257,733 B2 | 9/2012 | Desai et al. | |
| 8,268,348 B2 | 9/2012 | Desai et al. | |
| 8,314,156 B2 | 11/2012 | Desai et al. | |
| 8,585,753 B2 | 11/2013 | Scanolon | |
| 8,735,394 B2 | 5/2014 | Desai et al. | |
| 8,846,771 B2 | 9/2014 | Desai et al. | |
| 8,853,260 B2 | 10/2014 | Desai et al. | |
| 8,911,786 B2 | 12/2014 | Desai et al. | |
| 8,927,019 B2 | 1/2015 | Desai et al. | |

(Continued)

FOREIGN PATENT DOCUMENTS

| | | |
|---|---|---|
| AU | 2013204187 A1 | 5/2013 |
| EP | 2 359 859 A1 | 8/2011 |

(Continued)

OTHER PUBLICATIONS

Askeland, E.J. et al. (2012). "Bladder Cancer Immunotherapy: BCG and Beyond," *Advances in Urology*, 2012: Article ID 181987, 14 pages.

(Continued)

*Primary Examiner* — Robert A Wax
*Assistant Examiner* — Olga V. Tcherkasskaya
(74) *Attorney, Agent, or Firm* — Morrison & Foerster LLP

(57) ABSTRACT

The present invention provides methods and compositions for treating bladder cancer, including metastatic bladder cancer and non-muscle-invasive bladder cancer, by administering a composition comprising nanoparticles that comprise mTOR inhibitor and optionally an albumin.

19 Claims, No Drawings

(56) References Cited

U.S. PATENT DOCUMENTS

| | | |
|---|---|---|
| 8,999,396 B2 | 4/2015 | Desai et al. |
| 9,012,518 B2 | 4/2015 | Desai et al. |
| 9,012,519 B2 | 4/2015 | Desai et al. |
| 9,061,014 B2 | 6/2015 | Seward et al. |
| 9,101,543 B2 | 8/2015 | Desai et al. |
| 9,149,455 B2 | 10/2015 | Desai et al. |
| 9,308,180 B2 | 4/2016 | De et al. |
| 9,370,494 B2 | 6/2016 | Yeo et al. |
| 9,393,318 B2 | 7/2016 | Desai et al. |
| 9,399,071 B2 | 7/2016 | Desai et al. |
| 9,399,072 B2 | 7/2016 | Desai et al. |
| 9,446,003 B2 | 9/2016 | Desai et al. |
| 9,511,046 B2 | 12/2016 | Desai et al. |
| 9,561,288 B2 | 2/2017 | Desai et al. |
| 9,585,960 B2 | 3/2017 | Foss et al. |
| 9,597,409 B2 | 3/2017 | Desai et al. |
| 9,675,578 B2 | 6/2017 | Desai et al. |
| 9,724,323 B2 | 8/2017 | Desai et al. |
| 9,820,949 B2 | 11/2017 | Desai et al. |
| 9,855,220 B2 | 1/2018 | Desai et al. |
| 9,884,013 B2 | 2/2018 | Seward et al. |
| 9,962,373 B2 | 5/2018 | Desai |
| 10,076,501 B2 | 9/2018 | Foss et al. |
| 2003/0185894 A1 | 10/2003 | Zenoni et al. |
| 2003/0187062 A1 | 10/2003 | Zenoni et al. |
| 2003/0199425 A1 | 10/2003 | Desai et al. |
| 2005/0004002 A1 | 1/2005 | Desai et al. |
| 2006/0263434 A1 | 11/2006 | Desai et al. |
| 2007/0082838 A1 | 4/2007 | De et al. |
| 2008/0280987 A1 | 11/2008 | Desai et al. |
| 2009/0263483 A1 | 10/2009 | Desai et al. |
| 2010/0048499 A1 | 2/2010 | Desai et al. |
| 2010/0143340 A1 | 6/2010 | Kolhe et al. |
| 2010/0166869 A1 | 7/2010 | Desai et al. |
| 2010/0183728 A1 | 7/2010 | Desai |
| 2010/0297243 A1 | 11/2010 | Desai et al. |
| 2011/0014117 A1 | 1/2011 | Wang et al. |
| 2011/0052708 A1 | 3/2011 | Soon-Shiong et al. |
| 2011/0118342 A1 | 5/2011 | De et al. |
| 2011/0129456 A1 | 6/2011 | Wang |
| 2011/0151012 A1 | 6/2011 | Desai et al. |
| 2012/0064124 A1 | 3/2012 | McClain |
| 2012/0070502 A1 | 3/2012 | Desai et al. |
| 2012/0076862 A1 | 3/2012 | Desai et al. |
| 2012/0128732 A1 | 5/2012 | Trieu et al. |
| 2012/0189701 A1 | 7/2012 | Desai et al. |
| 2012/0231082 A1 | 9/2012 | Desai et al. |
| 2012/0283205 A1 | 11/2012 | Desai et al. |
| 2012/0308612 A1 | 12/2012 | De et al. |
| 2013/0045240 A1 | 2/2013 | Tao et al. |
| 2013/0071438 A1 | 3/2013 | Desai et al. |
| 2013/0115296 A1 | 5/2013 | Yeo et al. |
| 2013/0195922 A1 | 8/2013 | Desai et al. |
| 2013/0195983 A1 | 8/2013 | Desai et al. |
| 2013/0195984 A1 | 8/2013 | Desai et al. |
| 2013/0202709 A1 | 8/2013 | Desai et al. |
| 2013/0209518 A1 | 8/2013 | Desai et al. |
| 2013/0244952 A1 | 9/2013 | Desai et al. |
| 2013/0266659 A1 | 10/2013 | Desai et al. |
| 2013/0280336 A1 | 10/2013 | Desai et al. |
| 2013/0280337 A1 | 10/2013 | Desai et al. |
| 2014/0017315 A1 | 1/2014 | Desai et al. |
| 2014/0017316 A1 | 1/2014 | Desai et al. |
| 2014/0017323 A1 | 1/2014 | Desai et al. |
| 2014/0023717 A1 | 1/2014 | Desai et al. |
| 2014/0039069 A1 | 2/2014 | Desai et al. |
| 2014/0039070 A1 | 2/2014 | Desai et al. |
| 2014/0056986 A1 | 2/2014 | Desai et al. |
| 2014/0072630 A1 | 3/2014 | Tao et al. |
| 2014/0072631 A1 | 3/2014 | Trieu et al. |
| 2014/0072643 A1 | 3/2014 | Desai et al. |
| 2014/0079774 A1 | 3/2014 | Brinker |
| 2014/0079787 A1 | 3/2014 | Yeo et al. |
| 2014/0079788 A1 | 3/2014 | Desai et al. |
| 2014/0079793 A1 | 3/2014 | Desai et al. |
| 2014/0080901 A1 | 3/2014 | Desai et al. |
| 2014/0134257 A1 | 5/2014 | Desai et al. |
| 2014/0155344 A1 | 6/2014 | Desai et al. |
| 2014/0170228 A1 | 6/2014 | Desai et al. |
| 2014/0186447 A1 | 7/2014 | Desai |
| 2014/0199403 A1 | 7/2014 | Desai et al. |
| 2014/0199404 A1 | 7/2014 | Heise et al. |
| 2014/0199405 A1 | 7/2014 | Pierce et al. |
| 2014/0271871 A1 | 9/2014 | Desai et al. |
| 2014/0296279 A1 | 10/2014 | Seward et al. |
| 2014/0296353 A1 | 10/2014 | Desai et al. |
| 2014/0302157 A1 | 10/2014 | Desai et al. |
| 2015/0050356 A1 | 2/2015 | Desai et al. |
| 2015/0079177 A1 | 3/2015 | Desai et al. |
| 2015/0079181 A1 | 3/2015 | Desai et al. |
| 2015/0104521 A1 | 4/2015 | Desai et al. |
| 2015/0111960 A1 | 4/2015 | Desai et al. |
| 2015/0157722 A1 | 6/2015 | Foss et al. |
| 2015/0165047 A1 | 6/2015 | Desai et al. |
| 2015/0190519 A1 | 7/2015 | Desai et al. |
| 2015/0313866 A1 | 11/2015 | Desai et al. |
| 2016/0015681 A1 | 1/2016 | Desai et al. |
| 2016/0015817 A1 | 1/2016 | Benettaib et al. |
| 2016/0151325 A1 | 6/2016 | Desai et al. |
| 2016/0228401 A1 | 8/2016 | Desai et al. |
| 2016/0374952 A1 | 12/2016 | Yeo et al. |
| 2017/0007569 A1 | 1/2017 | De et al. |
| 2017/0014373 A1 | 1/2017 | Desai et al. |
| 2017/0020824 A1 | 1/2017 | Desai et al. |
| 2017/0049711 A1 | 2/2017 | Desai et al. |
| 2017/0100344 A1 | 4/2017 | Desai et al. |
| 2017/0105951 A1 | 4/2017 | Desai et al. |
| 2017/0157035 A1 | 6/2017 | Seward et al. |
| 2017/0172975 A1 | 6/2017 | Desai et al. |
| 2017/0181988 A1 | 6/2017 | Desai et al. |
| 2017/0202782 A1 | 7/2017 | Pierce et al. |
| 2017/0224627 A1 | 8/2017 | Foss et al. |
| 2017/0333384 A1 | 11/2017 | Desai et al. |
| 2017/0340599 A1 | 11/2017 | Desai et al. |
| 2018/0015181 A1 | 1/2018 | Desai et al. |
| 2018/0064679 A1 | 3/2018 | Pierce et al. |
| 2018/0133157 A1 | 5/2018 | Desai et al. |
| 2018/0147139 A1 | 5/2018 | Seward et al. |
| 2018/0153863 A1 | 6/2018 | Desai et al. |
| 2018/0169017 A1 | 6/2018 | Desai et al. |
| 2018/0177770 A1 | 6/2018 | Desai et al. |
| 2018/0177771 A1 | 6/2018 | Desai et al. |
| 2018/0256551 A1 | 9/2018 | Desai et al. |
| 2018/0289620 A1 | 10/2018 | Desai et al. |
| 2018/0374583 A1 | 12/2018 | Goldstein et al. |
| 2019/0022020 A1 | 1/2019 | Desai et al. |
| 2019/0054033 A1 | 2/2019 | Foss et al. |

FOREIGN PATENT DOCUMENTS

| | | |
|---|---|---|
| WO | WO-94/18954 A1 | 9/1994 |
| WO | WO-98/14174 A1 | 4/1998 |
| WO | WO-98/14175 A1 | 4/1998 |
| WO | WO-99/00113 A1 | 1/1999 |
| WO | WO-00/64437 A1 | 11/2000 |
| WO | WO-00/71079 A2 | 11/2000 |
| WO | WO-00/71079 A3 | 11/2000 |
| WO | WO-01/89522 A1 | 11/2001 |
| WO | WO-02/087545 A1 | 11/2002 |
| WO | WO-03/096944 A1 | 11/2003 |
| WO | WO-2004/052401 A2 | 6/2004 |
| WO | WO-2004/052401 A3 | 6/2004 |
| WO | WO-2006/089290 A1 | 8/2006 |
| WO | WO-2007/027819 A2 | 3/2007 |
| WO | WO-2007/027819 A3 | 3/2007 |
| WO | WO-2007/027941 A2 | 3/2007 |
| WO | WO-2007/027941 A3 | 3/2007 |
| WO | WO-2008/027055 A1 | 3/2008 |
| WO | WO-2008/057562 A1 | 5/2008 |
| WO | WO-2008/076373 A1 | 6/2008 |
| WO | WO-2008/109163 A1 | 9/2008 |
| WO | WO-2008/137148 A2 | 11/2008 |
| WO | WO-2008/137148 A3 | 11/2008 |
| WO | WO-2008/150532 A1 | 12/2008 |

(56) References Cited

FOREIGN PATENT DOCUMENTS

| | | |
|---|---|---|
| WO | WO-2009/126175 A1 | 10/2009 |
| WO | WO-2009/126401 A1 | 10/2009 |
| WO | WO-2009/126938 A1 | 10/2009 |
| WO | WO-2010/068925 A1 | 6/2010 |
| WO | WO-2010/105172 A1 | 9/2010 |
| WO | WO-2010/118365 A1 | 10/2010 |
| WO | WO-2010/121000 A1 | 10/2010 |
| WO | WO-2011/025838 A1 | 3/2011 |
| WO | WO-2011/063309 A1 | 5/2011 |
| WO | WO-2011/119988 A1 | 9/2011 |
| WO | WO-2011/123393 A1 | 10/2011 |
| WO | WO-2011/123395 A1 | 10/2011 |
| WO | WO-2011/153009 A1 | 12/2011 |
| WO | WO-2011/153010 A1 | 12/2011 |
| WO | WO-2011/156119 A1 | 12/2011 |
| WO | WO-2012/149376 A2 | 11/2012 |
| WO | WO-2012/149451 A1 | 11/2012 |
| WO | WO-2013/090634 A1 | 6/2013 |
| WO | WO-2014/105644 A1 | 7/2014 |
| WO | WO-2014/110345 A1 | 7/2014 |
| WO | WO-2014/110408 A1 | 7/2014 |
| WO | WO-2014/110443 A1 | 7/2014 |
| WO | WO-2014/123612 A1 | 8/2014 |
| WO | WO-2014/143613 A1 | 9/2014 |
| WO | WO-2014/151853 A1 | 9/2014 |
| WO | WO-2014/159171 A1 | 10/2014 |
| WO | WO-2015/157120 A1 | 10/2015 |

OTHER PUBLICATIONS

Thomson, A.G. et al. (May 2009). "Immunoregulatory Functions of mTOR Inhibition," *Nat. Rev. Immunol.* 9(5):324-337, 27 pages.

Aldousari, S. et al. (Feb. 2010). "Update on the Management of Non-Muscle Invasive Bladder Cancer," *Canadian Urological Association* 4(1):56-64.

Altmayer, P. et al. (Oct. 1995). "Propofol Binding to Human Blood Proteins," *Arzneimittelforschung* 45(10):1053-1056.

Barry, W. T. et al.(2003). "Significance Analysis of Functional Categories in Gene Expression Studies: A Structured Permutation Approach," *Bioinformatics* 21 (9):1943-1949.

Bussemaker, H.J. et al. (2007). "Dissecting Complex Transcriptional Responses Using Pathway-Level Scores Based on Prior Information," *BMC Bioinformatics* 8:(Suppl 6)(S6):1-7.

Carter, D.C. et al. (1994). "Structure of Serum Albumin," *Adv. Protein. Chem.* 45:153-203.

Curry, S. et al. (Sep. 1998). "Crystal Structure of Human Serum Albumin Complexed With Fatty Acid Reveals an Asymmetric Distribution of Binding Sites," *Nat. Stmct. Biol.*, 5(9): 827-835.

Desai, N. (2007/2008). "Nab Technology: A Drug Delivery Platform Utilising Endothelial gp60 Receptor-based Transport and Tumour-derived SPARC for Targeting," *Drug Delivery Report Winter 2007/2008* pp. 37-41.

Fang, Y. et al. (Nov. 30, 2001). "Phosphatidic acid-mediated mitogenic activation of mTOR signaling," *Science* 294(5548): 1942-1945.

Fehske, K.J. et al. (1981). "The-Location of Drug Binding Sites in Human Serum Albumin," *Biochem. Pharmcol.* 30(7): 687-692.

Fingar, D.C. et al. (2002). "Mammalian cell size is controlled by mTOR and its downstream targets S6K1 and 4EBP1/eIF4E," *Genes Dev.* 16: 1472-1487.

Finlayson, J.S. (1980). "Albumin Products," *Seminars in Thrombosis and Hemostasis* 6(2):85-120.

Garrido, M.J. et al. (1994). "Binding Characteristics of Propofol to Plasma Proteins and Possible Interactions." *Rev. Esp. Anestestiol. Reanim.* 41:308-312. (Translation of the Summary only).

Garcia, J. A. et al. (Jun. 2008). "Mammalian Target of Rapamycin Inhibition as a Therapeutic Strategy in the Management of Urologic Malignancies," *Molecular Cancer Therapeutics* 7(6):1347-1354.

Hauser, C.J. et al. (Jun. 1980). "Oxygen Transport Responses to Colloids and Cystalloids in Critically Ill Surgical Patients," *Surgery, Gynecology and Obstetrics* 150(6):811-816.

He, X.M. et al. (Jul. 16, 1992). "Atomic Structure and Chemistry of Human Serum Albumin," *Nature* 358(6383):209-215.

Jacinto, E. et al. (Nov. 2004, e-pub. Oct. 3, 2004). "Mammalian TOR complex 2 controls the actin cytoskeleton and is rapamycin insensitive," *Nat. Cell Biol.* 6(11):1122-1128.

Kim, D-H. et al. (Jul. 26, 2002). "mTOR Interacts With Raptor to Form a Nutrient-Sensitive Complex That Signals to the Cell Growth Machinery," *Cell* 110:163-175.

Knight, Z.A. et al. (May 19, 2006). "A Pharmacological Map of the PI3-K Family Defines a Role for p110α in Insulin Signaling," *Cell* 125:733-747.

Kragh-Hansen, U. (Feb. 1990). "Structure and Ligand Binding Properties of Human Serum Albumin," *Dan. Med. Bull.* 37(1):57-84.

Lin, F. et al. (2013, e-pub. Feb. 22, 2013). "Dual mTORC1 and mTORC2 inhibitor Palomid 529 penetrates the Blood-Brain Barrier without restriction by ABCB1 and ABCG2," *Int. J. Cancer* 133:1222-1234.

Maglietta, R et al. (2007). "Statistical Assessment of Functional Categories of Genes Deregulated in Pathological Conditions by Using Microarray Data," *Bioinformatics* 23:2063-2072.

Milowsky, M. I., et al. (2011). 'Final Results of a Phase II Study of Everolimus (RAD001) in Metastatic Transitional Cell Carcinoma (TCC) of the Urothelium', *Journal of Clinical Oncology* 29(Suppl. 15), Abstract No. 4606, 1 page.

Müller, B.G. et al. (1996). "Albumin Nanospheres As Carriers for Passive Drug Targeting: An Optimized Manufacturing Technique, " *Pharmaceutical Research* 13(1):32-37.

Novak, B.A. et al. (2006). "Pathway Recognition and Augmentation by Computational Analysis of Microarray Expression Data," *Bioinformatics* 22:233-241.

Paal, K. et al. (2001). "High Affinity Binding of Paclitaxel to Human Serum Albumin," *Eur. J. Biochem.* 268(7), 2187-2191.

Paterson, D.L. et al. (May 31, 1998). "Bacillus Calmette-Guerin (BCG) Immunotherapy for Bladder Cancer: Review of Complications and Their Treatment," *The Australian & New Zealand Journal of Surgery* 68(5):340-344.

Pinto-Leite, R. et al. (Jan. 7, 2009). "Effect of Sirolimus on Urinary Bladder Cancer T24 Cell Line," *Journal of Experimental & Clinical Cancer Research* 28(3):1-6.

Porter, P.L. et al. (1995). "Distribution of SPARC in Normal and Neoplastic Human Tissue," *J. Histochem. Cytochem.* 43(8):791-800.

Purcell, M. et al. (2000). "Interaction of Taxol with Human Serum Albumin," *Biochim. Biophys. Acta* 1478:61-68.

Roper J, et al. (Sep. 26, 2011). "The Dual PI3K/mTOR Inhibitor NVP-BEZ235 Induces Tumor Regression in a Genetically Engineered Mouse Model of PIK3CA Wild-Type Colorectal Cancer," *PLoS One* 6(9)( e25132):1-10.

Sarbassov, D.D. et al. (Jul. 27, 2004). "Rictor, a Novel Binding Partner of mTOR, Defines a Rapamycin-Insensitive and Raptor-Independent Pathway That Regulates the Cytoskeleton," *Curr. Biol.* 14:1296-1302.

Seager, C. M., 'Intravesical Delivery of Rapamycin Suppresses Tumorigenesis in a Mouse Model of Progressive Bladder Cancer', *Cancer Prev Res* (Phila), Dec. 2009; vol. 2, No. 12, pp. 1008-1014.

Segal, E. et al. (Jun. 2003). "Module networks: identifying regulatory modules and their condition-specific regulators from gene expression data," *Nat. Genetics* 34(2):166-176.

Segal, E. et al. (Oct. 2004). "A Module Map Showing Conditional Activity of Expression Modules in Cancer," *Nat. Genet.* 36(10):1090-1098.

Seront, E. et al. (Oct. 2012). Phase II Study of Everolimus in Patients with Locally Advanced or Metastatic Transitional Cell Carcinoma of the Urothelial Tract: Clinical Activity, Molecular Response, and Biomarkers, *Annals of Oncology* 23(10):2663-2670.

Schultz, L. et al. (Dec. 1, 2010). Expression Status and Prognostic Significance of Mammalian Target of Rapamycin Pathway Members in Urothelial Carcinoma of Urinary Bladder After Cystectomy, *Cancer* 116:5517-5526.

Sugio, S. et al. (1999). "Crystal Structure of Human Serum Albumin at 2.5 Å Resolution," *Protein. Eng.* 12(6):439-446.

(56) References Cited

OTHER PUBLICATIONS

Tian, L. et al. (Sep. 20, 2005). "Discovering Statistically Significant Pathways in Expression Profiling Studies," *Proc. Nat'l. Acad. Sci. U.S.A.* 102:13544-13549.

Tullis, J.L. (1977). "Albumin. 1. Background and Use," *JAMA*, 237(4): 355-360.

Tullis, J.L. (1977). "Albumin. 2. Guidelines for Clinical Use," *JAMA*, 237(5):460-463.

Urien, S. et al. (May 1996). "Docetaxel Serum Protein Binding with High Affinity to Alpha-Acid Glcoprotein," *Invest. New Drugs* 14(b), 147-151.

Vorum, H. (Nov. 1999). "Reversible Ligand Binding to Human Serum Albumin," *Dan. Med. Bull.* 46(5):379-399.

Wu, J-Q. et al. (2003) "Spatial and temporal pathway for assembly and constriction of the contractile ring in fission yeast cytokinesis," *Dev. Cell* 5:723-34.

Yoo, H.K. et al. (2012). "Monthly Intravesical Bacillus Calmette-Guérin Maintenance Therapy for Non-Muscle-Invasive Bladder Cancer: 10-Year Experience in a Single Institute," *Experimental and Therapeutic Medicine* 3:221-225.

International Search Report dated Jun. 4, 2014, for PCT Application No. PCT/US2014/026564, filed on Mar. 13, 2014, 5 pages.

Written Opinion dated Jun. 4, 2014, for PCT Application No. PCT/US2014/026564, filed on Mar. 13, 2014, 9 pages.

European Search Report and Search Opinion dated Oct. 19, 2016, for European Patent Application No. 14767736.3 filed on Mar. 13, 2014, 7 pages.

U.S. Appl. No. 15/399,366, filed Jan. 5, 2017, for Pierce et al.

U.S. Appl. No. 15/462,361, filed Mar. 17, 2017, for Tao et al.

U.S. Appl. No. 15/663,351, filed Jul. 28, 2017, for Desai et al.

U.S. Appl. No. 15/796,578, filed Oct. 27, 2017, for Desai et al.

U.S. Appl. No. 15/738,087, filed internationally Jun. 29, 2016, for Desai et al.

U.S. Appl. No. 15/879,320, filed Jan. 24, 2018, for Desai et al.

U.S. Appl. No. 15/981,276, filed May 16, 2018, for Desai et al.

Goodman, L.S. et al. eds. (1996). Goodman & Gilman's The Pharmacological Basis of Therapeutics, 9th Edition, New York, McGraw-Hill, Health Professions Divisions, pp. v-xii, (Table of Contents, total number of pp. 10).

U.S. Appl. No. 16/101,027, filed Aug. 10, 2018, for Desai et al.

U.S. Appl. No. 16/170,522, filed Oct. 25, 2018, for Desai et al.

Castellano, D. et al. (2012). "Recommandations for the Optimal Management of Early and Advanced Urothelial Carcinoma," *Cancer Treatment Reviews* 38(5):431-441.

European Communication Pursuant to Article 94(3) EPC, for European Patent Application No. 14767736.3, dated May 29, 2019, filed Oct. 9, 2015, 7 pages.

Kim, J.J. (2012, e-pub. Feb. 26, 2012). "Recent Advances in Treatment of Advanced Urothelial Carcinoma," *Current Urology Reports* 13(2):147-152.

Lamm, D.L. et al. (Apr. 2000). "Maintenance Bacillus Calmette-Guerin Immunotherapy for Recurrent TA, T1 and Carcinoma in Situ Transitional Cell Carcinoma of the Bladder: A Randomized Southwest Oncology Group Study," *J. Urol.* 163(4):1124-1129.

Nirmal, J. et al. (2012, e-pub. Aug. 24, 2012). "Intravesical Therapy for Lower Urinary Tract Symptoms," *Urological Science* 23(3):70-77.

Sun, H.-Y. et al. (Aug. 1, 2010). "Should Intravesical Bacillus Calmette-Guérin be Employed in Transplant Recipients with bladder carcinoma?," *Transplant Infectious Disease* 12(4):358-362.

METHODS OF TREATING BLADDER CANCER

RELATED APPLICATIONS

This application is a continuation of U.S. patent application Ser. No. 14/772,725, which adopts the international filing date of Mar. 13, 2014, which is a is a National Phase application under 35 U.S.C. § 371 of International Application No. PCT/US2014/026564, filed Mar. 13, 2014, which claims priority benefit to U.S. Provisional Application No. 61/786,167 and U.S. Provisional Application No. 61/786,175, filed Mar. 14, 2013, the content of each of which are herein incorporated by reference in their entirety.

TECHNICAL FIELD

The present invention relates to methods and compositions for the treatment of bladder cancer by administering compositions comprising nanoparticles that comprise a limus drug and an albumin.

BACKGROUND

In the U.S., bladder cancer is the fourth most common type of cancer in men and the ninth most common cancer in women. Smoking and age are the main known risk factors, with nearly 90% of patients over age of 55. In 2011, it is estimated that there will be 69,250 new cases in the U.S., resulting in 14,990 deaths. Non-muscle invasive bladder cancer (NMIBC) begins and stays in the cells lining the bladder without growing into the deeper main muscle layer of the bladder, and accounts for the majority (70-80%) of patients diagnosed with bladder cancer (stages Ta, T1, or CIS). Approximately 30% of patients present with muscle-invasive disease (stages T2-T4). Bladder cancer has the highest recurrence rate of any malignancy. Although NMIBC is a relatively benign disease, it recurs in 50-70% of patients, of which 10-20% would eventually progress to high-grade muscle-invasive disease. Furthermore, the disease is also characterized by having a large pool of patients who have been previously diagnosed and are still undergoing treatment for unresolved tumors; more than 1 million patients in the U.S. and Europe are estimated to be affected by the disease.

The high-grade muscle invasive disease is typically treated with radical cystectomy or a combination of radiation therapy and chemotherapy. However, even after treatment the tumor usually remains and patients are at risk of tumor progression, leading to a shortened life expectancy or death from metastatic disease. Approximately 350,000 patients in the U.S. and EU are currently undergoing treatment for unresolved tumors.

NMIBC is typically treated with intravesicular BCG, which elicits a nonspecific local immune response against the tumor cells. BCG elicits a nonspecific massive local inflammatory reaction in the bladder wall, and elevated appearance of cytokines can be detected in the urine of BCG-treated patients. BCG is internalized by antigen-presenting cells, such as macrophages, but also by urothelial tumor cells, which result in an altered gene expression of these cells. Additionally, none of the available chemotherapeutic agents, including gemcitabine, cisplatin, and valrubicin, that are currently explored in clinical trials for treating bladder cancer are targeted therapeutics.

Sirolimus (INN/USAN), also known as rapamycin, is an immunosuppressant drug used to prevent rejection in organ transplantation; it is especially useful in kidney transplants. It prevents activation of T cells and B cells by inhibiting their response to interleukin-2 (IL-2). The mode of action of sirolimus is to bind the cytosolic protein FK-binding protein 12 (FKBP12), and the sirolimus-FKBP12 complex in turn inhibits the mammalian target of sirolimus (mTOR) pathway by directly binding the mTOR Complex1 (mTORC1).

Albumin-based nanoparticle compositions have been developed as a drug delivery system for delivering substantially water insoluble drugs. See, for example, U.S. Pat. Nos. 5,916,596; 6,506,405; 6,749,868, and 6,537,579, 7,820,788, and 7,923,536. Abraxane®, an albumin stabilized nanoparticle formulation of paclitaxel, was approved in the United States in 2005 and subsequently in various other countries for treating metastatic breast cancer. It was recently approved for treating non-small cell lung cancer in the United States, and has also shown therapeutic efficacy in various clinical trials for treating difficult-to-treat cancers such as bladder cancer and melanoma. Albumin derived from human blood has been used for the manufacture of Abraxane® as well as various other albumin-based nanoparticle compositions.

The disclosures of all publications, patents, patent applications and published patent applications referred to herein are hereby incorporated herein by reference in their entirety.

BRIEF SUMMARY OF THE INVENTION

The present invention provides methods of treating bladder cancer in an individual, comprising administering to the individual an effective amount of a composition comprising nanoparticles comprising an mTOR inhibitor (such as a limus drug). In some embodiments, there is provided a method of treating bladder cancer in an individual, comprising administering to the individual an effective amount of a composition comprising nanoparticles comprising a limus drug and an albumin. In some embodiments, the limus drug is sirolimus. In some embodiments, the albumin is human albumin (such as human serum albumin). In some embodiments, the nanoparticles comprise sirolimus coated with albumin. In some embodiments, the average particle size of the nanoparticles in the nanoparticle composition is no more than about 200 nm (such as no greater than about 150 nm). In some embodiments, the composition comprises the albumin stabilized nanoparticle formulation of sirolimus (Nab-sirolimus). In some embodiments, the composition is Nab-sirolimus.

In some embodiments, there is provided a method of treating bladder cancer in an individual, comprising administering to the individual an effective amount of a composition comprising nanoparticles comprising a limus drug and an albumin, wherein the limus drug is coated with the albumin. In some embodiments, there is provided a method of treating bladder cancer in an individual, comprising administering to the individual an effective amount of a composition comprising nanoparticles comprising a limus drug and an albumin, wherein the average particle size of the nanoparticles in the nanoparticle composition is no greater than about 200 nm (such as less than about 150 nm). In some embodiments, there is provided a method of treating bladder cancer in an individual, comprising administering to the individual an effective amount of a composition comprising nanoparticles comprising a limus drug and an albumin, wherein the limus drug is coated with the albumin, and wherein the average particle size of the nanoparticles in the nanoparticle composition is no greater than about 200 nm (such as no greater than about 150 nm). In some embodiments, there is provided a method of treating bladder cancer in an individual, comprising administering to the individual an effective amount of a composition comprising Nab-sirolimus. In some embodiments, there is provided a method of treating bladder cancer in an individual, comprising administering to the individual an effective amount of Nab-sirolimus.

In some embodiments, the composition is administered intravenously. In some embodiments, the composition is administered intravesicularly (for example via urethral catheterization).

Also provided are combination therapy methods for treating bladder cancer. For example, in some embodiments, there is provided a method of treating bladder cancer in an individual, comprising administering to the individual (a) an effective amount of a composition comprising nanoparticles comprising an mTOR inhibitor (such as a limus drug); and (b) an effective amount of another agent (such as BCG). In some embodiments, there is provided a method of treating bladder cancer in an individual, comprising administering to the individual (a) an effective amount of a composition comprising nanoparticles comprising a limus drug and albumin; and (b) an effective amount of another agent (such as BCG). The nanoparticle composition and the other agent can be administered simultaneously or sequentially. In some embodiments, the nanoparticle composition and the other agent are administered concurrently. In some embodiments, the limus drug is sirolimus. In some embodiments, the albumin is human serum albumin. In some embodiments, the nanoparticles comprise sirolimus coated with albumin. In some embodiments, the average particle size of the nanoparticles in the nanoparticle composition is no more than about 200 nm (such as no greater than about 200 nm). In some embodiments, the composition comprises the albumin stabilized nanoparticle formulation of sirolimus (Nab-sirolimus). In some embodiments, the composition is Nab-sirolimus.

In some embodiments, the method is carried out in a neoadjuvant setting. In some embodiments, the method is carried out in an adjuvant setting. In some embodiments, the method is carried out after resection of visible tumor in the bladder.

Bladder cancer that can be treated with methods described herein include, but are not limited to, metastatic bladder cancer, non-muscle-invasive bladder cancer, or bladder cancer that is refractory to a standard therapy (such as Bacillus Calmette-Guérin (BCG) or recurrent after the standard therapy. In some embodiments, the bladder cancer is ECG-refractory non-muscle-invasive bladder cancer. In some embodiments, the bladder cancer is platinum-refractory bladder cancer. In some embodiments, the bladder cancer is platinum-refractory metastatic urothelial carcinoma. In some embodiments, the treatment is first line treatment. In some embodiments, the treatment is second line treatment.

In some embodiments, there is provided a method of treating bladder cancer in an individual, comprising intravesicularly administering (for example via urethral catheterization) to the individual an effective amount of a composition comprising nanoparticles comprising a limus drug and an albumin. In some embodiments, there is provided a method of treating non-muscle-invasive bladder cancer in an individual, comprising intravesicularly administering (for example via urethral catheterization) to the individual an effective amount of a composition comprising nanoparticles comprising a limus drug and an albumin. In some embodiments, the individual has progressed from an earlier therapy for bladder cancer. In some embodiments, the individual is refractory to an earlier therapy for bladder cancer. In some embodiments, the individual has recurrent bladder cancer. In some embodiments, there is provided a method of treating a BCG-refractory non-muscle-invasive bladder cancer in an individual, comprising intravesicularly administering (for example via urethral catheterization) to the individual an effective amount of a composition comprising nanoparticles comprising a limus drug and an albumin. In some embodiments, the amount of the nanoparticle composition is about 5 mg to about 500 mg, including for example about 30 mg to about 400 mg (such as about 100 mg). In some embodiments, the nanoparticle composition is administered weekly.

Also provided are methods of treating bladder cancer according to any one of the methods described above, wherein the treatment is based on the level of one or more biomarkers.

The methods described herein can be used for any one or more of the following purposes: alleviating one or more symptoms of bladder cancer, delaying progressing of bladder cancer, shrinking tumor size in bladder cancer patient, inhibiting bladder cancer tumor growth, prolonging overall survival, prolonging disease-free survival, prolonging time to bladder disease progression, preventing or delaying bladder cancer metastasis, reducing (such as eradiating) preexisting bladder cancer metastasis, reducing incidence or burden of preexisting bladder cancer metastasis, preventing recurrence of bladder cancer.

DETAILED DESCRIPTION OF THE INVENTION

The present invention provides methods and compositions for treating bladder cancer by administering a composition comprising nanoparticles comprising an mTOR inhibitor (hereinafter also referred to as "mTOR nanoparticle composition"). In some embodiments, the composition comprises a limus drug and an albumin (hereinafter also referred to as "limus nanoparticle composition"). Also provided are compositions (such as pharmaceutical compositions), medicine, kits, and unit dosages useful for the methods described herein.

Definitions

As used herein, "treatment" or "treating" is an approach for obtaining beneficial or desired results including clinical results. For purposes of this invention, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread (e.g., metastasis) of the disease, preventing or delaying the recurrence of the disease, reducing recurrence rate of the disease, delay or slowing the progression of the disease, ameliorating the disease state, providing a remission (partial or total) of the disease, decreasing the dose of one or more other medications required to treat the disease, delaying the progression of the disease, increasing the quality of life, and/or prolonging survival. Also encompassed by "treatment" is a reduction of pathological consequence of bladder cancer. The methods of the invention contemplate any one or more of these aspects of treatment.

The term "individual" refers to a mammal and includes, but is not limited to, human, bovine, horse, feline, canine, rodent, or primate.

As used herein, an "at risk" individual is an individual who is at risk of developing bladder cancer. An individual "at risk" may or may not have detectable disease, and may or may not have displayed detectable disease prior to the treatment methods described herein. "At risk" denotes that an individual has one or more so-called risk factors, which are measurable parameters that correlate with development of bladder cancer, which are described herein. An individual having one or more of these risk factors has a higher probability of developing cancer than an individual without these risk factor(s).

"Adjuvant setting" refers to a clinical setting in which an individual has had a history of bladder cancer, and generally (but not necessarily) been responsive to therapy, which includes, but is not limited to, surgery (e.g., surgery resection), radiotherapy, and chemotherapy. However, because of their history of bladder cancer, these individuals are considered at risk of development of the disease. Treatment or administration in the "adjuvant setting" refers to a subsequent mode of treatment. The degree of risk (e.g., when an individual in the adjuvant setting is considered as "high risk" or "low risk") depends upon several factors, most usually the extent of disease when first treated.

"Neoadjuvant setting" refers to a clinical setting in which the method is carried out before the primary/definitive therapy.

As used herein, "delaying" the development of bladder cancer means to defer, hinder, slow, retard, stabilize, and/or postpone development of the disease. This delay can be of varying lengths of time, depending on the history of the disease and/or individual being treated. As is evident to one skilled in the art, a sufficient or significant delay can, in effect, encompass prevention, in that the individual does not develop the disease. A method that "delays" development of bladder cancer is a method that reduces probability of disease development in a given time frame and/or reduces the extent of the disease in a given time frame, when compared to not using the method. Such comparisons are typically based on clinical studies, using a statistically significant number of subjects. Bladder cancer development can be detectable using standard methods, including, but not limited to, computerized axial tomography (CAT scan), Magentic Resonance Imaging (MRI), ultrasound, clotting tests, arteriography, biopsy, urine cytology, and cystoscopy. Development may also refer to bladder cancer progression that may be initially undetectable and includes occurrence, recurrence, and onset.

As used herein, by "combination therapy" is meant that a first agent be administered in conjunction with another agent. "In conjunction with" refers to administration of one treatment modality in addition to another treatment modality, such as administration of a nanoparticle composition described herein in addition to administration of the other agent to the same individual. As such, "in conjunction with" refers to administration of one treatment modality before, during, or after delivery of the other treatment modality to the individual.

The term "effective amount" used herein refers to an amount of a compound or composition sufficient to treat a specified disorder, condition or disease such as ameliorate, palliate, lessen, and/or delay one or more of its symptoms. In reference to bladder cancer, an effective amount comprises an amount sufficient to cause a tumor to shrink and/or to decrease the growth rate of the tumor (such as to suppress tumor growth) or to prevent or delay other unwanted cell proliferation in bladder cancer. In some embodiments, an effective amount is an amount sufficient to delay development of bladder cancer. In some embodiments, an effective amount is an amount sufficient to prevent or delay recurrence. In some embodiments, an effective amount is an amount sufficient to reduce recurrence rate in the individual. An effective amount can be administered in one or more administrations. In the case of bladder cancer, the effective amount of the drug or composition may: (i) reduce the number of bladder cancer cells; (ii) reduce tumor size; (iii) inhibit, retard, slow to some extent and preferably stop bladder cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; (vii) reducing recurrence rate of tumor, and/or (viii) relieve to some extent one or more of the symptoms associated with bladder cancer.

The term "simultaneous administration," as used herein, means that a first therapy and second therapy in a combination therapy are administered with a time separation of no more than about 15 minutes, such as no more than about any of 10, 5, or 1 minutes. When the first and second therapies are administered simultaneously, the first and second therapies may be contained in the same composition (e.g., a composition comprising both a first and second therapy) or in separate compositions (e.g., a first therapy in one composition and a second therapy is contained in another composition).

As used herein, the term "sequential administration" means that the first therapy and second therapy in a combination therapy are administered with a time separation of more than about 15 minutes, such as more than about any of 20, 30, 40, 50, 60, or more minutes. Either the first therapy or the second therapy may be administered first. The first and second therapies are contained in separate compositions, which may be contained in the same or different packages or kits.

As used herein, the term "concurrent administration" means that the administration of the first therapy and that of a second therapy in a combination therapy overlap with each other.

As used herein, by "pharmaceutically acceptable" or "pharmacologically compatible" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

It is understood that aspect and embodiments of the invention described herein include "consisting" and/or "consisting essentially of" aspects and embodiments.

Reference to "about" a value or parameter herein includes (and describes) variations that are directed to that value or parameter per se. For example, description referring to "about X" includes description of "X".

As used herein and in the appended claims, the singular forms "a," "or," and "the" include plural referents unless the context clearly dictates otherwise.

Methods of Treating Bladder Cancer

The present invention provides methods of treating bladder cancer in an individual (such as human) comprising administering to the individual an effective amount of a composition comprising nanoparticles comprising an mTOR inhibitor (such as a limus drug). In some embodiments, the invention provides methods of treating bladder cancer in an individual (e.g., human) comprising administering to the individual an effective amount of a composition comprising nanoparticles comprising a limus drug and an albumin. In some embodiments, the method comprises administering to the individual an effective amount of a composition comprising nanoparticles comprising a limus drug and an albumin, wherein the limus drug in the nanoparticles is coated with the albumin. In some embodiments, the method comprises administering to the individual an effective amount of a composition comprising nanoparticles comprising a limus drug and an albumin, wherein the nanoparticles have an average particle size of no greater than about 200 nm (such as no greater than about 150 nm). In some embodiments, the method comprises administering to the individual an effective amount of a composition comprising nanoparticles comprising a limus drug and an albumin, wherein the nanoparticles comprise a limus drug coated with albumin, wherein the nanoparticles have an average particle size of no greater than about 200 nm (such as no greater than about 150 nm). In some embodiments, the method comprises administering to the individual an effective amount of a composition comprising nanoparticles comprising sirolimus and human albumin, wherein the nanoparticles comprise sirolimus coated with human albumin, wherein the nanoparticles have an average particle size of no greater than about 150 nm (such as no greater than about 120 nm, for example about 100 nm), wherein the weight ratio of human albumin and sirolimus in the composition is about 9:1 or less (such as about 9:1 or about 8:1). In some embodiments, the composition comprises Nab-sirolimus. In some embodiments, the composition is Nab-sirolimus.

"mTOR inhibitor" used herein refers to inhibitors of mTOR. mTOR is a serine/threonine-specific protein kinase downstream of the phosphatidylinositol 3-kinase (PBK)/Akt (protein kinase B) pathway, and a key regulator of cell survival, proliferation, stress, and metabolism. mTOR pathway dysregulation has been found in many human carcinomas, and mTOR inhibition produced substantial inhibitory effects on tumor progression. mTOR inhibitors described herein include, but are not limited to, BEZ235 (NVP-BEZ235), everolimus (also known as RAD001 and sold under the trademarks Zortress®, Certican®, and Afinitor®), rapamycin (also known as sirolimus and sold under the trademark Rapamune®), AZD8055, temsirolimus (also known as CCI-779 and sold under the trademark Torisel®), PI-103, Ku-0063794, INK 128, AZD2014, NVP-BGT226, PF-04691502, CH5132799, GDC-0980 (RG7422), Torin 1, WAY-600, WYE-125132, WYE-687, GSK2126458, PF-05212384 (PKI-587), PP-121, OSI-027, Palomid 529, PP242, XL765, GSK1059615, WYE-354, and eforolimus (also known as ridaforolimus or deforolimus).

In some embodiments, the mTOR inhibitor is a limus drug, which includes sirolimus and its analogues. Examples of limus drugs include, but are not limited to, temsirolimus (CCI-779), everolimus (RAD001), ridaforolimus (AP-23573), deforolimus (MK-8669), zotarolimus (ABT-578), pimecrolimus, and tacrolimus (FK-506). In some embodiments, the limus drug is selected from the group consisting of temsirolimus (CCI-779), everolimus (RAD001), ridaforolimus (AP-23573), deforolimus (MK-8669), zotarolimus (ABT-578), pimecrolimus, and tacrolimus (FK-506).

In some embodiments, the bladder cancer is a low grade bladder cancer. In some embodiments, the bladder cancer is a high grade bladder cancer. In some embodiments, the bladder cancer is invasive. In some embodiments, the bladder cancer is non-invasive. In some embodiments, the bladder cancer is non-muscle invasive.

In some embodiments, the bladder cancer is transitional cell carcinoma or urothelial carcinoma (such as metastatic urothelial carcinoma), including, but not limited to, papillary tumors and flat carcinomas. In some embodiments, the bladder cancer is metastatic urothelial carcinoma. In some embodiments, the bladder cancer is urothelial carcinoma of the bladder. In some embodiments, the bladder cancer is urothelial carcinoma of the ureter. In some embodiments, the bladder cancer is urothelial carcinoma of the urethra. In some embodiments, the bladder cancer is urothelial carcinoma of the renal pelvis.

In some embodiments, the bladder cancer is squamous cell carcinoma. In some embodiments, the bladder cancer is non-squamous cell carcinoma. In some embodiments, the bladder cancer is adenocarcinoma. In some embodiments, the bladder cancer is small cell carcinoma.

In some embodiments, the bladder cancer is early stage bladder cancer, non-metastatic bladder cancer, non-invasive bladder cancer, non-muscle-invasive bladder cancer, primary bladder cancer, advanced bladder cancer, locally advanced bladder cancer (such as unresectable locally advanced bladder cancer), metastatic bladder cancer, or bladder cancer in remission. In some embodiments, the bladder cancer is localized resectable, localized unresectable, or unresectable. In some embodiments, the bladder cancer is a high grade, non-muscle-invasive cancer that has been refractory to standard intra-bladder infusion (intravesicular) therapy.

The methods provided herein can be used to treat an individual (e.g., human) who has been diagnosed with or is suspected of having bladder cancer. In some embodiments, the individual is human. In some embodiments, the individual is at least about any of 20, 25, 30, 35, 40, 45, 50, 55, 60, 65, 70, 75, 80, or 85 years old. In some embodiments, the individual is male. In some embodiments, the individual is female. In some embodiments, the individual has undergone a tumor resection. In some embodiments, the individual has refused surgery. In some embodiments, the individual is medically inoperable. In some embodiments, the individual is at a clinical stage of Ta, Tis, T1, T2, T3a, T3b, or T4 bladder cancer. In some embodiments, the individual is at a clinical stage of Tis, CIS, Ta, or T1.

In some embodiments, the individual is a human who exhibits one or more symptoms associated with bladder cancer. In some embodiments, the individual is at an early stage of bladder cancer. In some embodiments, the individual is at an advanced stage of bladder cancer. In some of embodiments, the individual is genetically or otherwise predisposed (e.g., having a risk factor) to developing bladder cancer. Individuals at risk for bladder cancer include, e.g., those having relatives who have experienced bladder cancer, and those whose risk is determined by analysis of genetic or biochemical markers. In some embodiments, the individual is positive for SPARC expression (for example based on immunohistochemistry (IHC) standard). In some embodiments, the individual is negative for SPARC expression. In some embodiments, the individual has a mutation in FGFR2. In some embodiments, the individual has a mutation in p53. In some embodiments, the individual has a mutation in MIB-1. In some embodiments, the individual has a mutation in one or more of FEZ1/LZTS1, PTEN, CDKN2A/MTS1/P6, CDKN2B/INK4B/P15, TSC1, DBCCR1, HRAS1, ERBB2, or NFL In some embodiments, the individual has mutation in both p53 and PTEN.

The present invention for example provides in some embodiments methods of treatment bladder cancer in an individual comprising administering to the individual an effective amount of a composition comprising nanoparticles comprising an mTOR inhibitor (such as a lumus drug), wherein the treatment is based on the mutation status of one or more of FEZ1/LZTS1, PTEN, CDKN2A/MTS1/P6, CDKN2B/INK4B/P15, TSC1, DBCCR1, HRAS1, ERBB2, or NF1. In some embodiments, there is provided a method of treating bladder cancer in an individual comprising administering to the individual an effective amount of a composition comprising nanoparticles comprising an mTOR inhibitor (such as a limus drug), wherein the individual is selected for treatment based on the mutation status of one or more of FEZ1/LZTS1, PTEN, CDKN2A/MTS1/P6, CDKN2B/INK4B/P15, TSC1, DBCCR1, HRAS1, ERBB2, or NF1. In some embodiments, there is provided a method of selecting (including identifying) an individual having bladder cancer for treating with a composition comprising nanoparticles comprising an mTOR inhibitor (such as a limus drug), wherein the method comprises determining the mutation status of one or more of FEZ1/LZTS1, PTEN, CDKN2A/MTS1/P6, CDKN2B/INK4B/P15, TSC1, DBCCR1, HRAS1, ERBB2, or NF1. The mutation status of one or more of FEZ1/LZTS1, PTEN, CDKN2A/MTS1/P6, CDKN2B/INK4B/P15, TSC1, DBCCR1, HRAS1, ERBB2, or NF1 can also be useful for determining any of the following: (a) probable or likely suitability of an individual to initially receive treatment(s); (b) probable or likely unsuitability of an individual to initially receive treatment(s); (c) responsiveness to treatment; (d) probable or likely suitability of an individual to continue to receive treatment(s); (e) probable or likely unsuitability of an individual to continue to receive treatment(s); (f) adjusting dosage; (g) predicting likelihood of clinical benefits.

In some embodiments, the individual has a partial or complete monosomy (such as monosomy 9). In some embodiments, the individual has a deletion in chromosome 11p. In some embodiments, the individual has a deletion in chromosome 13q. In some embodiments, the individual has a deletion in chromosome 17p. In some embodiments, the individual has a deletion in chromosome ip. In some embodiments, the individual as a chromosome loss of 8p12-22.

In some embodiments, the individual overexpresses p73, c-myc, or cyclin D1.

The methods provided herein may be practiced in an adjuvant setting. In some embodiments, the method is practiced in a neoadjuvant setting, i.e., the method may be carried out before the primary/definitive therapy. In some embodiments, the method is used to treat an individual who has previously been treated. In some embodiments, the individual has not previously been treated. In some embodiments, the method is used as a first line therapy. In some embodiments, the method is used as a second line therapy.

In some embodiments, the individual has been previously treated for bladder cancer (also referred to as the "prior therapy"). In some embodiments, individual has been previously treated with a standard therapy for bladder cancer. In some embodiments, the prior standard therapy is treatment with BCG. In some embodiments, the prior standard therapy is treatment with mitomycin C. In some embodiments, the prior standard therapy is treatment with interferon (such as interferon-α). In some embodiments, the individual has bladder cancer in remission, progressive bladder cancer, or recurrent bladder cancer. In some embodiments, the individual is resistant to treatment of bladder cancer with other agents (such as platinum-based agents, BCG, mitomycin C, or interferon). In some embodiments, the individual is initially responsive to treatment of bladder cancer with other agents (such as platinum-based agents, or BCG) but has progressed after treatment.

In some embodiments, the individual has recurrent bladder cancer (such as a bladder cancer at the clinical stage of Ta, Tis, T1, T2, T3a, T3b, or T4) after a prior therapy (such as prior standard therapy, for example treatment with BCG). For example, the individual may be initially responsive to the treatment with the prior therapy, but develops bladder cancer after about any of about 2, 3, 4, 5, 6, 7, 8, 9, 10, 11, 12, 24, 36, 48, or 60 months upon the cessation of the prior therapy.

In some embodiments, the individual is refractory to a prior therapy (such as prior standard therapy, for example treatment with BCG).

In some embodiments, the individual has progressed on the prior therapy (such as prior standard therapy, for example treatment with BCG) at the time of treatment. For example, the individual has progressed within any of about 1, 2, 3, 4, 5, 6, 7, 8, 9, 10, 11, or 12 months upon treatment with the prior therapy.

In some embodiments, the individual is resistant to the prior therapy (such as prior standard therapy, for example treatment with BCG).

In some embodiments, the individual is unsuitable to continue with the prior therapy (such as prior standard therapy, for example treatment with BCG), for example due to failure to respond and/or due to toxicity.

In some embodiments, the individual is non-responsive to the prior therapy (such as prior standard therapy, for example treatment with BCG).

In some embodiments, the individual is partially responsive to the prior therapy (such as prior standard therapy, for example treatment with BCG), or exhibits a less desirable degree of responsiveness.

In some embodiments, there is provided a method of treating bladder cancer in an individual (e.g., human) comprising intravesicularly administering (for example via urethral catheterization) to the individual an effective amount of a composition comprising nanoparticles comprising an mTOR inhibitor (such as a limus drug). In some embodiments, there is provided a method of treating bladder cancer in an individual (e.g., human) comprising intravesicularly administering (for example via urethral catheterization) to the individual an effective amount of a composition comprising nanoparticles comprising an mTOR inhibitor (such as a limus drug) and an albumin. In some embodiments, there is provided a method of treating bladder cancer in an individual (e.g., human) comprising intravesicularly administering (for example via urethral catheterization) to the individual an effective amount of a composition comprising nanoparticles comprising an mTOR inhibitor (such as a limus drug) and an albumin, wherein the mTOR inhibitor (such as a limus drug) in the nanoparticles is coated with the albumin. In some embodiments, there is provided a method of treating bladder cancer in an individual (e.g., human) comprising intravesicularly administering (for example via urethral catheterization) to the individual an effective amount of a composition comprising nanoparticles comprising an mTOR inhibitor (such as a limus drug) and an albumin, wherein the nanoparticles have an average particle size of no greater than about 200 nm (such as no greater than about 150 nm). In some embodiments, there is provided a method of treating bladder cancer in an individual (e.g., human) comprising intravesicularly administering (for example via urethral catheterization) to the individual an effective amount of a composition comprising nanoparticles comprising an mTOR inhibitor (such as a limus drug) and an albumin, wherein the nanoparticles comprise the mTOR inhibitor (such as a limus drug) coated with albumin, and wherein the nanoparticles have an average particle size of no greater than about 200 nm (such as no greater than about 150 nm). In some embodiments, there is provided a method of treating bladder cancer in an individual (e.g., human) comprising intravesicularly administering (for example via urethral catheterization) to the individual an effective amount of a composition comprising nanoparticles comprising an mTOR inhibitor (such as a limus drug) and human albumin, wherein the nanoparticles comprise the mTOR inhibitor (such as a limus drug) coated with the human albumin, wherein the nanoparticles have an average particle size of no greater than about 150 nm (such as no greater than about 120 nm, for example about 100 nm), wherein the weight ratio of human albumin and the mTOR inhibitor (such as a limus drug) in the composition is about 9:1 or less (such as about 9:1 or about 8:1). In some embodiments, the mTOR inhibitor (i.e., the mTOR inhibitor in the mTOR nanoparticle composition) is administered at a dose of about 5 mg to about 500 mg (including for example about 30 mg to about 400 mg, such as about 100 mg). In some embodiments, the limus nanoparticle composition is administered weekly. In some embodiments, the composition is administered weekly for 6 weeks, optionally followed by monthly maintenance thereafter.

In some embodiments, there is provided a method of treating bladder cancer in an individual (e.g., human) comprising intravesicularly administering (for example via urethral catheterization) to the individual an effective amount of a composition comprising nanoparticles comprising an mTOR inhibitor (such as a limus drug). In some embodiments, there is provided a method of treating bladder cancer in an individual (e.g., human) comprising intravesicularly administering (for example via urethral catheterization) to the individual an effective amount of a composition comprising nanoparticles comprising a limus drug and an albumin. In some embodiments, there is provided a method of treating bladder cancer in an individual (e.g., human) comprising intravesicularly administering (for example via urethral catheterization) to the individual an effective amount of a composition comprising nanoparticles comprising a limus drug and an albumin, wherein the limus drug in the nanoparticles is coated with the albumin. In some embodiments, there is provided a method of treating bladder cancer in an individual (e.g., human) comprising intravesicularly administering (for example via urethral catheterization) to the individual an effective amount of a composition comprising nanoparticles comprising a limus drug and an albumin, wherein the nanoparticles have an average particle size of no greater than about 200 nm (such as no greater than about 150 nm). In some embodiments, there is provided a method of treating bladder cancer in an individual (e.g., human) comprising intravesicularly administering (for example via urethral catheterization) to the individual an effective amount of a composition comprising nanoparticles comprising a limus drug and an albumin, wherein the nanoparticles comprise a limus drug coated with albumin, and wherein the nanoparticles have an average particle size of no greater than about 200 nm (such as no greater than about 150 nm). In some embodiments, there is provided a method of treating bladder cancer in an individual (e.g., human) comprising intravesicularly administering (for example via urethral catheterization) to the individual an effective amount of a composition comprising nanoparticles comprising sirolimus and human albumin, wherein the nanoparticles comprise sirolimus coated with the human albumin, wherein the nanoparticles have an average particle size of no greater than about 150 nm (such as no greater than about 120 nm, for example about 100 nm), wherein the weight ratio of human albumin and sirolimus in the composition is about 9:1 or less (such as about 9:1 or about 8:1). In some embodiments, there is provided a method of treating bladder cancer in an individual (e.g., human) comprising intravesicularly administering (for example via urethral catheterization) to the individual an effective amount of a composition comprising Nab-sirolimus. In some embodiments, there is provided a method of treating bladder cancer in an individual (e.g., human) comprising intravesicularly administering (for example via urethral catheterization) to the individual an effective amount of Nab-sirolimus. In some embodiments, the limus drug (i.e., limus drug in the limus nanoparticle composition) is administered at a dose of about 5 mg to about 500 mg (including for example about 30 mg to about 400 mg, such as about 100 mg). In some embodiments, the limus nanoparticle composition is administered weekly. In some embodiments, the composition is administered weekly for 6 weeks, optionally followed by monthly maintenance thereafter. In some embodiments, the composition is administered with about 30 minutes to about 4 hours, such as about 1 hour to about 2 hours of retention in the bladder.

In some embodiments, there is provided a method of treating non-muscle invasive bladder cancer in an individual (e.g., human) comprising administering to the individual an effective amount of a composition comprising nanoparticles comprising an mTOR inhibitor (such as a limus drug). In some embodiments, there is provided a method of treating non-muscle invasive bladder cancer in an individual (e.g., human) comprising administering to the individual an effective amount of a composition comprising nanoparticles comprising a limus drug and an albumin. In some embodiments, there is provided a method of treating non-muscle invasive bladder cancer in an individual (e.g., human) comprising administering to the individual an effective amount of a composition comprising nanoparticles comprising a limus drug and an albumin, wherein the limus drug in the nanoparticles is coated with the albumin. In some embodiments, there is provided a method of treating non-muscle invasive bladder cancer in an individual (e.g., human) comprising administering to the individual an effective amount of a composition comprising nanoparticles comprising a limus drug and an albumin, wherein the nanoparticles have an average particle size of no greater than about 200 nm (such as no greater than about 150 nm). In some embodiments, there is provided a method of treating non-muscle invasive bladder cancer in an individual (e.g., human) comprising administering to the individual an effective amount of a composition comprising nanoparticles comprising a limus drug and an albumin, wherein the nanoparticles comprise a limus drug coated with albumin, and wherein the nanoparticles have an average particle size of no greater than about 200 nm (such as no greater than about 150 nm). In some embodiments, there is provided a method of treating non-muscle invasive bladder cancer in an individual (e.g., human) comprising administering to the individual an effective amount of a composition comprising nanoparticles comprising sirolimus and human albumin, wherein the nanoparticles comprise sirolimus coated with the human albumin, wherein the nanoparticles have an average particle size of no greater than about 150 nm (such as no greater than about 120 nm, for example about 100 nm), wherein the weight ratio of human albumin and sirolimus in the composition is about 9:1 or less (such as about 9:1 or about 8:1). In some embodiments, there is provided a method of treating non-muscle invasive bladder cancer in an individual (e.g., human) comprising administering to the individual an effective amount of a composition comprising Nab-sirolimus. In some embodiments, there is provided a method of treating non-muscle invasive bladder cancer in an individual (e.g., human) comprising administering to the individual an effective amount of Nab-sirolimus. In some embodiments, the limus drug is administered at a dose of about 5 mg to about 500 mg (including for example about 30 mg to about 400 mg, such as about 100 mg). In some embodiments, the limus nanoparticle composition is administered weekly. In some embodiments, the composition is administered weekly for 6 weeks, optionally followed by monthly maintenance thereafter.

In some embodiments, there is provided a method of treating non-muscle invasive bladder cancer in an individual (e.g., human) comprising intravesicularly administering (for example via urethral catheterization) to the individual an effective amount of a composition comprising nanoparticles comprising an mTOR inhibitor (such as a limus drug). In some embodiments, there is provided a method of treating non-muscle invasive bladder cancer in an individual (e.g., human) comprising intravesicularly administering (for example via urethral catheterization) to the individual an effective amount of a composition comprising nanoparticles comprising a limus drug and an albumin. In some embodiments, there is provided a method of treating non-muscle invasive bladder cancer in an individual (e.g., human) comprising intravesicularly administering (for example via urethral catheterization) to the individual an effective amount of a composition comprising nanoparticles comprising a limus drug and an albumin, wherein the limus drug in the nanoparticles is coated with the albumin. In some embodiments, there is provided a method of treating non-muscle invasive bladder cancer in an individual (e.g., human) comprising intravesicularly administering (for example via urethral catheterization) to the individual an effective amount of a composition comprising nanoparticles comprising a limus drug and an albumin, wherein the nanoparticles have an average particle size of no greater than about 200 nm (such as no greater than about 150 nm). In some embodiments, there is provided a method of treating non-muscle invasive bladder cancer in an individual (e.g., human) comprising intravesicularly administering (for example via urethral catheterization) to the individual an effective amount of a composition comprising nanoparticles comprising a limus drug and an albumin, wherein the nanoparticles comprise a limus drug coated with albumin, and wherein the nanoparticles have an average particle size of no greater than about 200 nm (such as no greater than about 150 nm). In some embodiments, there is provided a method of treating non-muscle invasive bladder cancer in an individual (e.g., human) comprising intravesicularly administering (for example via urethral catheterization) to the individual an effective amount of a composition comprising nanoparticles comprising sirolimus and human albumin, wherein the nanoparticles comprise sirolimus coated with the human albumin, wherein the nanoparticles have an average particle size of no greater than about 150 nm (such as no greater than about 120 nm, for example about 100 nm), wherein the weight ratio of human albumin and sirolimus in the composition is about 9:1 or less (such as about 9:1 or about 8:1). In some embodiments, there is provided a method of treating non-muscle invasive bladder cancer in an individual (e.g., human) comprising intravesicularly administering (for example via urethral catheterization) to the individual an effective amount of a composition comprising Nab-sirolimus. In some embodiments, there is provided a method of treating non-muscle invasive bladder cancer in an individual (e.g., human) comprising intravesicularly administering (for example via urethral catheterization) to the individual an effective amount of Nab-sirolimus. In some embodiments, the limus drug is administered at a dose of about 5 mg to about 500 mg (including for example about 30 mg to about 400 mg, such as about 100 mg). In some embodiments, the limus nanoparticle composition is administered weekly. In some embodiments, the composition is administered weekly for 6 weeks, optionally followed by monthly maintenance thereafter.

In some embodiments, there is provided a method of treating BCG-refractory bladder cancer in an individual (e.g., human) comprising intravesicularly administering (for example via urethral catheterization) to the individual an effective amount of a composition comprising nanoparticles comprising an mTOR inhibitor (such as a limus drug). In some embodiments, there is provided a method of treating BCG-refractory bladder cancer in an individual (e.g., human) comprising intravesicularly administering (for example via urethral catheterization) to the individual an effective amount of a composition comprising nanoparticles comprising a limus drug and an albumin. In some embodiments, there is provided a method of treating BCG-refractory bladder cancer in an individual (e.g., human) comprising intravesicularly administering (for example via urethral catheterization) to the individual an effective amount of a composition comprising nanoparticles comprising a limus drug and an albumin, wherein the limus drug in the nanoparticles is coated with the albumin. In some embodiments, there is provided a method of treating BCG-refractory bladder cancer in an individual (e.g., human) comprising intravesicularly administering (for example via urethral catheterization) to the individual an effective amount of a composition comprising nanoparticles comprising a limus drug and an albumin, wherein the nanoparticles have an average particle size of no greater than about 200 nm (such as no greater than about 150 nm). In some embodiments, there is provided a method of treating BCG-refractory bladder cancer in an individual (e.g., human) comprising intravesicularly administering (for example via urethral catheterization) to the individual an effective amount of a composition comprising nanoparticles comprising a limus drug and an albumin, wherein the nanoparticles comprise a limus drug coated with albumin, and wherein the nanoparticles have an average particle size of no greater than about 200 nm (such as no greater than about 150 nm). In some embodiments, there is provided a method of treating BCG-refractory bladder cancer in an individual (e.g., human) comprising intravesicularly administering (for example via urethral catheterization) to the individual an effective amount of a composition comprising nanoparticles comprising sirolimus and human albumin, wherein the nanoparticles comprise sirolimus coated with the human albumin, wherein the nanoparticles have an average particle size of no greater than about 150 nm (such as no greater than about 120 nm, for example about 100 nm), wherein the weight ratio of human albumin and sirolimus in the composition is about 9:1 or less (such as about 9:1 or about 8:1). In some embodiments, there is provided a method of treating BCG-refractory bladder cancer in an individual (e.g., human) comprising intravesicularly administering (for example via urethral catheterization) to the individual an effective amount of a composition comprising Nab-sirolimus. In some embodiments, there is provided a method of treating BCG-refractory bladder cancer in an individual (e.g., human) comprising intravesicularly administering (for example via urethral catheterization) to the individual an effective amount of Nab-sirolimus. In some embodiments, the limus drug is administered at a dose of about 5 mg to about 500 mg (including for example about 30 mg to about 400 mg, such as about 100 mg). In some embodiments, the limus nanoparticle composition is administered weekly. In some embodiments, the composition is administered weekly for 6 weeks, optionally followed by monthly maintenance thereafter.

In some embodiments, there is provided a method of treating metastatic bladder cancer (such as metastatic urothelial carcinoma) in an individual, comprising intravenously administering to the individual an effective amount of a composition comprising nanoparticles comprising an mTOR inhibitor (such as a limus drug). In some embodiments, there is provided a method of treating metastatic bladder cancer (such as metastatic urothelial carcinoma) in an individual, comprising intravenously administering to the individual an effective amount of a composition comprising nanoparticles comprising a limus drug and an albumin. In some embodiments, there is provided a method of treating metastatic bladder cancer (such as metastatic urothelial carcinoma) in an individual, comprising intravenously administering to the individual an effective amount of a composition comprising nanoparticles comprising a limus drug coated with albumin. In some embodiments, there is provided a method of treating metastatic bladder cancer (such as metastatic urothelial carcinoma) in an individual, comprising intravenously administering to the individual an effective amount of a composition comprising nanoparticles comprising a limus drug and albumin and having an average diameter of no greater than about 200 nm. In some embodiments, there is provided a method of treating metastatic bladder cancer (such as metastatic urothelial carcinoma) in an individual, comprising intravenously administering to the individual an effective amount of a composition comprising nanoparticles comprising a limus drug coated with albumin and having an average diameter of no greater than about 200 nm. In some embodiments, there is provided a method of treating metastatic bladder cancer (such as metastatic urothelial carcinoma) in an individual, comprising intravenously administering to the individual an effective amount of a composition comprising nanoparticles comprising sirolimus coated with human albumin and having an average diameter of no greater than about 150 (such as no greater than about 120 nm, for example about 100 nm), wherein the weight ratio of human albumin and sirolimus in the composition is about 9:1 or less (such as about 9:1 or about 8:1). In some embodiments, there is provided a method of treating metastatic bladder cancer (such as metastatic urothelial carcinoma) in an individual, comprising intravenously administering to the individual an effective amount of a composition comprising Nab-sirolimus. In some embodiments, there is provided a method of treating metastatic bladder cancer (such as metastatic urothelial carcinoma) in an individual, comprising intravenously administering to the individual an effective amount of Nab-sirolimus. In some embodiments, the treatment is second line treatment.

In some embodiments, there is provided a method of treating a platinum-refractory bladder cancer (such as metastatic platinum-refractory bladder cancer, for example metastatic platinum-refractory urothelial carcinoma) in an individual, comprising administering (such as intravenously administering) to the individual an effective amount of a composition comprising nanoparticles comprising an mTOR inhibitor (such as a limus drug). In some embodiments, there is provided a method of treating a platinum-refractory bladder cancer (such as metastatic platinum-refractory bladder cancer, for example metastatic platinum-refractory urothelial carcinoma) in an individual, comprising administering (such as intravenously administering) to the individual an effective amount of a composition comprising nanoparticles comprising a limus drug and an albumin. In some embodiments, there is provided a method of treating platinum-refractory bladder cancer (such as metastatic platinum-refractory bladder cancer, for example metastatic platinum-refractory urothelial carcinoma) in an individual, comprising administering (such as intravenously administering) to the individual an effective amount of a composition comprising nanoparticles comprising a limus drug coated with albumin. In some embodiments, there is provided a method of treating platinum-refractory bladder cancer (such as metastatic platinum-refractory bladder cancer, for example metastatic platinum-refractory urothelial carcinoma) in an individual, comprising administering (such as intravenously administering) to the individual an effective amount of a composition comprising nanoparticles comprising a limus drug and albumin and having an average diameter of no greater than about 200 nm. In some embodiments, there is provided a method of treating platinum-refractory bladder cancer (such as metastatic platinum-refractory bladder cancer, for example metastatic platinum-refractory urothelial carcinoma) in an individual, comprising administering (such as intravenously administering) to the individual an effective amount of a composition comprising nanoparticles comprising a limus drug coated with albumin and having an average diameter of no greater than about 200 nm. In some embodiments, there is provided a method of treating platinum-refractory bladder cancer (such as metastatic platinum-refractory bladder cancer, for example metastatic platinum-refractory urothelial carcinoma) in an individual, comprising administering (such as intravenously administering) to the individual an effective amount of a composition comprising nanoparticles comprising sirolimus coated with human albumin and having an average diameter of no greater than about 200 nm, wherein the weight ratio of human albumin and sirolimus in the composition is about 9:1 or less (such as about 9:1 or about 8:1). In some embodiments, there is provided a method of treating platinum-refractory bladder cancer (such as metastatic platinum-refractory bladder cancer, for example metastatic platinum-refractory urothelial carcinoma) in an individual, comprising administering (such as intravenously administering) to the individual an effective amount of a composition comprising Nab-sirolimus. In some embodiments, there is provided a method of treating platinum-refractory bladder cancer (such as metastatic platinum-refractory bladder cancer, for example metastatic platinum-refractory urothelial carcinoma) in an individual, comprising administering (such as intravenously administering) to the individual an effective amount of Nab-sirolimus.

The methods described herein are useful for various aspects of bladder cancer treatment. In some embodiments, there is provided a method of inhibiting bladder cancer cell proliferation (such as bladder cancer tumor growth) in an individual, comprising administering to the individual an effective amount of a composition comprising nanoparticles comprising a limus drug and an albumin. In some embodiments, at least about 10% (including for example at least about any of 20%, 30%, 40%, 60%, 70%, 80%, 90%, or 100%) cell proliferation is inhibited. In some embodiments, the limus drug is sirolimus. In some embodiments, the limus drug in the nanoparticle in the composition is administered by intravenous administration. In some embodiments, the limus drug in the nanoparticle in the composition is administered by intravesicular administration. In some embodiments, the composition comprises nanoparticles comprising a limus drug coated with albumin. In some embodiments, the composition comprises nanoparticles having an average diameter of no greater than about 200 nm. In some embodiments, the composition comprises nanoparticles comprising a limus drug coated with albumin, wherein the nanoparticles have an average diameter of no greater than about 200 nm. In some embodiments, the composition comprises nanoparticles comprising sirolimus coated with human albumin, wherein the nanoparticles have an average diameter of no greater than about 150 nm (such as no greater than about 120 nm, for example about 100 nm), wherein the weight ratio of human albumin and sirolimus in the composition is about 9:1 or less (such as about 9:1 or about 8:1). In some embodiments, the composition comprises Nab-sirolimus. In some embodiments, the composition is Nab-sirolimus.

In some embodiments, there is provided a method of preventing local recurrence (e.g., recurrence of tumor after resection) in an individual having bladder cancer, comprising administering to the individual an effective amount of a composition comprising nanoparticles comprising a limus drug and an albumin. In some embodiments, at least about 10% (including for example at least about any of 20%, 30%, 40%, 60%, 70%, 80%, 90%, or 100%) metastasis is inhibited. In some embodiments, the limus drug is sirolimus. In some embodiments, the limus drug in the nanoparticle in the composition is administered by intravenous administration. In some embodiments, the limus drug in the nanoparticle in the composition is administered by intravesicular administration. In some embodiments, the composition comprises nanoparticles comprising a limus drug coated with albumin. In some embodiments, the composition comprises nanoparticles having an average diameter of no greater than about 200 nm. In some embodiments, the composition comprises nanoparticles comprising a limus drug coated with albumin, wherein the nanoparticles have an average diameter of no greater than about 200 nm. In some embodiments, the composition comprises nanoparticles comprising sirolimus coated with human albumin, wherein the nanoparticles have an average diameter of no greater than about 150 nm (such as no greater than about 120 nm, for example about 100 nm), wherein the weight ratio of human albumin and sirolimus in the composition is about 9:1 or less (such as about 9:1 or about 8:1). In some embodiments, the composition comprises Nab-sirolimus. In some embodiments, the composition is Nab-sirolimus.

In some embodiments, there is provided a method of inhibiting bladder cancer tumor metastasis in an individual, comprising administering to the individual an effective amount of a composition comprising nanoparticles comprising a limus drug and an albumin. In some embodiments, at least about 10% (including for example at least about any of 20%, 30%, 40%, 60%, 70%, 80%, 90%, or 100%) metastasis is inhibited. In some embodiments, a method of inhibiting metastasis to lymph node is provided. In some embodiments, a method of inhibiting metastasis to the lung is provided. In some embodiments, the limus drug is sirolimus. In some embodiments, the limus drug in the nanoparticle in the composition is administered by intravenous administration. In some embodiments, the limus drug in the nanoparticle in the composition is administered by intravesicular administration. In some embodiments, the composition comprises nanoparticles comprising a limus drug coated with albumin. In some embodiments, the composition comprises nanoparticles having an average diameter of no greater than about 200 nm. In some embodiments, the composition comprises nanoparticles comprising a limus drug coated with albumin, wherein the nanoparticles have an average diameter of no greater than about 200 nm. In some embodiments, the composition comprises nanoparticles comprising sirolimus coated with human albumin, wherein the nanoparticles have an average diameter of no greater than about 150 nm (such as no greater than about 120 nm, for example about 100 nm), wherein the weight ratio of human albumin and sirolimus in the composition is about 9:1 or less (such as about 9:1 or about 8:1). In some embodiments, the composition comprises Nab-sirolimus. In some embodiments, the composition is Nab-sirolimus.

In some embodiments, there is provided a method of reducing (such as eradiating) preexisting bladder cancer tumor metastasis (such as pulmonary metastasis or metastasis to the lymph node) in an individual, comprising administering to the individual an effective amount of a composition comprising nanoparticles comprising a limus drug and an albumin. In some embodiments, at least about 10% (including for example at least about any of 20%, 30%, 40%, 60%, 70%, 80%, 90%, or 100%) metastasis is reduced. In some embodiments, a method of reducing metastasis to lymph node is provided. In some embodiments, a method of reducing metastasis to the lung is provided. In some embodiments, the limus drug is sirolimus. In some embodiments, the limus drug in the nanoparticle in the composition is administered by intravenous administration. In some embodiments, the limus drug in the nanoparticle in the composition is administered by intravesicular administration. In some embodiments, the composition comprises nanoparticles comprising a limus drug coated with albumin. In some embodiments, the composition comprises nanoparticles having an average diameter of no greater than about 200 nm. In some embodiments, the composition comprises nanoparticles comprising a limus drug coated with albumin, wherein the nanoparticles have an average diameter of no greater than about 200 nm. In some embodiments, the composition comprises nanoparticles comprising sirolimus coated with human albumin, wherein the nanoparticles have an average diameter of no greater than about 150 nm (such as no greater than about 120 nm, for example about 100 nm), wherein the weight ratio of human albumin and sirolimus in the composition is about 9:1 or less (such as about 9:1 or about 8:1). In some embodiments, the composition comprises Nab-sirolimus. In some embodiments, the composition is Nab-sirolimus.

In some embodiments, there is provided a method of reducing incidence or burden of preexisting bladder cancer tumor metastasis (such as pulmonary metastasis or metastasis to the lymph node) in an individual, comprising administering to the individual an effective amount of a composition comprising nanoparticles comprising a limus drug and an albumin. In some embodiments, the limus drug is sirolimus. In some embodiments, the limus drug in the nanoparticle in the composition is administered by intravenous administration. In some embodiments, the limus drug in the nanoparticle in the composition is administered by intravesicular administration. In some embodiments, the composition comprises nanoparticles comprising a limus drug coated with albumin. In some embodiments, the composition comprises nanoparticles having an average diameter of no greater than about 200 nm. In some embodiments, the composition comprises nanoparticles comprising a limus drug coated with albumin, wherein the nanoparticles have an average diameter of no greater than about 200 nm. In some embodiments, the composition comprises nanoparticles comprising sirolimus coated with human albumin, wherein the nanoparticles have an average diameter of no greater than about 150 nm (such as no greater than about 120 nm, for example about 100 nm), wherein the weight ratio of human albumin and sirolimus in the composition is about 9:1 or less (such as about 9:1 or about 8:1). In some embodiments, the composition comprises Nab-sirolimus. In some embodiments, the composition is Nab-sirolimus.

In some embodiments, there is provided a method of reducing bladder cancer tumor size in an individual, comprising administering to the individual an effective amount of a composition comprising nanoparticles comprising a limus drug and an albumin. In some embodiments, the tumor size is reduced at least about 10% (including for example at least about any of 20%, 30%, 40%, 60%, 70%, 80%, 90%, or 100%). In some embodiments, the limus drug is sirolimus. In some embodiments, the limus drug in the nanoparticle in the composition is administered by intravenous administration. In some embodiments, the limus drug in the nanoparticle in the composition is administered by intravesicular administration. In some embodiments, the composition comprises nanoparticles comprising a limus drug coated with albumin. In some embodiments, the composition comprises nanoparticles having an average diameter of no greater than about 200 nm. In some embodiments, the composition comprises nanoparticles comprising a limus drug coated with albumin, wherein the nanoparticles have an average diameter of no greater than about 200 nm. In some embodiments, the composition comprises nanoparticles comprising sirolimus coated with human albumin, wherein the nanoparticles have an average diameter of no greater than about 150 nm (such as no greater than about 120 nm, for example about 100 nm), wherein the weight ratio of human albumin and sirolimus in the composition is about 9:1 or less (such as about 9:1 or about 8:1).

In some embodiments, there is provided a method of prolonging time to disease progression of bladder cancer in an individual, comprising administering to the individual an effective amount of a composition comprising nanoparticles comprising a limus drug and an albumin. In some embodiments, the method prolongs the time to disease progression by at least any of 1, 2, 3, 4, 5, 6, 7, 8, 9, 10, 11, or 12 weeks. In some embodiments, the limus drug is sirolimus. In some embodiments, the limus drug in the nanoparticle in the composition is administered by intravenous administration. In some embodiments, the limus drug in the nanoparticle in the composition is administered by intravesicular administration. In some embodiments, the composition comprises nanoparticles comprising a limus drug coated with albumin. In some embodiments, the composition comprises nanoparticles having an average diameter of no greater than about 200 nm. In some embodiments, the composition comprises nanoparticles comprising a limus drug coated with albumin, wherein the nanoparticles have an average diameter of no greater than about 200 nm. In some embodiments, the composition comprises nanoparticles comprising sirolimus coated with human albumin, wherein the nanoparticles have an average diameter of no greater than about 150 nm (such as no greater than about 120 nm, for example about 100 nm), wherein the weight ratio of human albumin and sirolimus in the composition is about 9:1 or less (such as about 9:1 or about 8:1). In some embodiments, the composition comprises Nab-sirolimus. In some embodiments, the composition is Nab-sirolimus.

In some embodiments, there is provided a method of prolonging survival of an individual having bladder cancer, comprising administering to the individual an effective amount of a composition comprising nanoparticles comprising a limus drug and an albumin. In some embodiments, the method prolongs the survival of the individual by at least any of 1, 2, 3, 4, 5, 6, 7, 8, 9, 10, 11, 12, 18, or 24 month. In some embodiments, the limus drug is sirolimus. In some embodiments, the limus drug in the nanoparticle in the composition is administered by intravenous administration. In some embodiments, the limus drug in the nanoparticle in the composition is administered by intravesicular administration. In some embodiments, the composition comprises nanoparticles comprising a limus drug coated with albumin. In some embodiments, the composition comprises nanoparticles having an average diameter of no greater than about 200 nm. In some embodiments, the composition comprises nanoparticles comprising a limus drug coated with albumin, wherein the nanoparticles have an average diameter of no greater than about 200 nm. In some embodiments, the composition comprises nanoparticles comprising sirolimus coated with human albumin, wherein the nanoparticles have an average diameter of no greater than about 150 nm (such as no greater than about 120 nm, for example about 100 nm), wherein the weight ratio of human albumin and sirolimus in the composition is about 9:1 or less (such as about 9:1 or about 8:1). In some embodiments, the composition comprises Nab-sirolimus. In some embodiments, the composition is Nab-sirolimus.

In some embodiments, there is provided a method of alleviating one or more symptoms in an individual having bladder cancer, comprising administering to the individual an effective amount of a composition comprising nanoparticles comprising a limus drug and an albumin. In some embodiments, the limus drug in the nanoparticle in the composition is administered by intravenous administration. In some embodiments, the limus drug in the nanoparticle in the composition is administered by intravesicular administration. In some embodiments, the composition comprises nanoparticles comprising a limus drug coated with albumin. In some embodiments, the composition comprises nanoparticles having an average diameter of no greater than about 200 nm. In some embodiments, the composition comprises nanoparticles comprising a limus drug coated with albumin, wherein the nanoparticles have an average diameter of no greater than about 200 nm. In some embodiments, the composition comprises nanoparticles comprising sirolimus coated with human albumin, wherein the nanoparticles have an average diameter of no greater than about 150 nm (such as no greater than about 120 nm, for example about 100 nm), wherein the weight ratio of human albumin and sirolimus in the composition is about 9:1 or less (such as about 9:1 or about 8:1). In some embodiments, the composition comprises Nab-sirolimus. In some embodiments, the composition is Nab-sirolimus.

In some embodiments, there is provided a method of suppression the progression of CIS (carcinoma in situ) lesions in an individual having bladder cancer, comprising administering to the individual an effective amount of a composition comprising nanoparticles comprising a limus drug and an albumin. In some embodiments, the limus drug in the nanoparticle in the composition is administered by intravenous administration. In some embodiments, the limus drug in the nanoparticle in the composition is administered by intravesicular administration. In some embodiments, the composition comprises nanoparticles comprising a limus drug coated with albumin. In some embodiments, the composition comprises nanoparticles having an average diameter of no greater than about 200 nm. In some embodiments, the composition comprises nanoparticles comprising a limus drug coated with albumin, wherein the nanoparticles have an average diameter of no greater than about 200 nm. In some embodiments, the composition comprises nanoparticles comprising sirolimus coated with human albumin, wherein the nanoparticles have an average diameter of no greater than about 150 nm (such as no greater than about 120 nm, for example about 100 nm), wherein the weight ratio of human albumin and sirolimus in the composition is about 9:1 or less (such as about 9:1 or about 8:1). In some embodiments, the composition comprises Nab-sirolimus. In some embodiments, the composition is Nab-sirolimus.

Also provided are pharmaceutical compositions comprising nanoparticles comprising an mTOR inhibitor (such as limus drug, for example sirolimus) for use in any of the methods of treating bladder cancer described herein. In some embodiments, the compositions comprise nanoparticles comprising an mTOR inhibitor (such as limus drug, for example sirolimus) and albumin (such as human albumin).

Methods of Combination Therapy

The present invention also provides combination therapy methods for treating bladder cancer. Thus, in some embodiments, the individual being treated with the mTOR nanoparticle composition is also subjected to a second therapy. In some embodiments, the second therapy is surgery, radiation, immunotherapy, and/or chemotherapy. It is understood that reference to and description of methods of treating bladder cancer above is exemplary and that the description applies equally to and includes methods of treating bladder cancer using combination therapy.

In some embodiments, the method comprises administering the mTOR inhibitor nanoparticle composition (such as a limus nanoparticle composition) and at least another agent. In some embodiments, the nanoparticle composition and the other agent (including the specific therapeutic agents described herein) are administered simultaneously. When the drugs are administered simultaneously, the drug in the nanoparticles and the other agent may be contained in the same composition (e.g., a composition comprising both the nanoparticles and the other agent) or in separate compositions (e.g., the nanoparticles are contained in one composition and the other agent is contained in another composition). In some embodiments, the nanoparticle composition and the other agent are administered sequentially. Either the nanoparticle composition or the other agent may be administered first. The nanoparticle composition and the other agent are contained in separate compositions, which may be contained in the same or different packages. In some embodiments, the administration of the nanoparticle composition and the other agent are concurrent, i.e., the administration period of the nanoparticle composition and that of the other agent overlap with each other.

In some embodiments, the method comprises administration of an mTOR nanoparticle composition (such as a limus nanoparticle composition) in combination with an immunotherapy (such as administration of an immunotherapeutic agent). Suitable immnunotherapeutic agents that can be combined with the mTOR nanoparticle composition (such as a limus nanoparticle composition) include, but are not limited to, BCG, interferons, and other immune stimulatory cytokines.

Thus, the present application in some embodiments provides a method of treating bladder cancer in an individual (e.g., human) comprising administering (such as intravesicularly administering (for example via urethral catheterization)) to the individual (a) an effective amount of a composition comprising nanoparticles comprising an mTOR inhibitor (such as a limus drug); and (b) an immunotherapeutic agent. Thus, the present application in some embodiments provides a method of treating bladder cancer in an individual (e.g., human) comprising administering (such as intravesicularly administering (for example via urethral catheterization)) to the individual (a) an effective amount of a composition comprising nanoparticles comprising a limus drug and an albumin; and (b) an immunotherapeutic agent. In some embodiments, there is provided a method of treating bladder cancer in an individual (e.g., human) comprising administering (such as intravesicularly administering (for example via urethral catheterization)) to the individual (a) an effective amount of a composition comprising nanoparticles comprising a limus drug and an albumin, wherein the limus drug in the nanoparticles is coated with the albumin; and (b) an immunotherapeutic agent. In some embodiments, there is provided a method of treating bladder cancer in an individual (e.g., human) comprising administering (such as intravesicularly administering (for example via urethral catheterization)) to the individual (a) an effective amount of a composition comprising nanoparticles comprising a limus drug and an albumin, wherein the nanoparticles have an average particle size of no greater than about 200 nm (such as no greater than about 150 nm); and (b) an immunotherapeutic agent. In some embodiments, there is provided a method of treating bladder cancer in an individual (e.g., human) comprising administering (such as intravesicularly administering (for example via urethral catheterization)) to the individual an effective amount of a composition comprising nanoparticles comprising a limus drug and an albumin, wherein the nanoparticles comprise a limus drug coated with albumin, and wherein the nanoparticles have an average particle size of no greater than about 200 nm (such as no greater than about 150 nm); and (b) an immunotherapeutic agent. In some embodiments, there is provided a method of treating bladder cancer in an individual (e.g., human) comprising administering (such as intravesicularly administering (for example via urethral catheterization)) to the individual (a) an effective amount of a composition comprising nanoparticles comprising sirolimus and human albumin, wherein the nanoparticles comprise sirolimus coated with the human albumin, wherein the nanoparticles have an average particle size of no greater than about 150 nm (such as no greater than about 120 nm, for example about 100 nm), wherein the weight ratio of human albumin and sirolimus in the composition is about 9:1 or less (such as about 9:1 or about 8:1); and (b) an immunotherapeutic agent. In some embodiments, there is provided a method of treating bladder cancer in an individual (e.g., human) comprising administering (such as intravesicularly administering (for example via urethral catheterization)) to the individual (a) an effective amount of a composition comprising Nab-sirolimus; and (b) an immunotherapeutic agent. In some embodiments, there is provided a method of treating bladder cancer in an individual (e.g., human) comprising administering (such as intravesicularly administering (for example via urethral catheterization)) administering to the individual (a) an effective amount of Nab-sirolimus; and (b) an immunotherapeutic agent. In some embodiments, the bladder cancer is non-muscle invasive bladder cancer. In some embodiments, the bladder cancer is BCG-refractory bladder cancer. In some embodiments, the bladder cancer is BCG-refractory non-muscle invasive bladder cancer.

In some embodiments, the other agent is BCG (Bacillus Calmette-Guérin), a live attenuated form of *Mycobacterium bovis*. In some embodiments, there is provided a method of treating bladder cancer in an individual (e.g., human) comprising administering (such as intravesicularly administering (for example via urethral catheterization)) to the individual (a) an effective amount of a composition comprising nanoparticles comprising an mTOR inhibitor (such as a limus drug); and (b) an effective amount of BCG. In some embodiments, there is provided a method of treating bladder cancer in an individual (e.g., human) comprising administering (such as intravesicularly administering (for example via urethral catheterization)) to the individual (a) an effective amount of a composition comprising nanoparticles comprising a limus drug and an albumin; and (b) an effective amount of BCG. In some embodiments, there is provided a method of treating bladder cancer in an individual (e.g., human) comprising administering (such as intravesicularly administering (for example via urethral catheterization)) to the individual (a) an effective amount of a composition comprising nanoparticles comprising a limus drug and an albumin, wherein the limus drug in the nanoparticles is coated with the albumin; and (b) an effective amount of BCG. In some embodiments, there is provided a method of treating bladder cancer in an individual (e.g., human) comprising administering (such as intravesicularly administering (for example via urethral catheterization)) to the individual (a) an effective amount of a composition comprising nanoparticles comprising a limus drug and an albumin, wherein the nanoparticles have an average particle size of no greater than about 200 nm (such as no greater than about 150 nm); and (b) an effective amount of BCG. In some embodiments, there is provided a method of treating bladder cancer in an individual (e.g., human) comprising administering (such as intravesicularly administering (for example via urethral catheterization)) to the individual an effective amount of a composition comprising nanoparticles comprising a limus drug and an albumin, wherein the nanoparticles comprise a limus drug coated with albumin, and wherein the nanoparticles have an average particle size of no greater than about 200 nm (such as no greater than about 150 nm); and (b) an effective amount of BCG. In some embodiments, there is provided a method of treating bladder cancer in an individual (e.g., human) comprising administering (such as intravesicularly administering (for example via urethral catheterization)) to the individual (a) an effective amount of a composition comprising nanoparticles comprising sirolimus and human albumin, wherein the nanoparticles comprise sirolimus coated with the human albumin, wherein the nanoparticles have an average particle size of no greater than about 150 nm (such as no greater than about 120 nm, for example about 100 nm), wherein the weight ratio of human albumin and sirolimus in the composition is about 9:1 or less (such as about 9:1 or about 8:1); and (b) an effective amount of BCG. In some embodiments, there is provided a method of treating bladder cancer in an individual (e.g., human) comprising administering (such as intravesicularly administering (for example via urethral catheterization)) to the individual (a) an effective amount of a composition comprising Nab-sirolimus; and (b) an effective amount of BCG. In some embodiments, there is provided a method of treating bladder cancer in an individual (e.g., human) comprising administering (such as intravesicularly administering (for example via urethral catheterization)) administering to the individual (a) an effective amount of Nab-sirolimus; and (b) an effective amount of BCG. In some embodiments, the bladder cancer is non-muscle invasive bladder cancer. In some embodiments, the bladder cancer is BCG-refractory bladder cancer. In some embodiments, the bladder cancer is BCG-refractory non-muscle invasive bladder cancer.

In some embodiments, there is provided a method of treating bladder cancer (such as non-muscle invasive bladder cancer) in an individual (e.g., human) comprising intravesicularly administering (for example via urethral catheterization) to the individual (a) an effective amount of a composition comprising nanoparticles comprising a limus drug and an albumin, wherein the dose of the limus drug in the composition is about 5 mg to about 500 mg (such as about 30 mg to about 400 mg, for example about 100 mg); and (b) an effective amount of BCG, wherein the dose of BCG is about 8 mg to about 100 mg (such as about 25 mg to about 85 mg, for example about 80 mg). In some embodiments, there is provided a method of treating bladder cancer (such as non-muscle invasive bladder cancer) in an individual (e.g., human) comprising administering (such as intravesicularly administering (for example via urethral catheterization)) to the individual (a) an effective amount of a composition comprising nanoparticles comprising a limus drug and an albumin, wherein the limus drug in the nanoparticles is coated with the albumin, wherein the dose of the limus drug in the composition is about 5 mg to about 500 mg (such as about 30 mg to about 400 mg, for example about 100 mg); and (b) an effective amount of BCG, wherein the dose of BCG is about 8 mg to about 100 mg (such as about 25 mg to about 85 mg, for example about 80 mg). In some embodiments, there is provided a method of treating bladder cancer (such as non-muscle invasive bladder cancer) in an individual (e.g., human) comprising administering (such as intravesicularly administering (for example via urethral catheterization)) to the individual (a) an effective amount of a composition comprising nanoparticles comprising a limus drug and an albumin, wherein the nanoparticles have an average particle size of no greater than about 200 nm (such as no greater than about 150 nm), wherein the dose of the limus drug in the composition is about 5 mg to about 500 mg (such as about 30 mg to about 400 mg, for example about 100 mg); and (b) an effective amount of BCG, wherein the dose of BCG is about 8 mg to about 100 mg (such as about 25 mg to about 85 mg, for example about 80 mg). In some embodiments, there is provided a method of treating bladder cancer (such as non-muscle invasive bladder cancer) in an individual (e.g., human) comprising administering (such as intravesicularly administering (for example via urethral catheterization)) to the individual an effective amount of a composition comprising nanoparticles comprising a limus drug and an albumin, wherein the nanoparticles comprise a limus drug coated with albumin, and wherein the nanoparticles have an average particle size of no greater than about 200 nm (such as no greater than about 150 nm), wherein the dose of the limus drug in the composition is about 5 mg to about 500 mg (such as about 30 mg to about 400 mg, for example about 100 mg); and (b) an effective amount of BCG, wherein the dose of BCG is about 8 mg to about 100 mg (such as about 25 mg to about 85 mg, for example about 80 mg). In some embodiments, there is provided a method of treating bladder cancer (such as non-muscle invasive bladder cancer) in an individual (e.g., human) comprising administering (such as intravesicularly administering (for example via urethral catheterization)) to the individual (a) an effective amount of a composition comprising nanoparticles comprising sirolimus and human albumin, wherein the nanoparticles comprise sirolimus coated with the human albumin, wherein the nanoparticles have an average particle size of no greater than about 150 nm (such as no greater than about 120 nm, for example about 100 nm), wherein the weight ratio of human albumin and sirolimus in the composition is about 9:1 or less (such as about 9:1 or about 8:1) wherein the dose of the sirolimus in the composition is about 5 mg to about 500 mg (such as about 30 mg to about 400 mg, for example about 100 mg); and (b) an effective amount of BCG, wherein the dose of BCG is about 8 mg to about 100 mg (such as about 25 mg to about 85 mg, for example about 80 mg). In some embodiments, there is provided a method of treating bladder cancer (such as non-muscle invasive bladder cancer) in an individual (e.g., human) comprising administering (such as intravesicularly administering (for example via urethral catheterization)) to the individual (a) an effective amount of a composition comprising Nab-sirolimus, wherein the dose of the limus drug in the composition is about 5 mg to about 500 mg (such as about 30 mg to about 400 mg, for example about 100 mg); and (b) an effective amount of BCG, wherein the dose of BCG is about 8 mg to about 100 mg (such as about 25 mg to about 85 mg, for example about 80 mg). In some embodiments, there is provided a method of treating bladder cancer (such as non-muscle invasive bladder cancer) in an individual (e.g., human) comprising administering (such as intravesicularly administering (for example via urethral catheterization)) administering to the individual (a) an effective amount of Nab-sirolimus, wherein the dose of the limus drug in the composition is about 5 mg to about 500 mg (such as about 30 mg to about 400 mg, for example about 100 mg); and (b) an effective amount of BCG, wherein the dose of BCG is about 8 mg to about 100 mg (such as about 25 mg to about 85 mg, for example about 80 mg). In some embodiments, the bladder cancer is non-muscle invasive bladder cancer. In some embodiments, the bladder cancer is BCG-refractory bladder cancer. In some embodiments, the bladder cancer is BCG-refractory non-muscle invasive bladder cancer.

In some embodiments, there is provided a method of treating non-muscle invasive bladder cancer in an individual (e.g., human) comprising intravesicularly administering (for example via urethral catheterization) to the individual (a) an effective amount of a composition comprising nanoparticles comprising sirolimus and human albumin, wherein the nanoparticles comprise sirolimus coated with the human albumin, wherein the nanoparticles have an average particle size of no greater than about 150 nm (such as no greater than about 120 nm, for example about 100 nm), wherein the weight ratio of human albumin and sirolimus in the composition is about 9:1 or less (such as about 9:1 or about 8:1), wherein the dose of the sirolimus in the composition is about 5 mg to about 500 mg (such as about 30 mg to about 400 mg, for example about 100 mg) weekly; and (b) an effective amount of BCG, wherein the dose of BCG is about 8 mg to about 100 mg (such as about 25 mg to about 85 mg, for example about 80 mg) weekly. In some embodiments, there is provided a method of treating bladder cancer (such as non-muscle invasive bladder cancer) in an individual (e.g., human) comprising administering (such as intravesicularly administering (for example via urethral catheterization)) to the individual (a) an effective amount of a composition comprising Nab-sirolimus, wherein the dose of the limus drug in the composition is about 5 mg to about 500 mg (such as about 30 mg to about 400 mg, for example about 100 mg) weekly; and (b) an effective amount of BCG, wherein the dose of BCG is about 8 mg to about 100 mg (such as about 25 mg to about 85 mg, for example about 80 mg) weekly. In some embodiments, there is provided a method of treating bladder cancer (such as non-muscle invasive bladder cancer) in an individual (e.g., human) comprising administering (such as intravesicularly administering (for example via urethral catheterization)) administering to the individual (a) an effective amount of Nab-sirolimus, wherein the dose of the limus drug in the composition is about 5 mg to about 500 mg (such as about 30 mg to about 400 mg, for example about 100 mg) weekly; and (b) an effective amount of BCG, wherein the dose of BCG is about 8 mg to about 100 mg (such as about 25 mg to about 85 mg, for example about 80 mg) weekly. In some embodiments, the nanoparticle composition and/or BCG are provided in a volume of about 20-ml to about 150 ml (such as about 50 ml). In some embodiments, the nanoparticle composition and/or BCG are retained in the bladder for about 30 minutes to about 4 hours (such as about 30 minutes).

In some embodiments, the methods of combination therapy described herein comprise administration of an interferon, such as interferon α, with or without BCG.

Thus, for example, in some embodiments, there is provided a method of treating bladder cancer in an individual (e.g., human) comprising administering (such as intravesicularly administering (for example via urethral catheterization)) to the individual (a) an effective amount of a composition comprising nanoparticles comprising an mTOR inhibitor (such as a limus drug); (b) an effective amount of an interferon (such as interferon α). In some embodiments, there is provided a method of treating bladder cancer in an individual (e.g., human) comprising administering (such as intravesicularly administering (for example via urethral catheterization)) to the individual (a) an effective amount of a composition comprising nanoparticles comprising a limus drug and an albumin; (b) an effective amount of an interferon (such as interferon α). In some embodiments, there is provided a method of treating bladder cancer in an individual (e.g., human) comprising administering (such as intravesicularly administering (for example via urethral catheterization)) to the individual (a) an effective amount of a composition comprising nanoparticles comprising a limus drug and an albumin, wherein the limus drug in the nanoparticles is coated with the albumin; (b) an effective amount of an interferon (such as interferon α). In some embodiments, there is provided a method of treating bladder cancer in an individual (e.g., human) comprising administering (such as intravesicularly administering (for example via urethral catheterization)) to the individual (a) an effective amount of a composition comprising nanoparticles comprising a limus drug and an albumin, wherein the nanoparticles have an average particle size of no greater than about 200 nm (such as no greater than about 150 nm); (b) an effective amount of an interferon (such as interferon α). In some embodiments, there is provided a method of treating bladder cancer in an individual (e.g., human) comprising administering (such as intravesicularly administering (for example via urethral catheterization)) to the individual an effective amount of a composition comprising nanoparticles comprising a limus drug and an albumin, wherein the nanoparticles comprise a limus drug coated with albumin, and wherein the nanoparticles have an average particle size of no greater than about 200 nm (such as no greater than about 150 nm); (b) an effective amount of an interferon (such as interferon α). In some embodiments, there is provided a method of treating bladder cancer in an individual (e.g., human) comprising administering (such as intravesicularly administering (for example via urethral catheterization)) to the individual (a) an effective amount of a composition comprising nanoparticles comprising sirolimus and human albumin, wherein the nanoparticles comprise sirolimus coated with the human albumin, wherein the nanoparticles have an average particle size of no greater than about 150 nm (such as no greater than about 120 nm, for example about 100 nm), wherein the weight ratio of human albumin and sirolimus in the composition is about 9:1 or less (such as about 9:1 or about 8:1); (b) an effective amount of an interferon (such as interferon α). In some embodiments, there is provided a method of treating bladder cancer in an individual (e.g., human) comprising administering (such as intravesicularly administering (for example via urethral catheterization)) to the individual (a) an effective amount of a composition comprising Nab-sirolimus; (b) an effective amount of an interferon (such as interferon α). In some embodiments, there is provided a method of treating bladder cancer in an individual (e.g., human) comprising administering (such as intravesicularly administering (for example via urethral catheterization)) administering to the individual (a) an effective amount of Nab-sirolimus; (b) an effective amount of an interferon (such as interferon α). In some embodiments, the bladder cancer is non-muscle invasive bladder cancer. In some embodiments, the bladder cancer is BCG-refractory bladder cancer. In some embodiments, the bladder cancer is BCG-refractory non-muscle invasive bladder cancer.

In some embodiments, there is provided a method of treating bladder cancer in an individual (e.g., human) comprising administering (such as intravesicularly administering (for example via urethral catheterization)) to the individual (a) an effective amount of a composition comprising nanoparticles comprising an mTOR inhibitor (such as a limus drug); (b) an effective amount of BCG; and (c) an effective amount of an interferon (such as interferon α). In some embodiments, there is provided a method of treating bladder cancer in an individual (e.g., human) comprising administering (such as intravesicularly administering (for example via urethral catheterization)) to the individual (a) an effective amount of a composition comprising nanoparticles comprising a limus drug and an albumin; (b) an effective amount of BCG; and (c) an effective amount of an interferon (such as interferon α). In some embodiments, there is provided a method of treating bladder cancer in an individual (e.g., human) comprising administering (such as intravesicularly administering (for example via urethral catheterization)) to the individual (a) an effective amount of a composition comprising nanoparticles comprising a limus drug and an albumin, wherein the limus drug in the nanoparticles is coated with the albumin; (b) an effective amount of BCG; and (c) an effective amount of an interferon (such as interferon α). In some embodiments, there is provided a method of treating bladder cancer in an individual (e.g., human) comprising administering (such as intravesicularly administering (for example via urethral catheterization)) to the individual (a) an effective amount of a composition comprising nanoparticles comprising a limus drug and an albumin, wherein the nanoparticles have an average particle size of no greater than about 200 nm (such as no greater than about 150 nm); (b) an effective amount of BCG; and (c) an effective amount of an interferon (such as interferon α). In some embodiments, there is provided a method of treating bladder cancer in an individual (e.g., human) comprising administering (such as intravesicularly administering (for example via urethral catheterization)) to the individual an effective amount of a composition comprising nanoparticles comprising a limus drug and an albumin, wherein the nanoparticles comprise a limus drug coated with albumin, and wherein the nanoparticles have an average particle size of no greater than about 200 nm (such as no greater than about 150 nm); (b) an effective amount of BCG; and (c) an effective amount of an interferon (such as interferon α). In some embodiments, there is provided a method of treating bladder cancer in an individual (e.g., human) comprising administering (such as intravesicularly administering (for example via urethral catheterization)) to the individual (a) an effective amount of a composition comprising nanoparticles comprising sirolimus and human albumin, wherein the nanoparticles comprise sirolimus coated with the human albumin, wherein the nanoparticles have an average particle size of no greater than about 150 nm (such as no greater than about 120 nm, for example about 100 nm), wherein the weight ratio of human albumin and sirolimus in the composition is about 9:1 or less (such as about 9:1 or about 8:1); (b) an effective amount of BCG; and (c) an effective amount of an interferon (such as interferon α). In some embodiments, there is provided a method of treating bladder cancer in an individual (e.g., human) comprising administering (such as intravesicularly administering (for example via urethral catheterization)) to the individual (a) an effective amount of a composition comprising Nab-sirolimus; (b) an effective amount of BCG; and (c) an effective amount of an interferon (such as interferon α). In some embodiments, there is provided a method of treating bladder cancer in an individual (e.g., human) comprising administering (such as intravesicularly administering (for example via urethral catheterization)) administering to the individual (a) an effective amount of Nab-sirolimus; (b) an effective amount of BCG; and (c) an effective amount of an interferon (such as interferon α). In some embodiments, the bladder cancer is non-muscle invasive bladder cancer. In some embodiments, the bladder cancer is BCG-refractory bladder cancer. In some embodiments, the bladder cancer is BCG-refractory non-muscle invasive bladder cancer.

In some embodiments, there is provided a method of treating bladder cancer in an individual, comprising administering to the individual a) an effective amount of at least another therapeutic agent. In some embodiments, the other therapeutic agent is selected from the group consisting of an alkylating agent, an anthracycline antibiotic, a DNA cross-linking agent, an antimetabolite, an indolequinone, a taxane, or a platinum-based agent. In some embodiments, the other therapeutic agent is selected from the group consisting of mitomycin, epirubicin, doxorubicin, vairubicin, gemcitabine, apaziquone, docetaxel, paclitaxel, and cisplatin.

In some embodiments, the other agent to be administered in combination with the mTOR nanoparticle composition (such as the limus nanoparticle composition) is an alkylating agent. Thus, for example, in some embodiments, there is provided a method of treating bladder cancer in an individual (e.g., human) comprising administering (such as intravesicularly administering (for example via urethral catheterization)) to the individual (a) an effective amount of a composition comprising nanoparticles comprising an mTOR inhibitor (such as a limus drug); and (b) an effective amount of an alkylating agent (such as mitomycin). In some embodiments, there is provided a method of treating bladder cancer in an individual (e.g., human) comprising administering (such as intravesicularly administering (for example via urethral catheterization)) to the individual (a) an effective amount of a composition comprising nanoparticles comprising a limus drug and an albumin; and (b) an effective amount of an alkylating agent (such as mitomycin). In some embodiments, there is provided a method of treating bladder cancer in an individual (e.g., human) comprising administering (such as intravesicularly administering (for example via urethral catheterization)) to the individual (a) an effective amount of a composition comprising nanoparticles comprising a limus drug and an albumin, wherein the limus drug in the nanoparticles is coated with the albumin; and (b) an effective amount of an alkylating agent (such as mitomycin). In some embodiments, there is provided a method of treating bladder cancer in an individual (e.g., human) comprising administering (such as intravesicularly administering (for example via urethral catheterization)) to the individual (a) an effective amount of a composition comprising nanoparticles comprising a limus drug and an albumin, wherein the nanoparticles have an average particle size of no greater than about 200 nm (such as no greater than about 150 nm); and (b) an effective amount of an alkylating agent (such as mitomycin). In some embodiments, there is provided a method of treating bladder cancer in an individual (e.g., human) comprising administering (such as intravesicularly administering (for example via urethral catheterization)) to the individual an effective amount of a composition comprising nanoparticles comprising a limus drug and an albumin, wherein the nanoparticles comprise a limus drug coated with albumin, and wherein the nanoparticles have an average particle size of no greater than about 200 nm (such as no greater than about 150 nm); and (b) an effective amount of an alkylating agent (such as mitomycin). In some embodiments, there is provided a method of treating bladder cancer in an individual (e.g., human) comprising administering (such as intravesicularly administering (for example via urethral catheterization)) to the individual (a) an effective amount of a composition comprising nanoparticles comprising sirolimus and human albumin, wherein the nanoparticles comprise sirolimus coated with the human albumin, wherein the nanoparticles have an average particle size of no greater than about 150 nm (such as no greater than about 120 nm, for example about 100 nm), wherein the weight ratio of human albumin and sirolimus in the composition is about 9:1 or less (such as about 9:1 or about 8:1); and (b) an effective amount of an alkylating agent (such as mitomycin). In some embodiments, there is provided a method of treating bladder cancer in an individual (e.g., human) comprising administering (such as intravesicularly administering (for example via urethral catheterization)) to the individual (a) an effective amount of a composition comprising Nab-sirolimus; and (b) an effective amount of an alkylating agent (such as mitomycin). In some embodiments, there is provided a method of treating bladder cancer in an individual (e.g., human) comprising administering (such as intravesicularly administering (for example via urethral catheterization)) administering to the individual (a) an effective amount of Nab-sirolimus; and (b) an effective amount of an alkylating agent (such as mitomycin). In some embodiments, the bladder cancer is non-muscle invasive bladder cancer. In some embodiments, the bladder cancer is BCG-refractory bladder cancer. In some embodiments, the bladder cancer is BCG-refractory non-muscle invasive bladder cancer.

In some embodiments, the other agent to be administered in combination with the mTOR nanoparticle composition (such as the limus nanoparticle composition) is a DNA crosslinking agent. Thus, for example, in some embodiments, there is provided a method of treating bladder cancer in an individual (e.g., human) comprising administering (such as intravesicularly administering (for example via urethral catheterization)) to the individual (a) an effective amount of a composition comprising nanoparticles comprising an mTOR inhibitor (such as a limus drug); and (b) an effective amount of a DNA crosslinking agent (such as mitomycin). In some embodiments, there is provided a method of treating bladder cancer in an individual (e.g., human) comprising administering (such as intravesicularly administering (for example via urethral catheterization)) to the individual (a) an effective amount of a composition comprising nanoparticles comprising a limus drug and an albumin; and (b) an effective amount of a DNA crosslinking agent (such as mitomycin). In some embodiments, there is provided a method of treating bladder cancer in an individual (e.g., human) comprising administering (such as intravesicularly administering (for example via urethral catheterization)) to the individual (a) an effective amount of a composition comprising nanoparticles comprising a limus drug and an albumin, wherein the limus drug in the nanoparticles is coated with the albumin; and (b) an effective amount of a DNA crosslinking agent (such as mitomycin). In some embodiments, there is provided a method of treating bladder cancer in an individual (e.g., human) comprising administering (such as intravesicularly administering (for example via urethral catheterization)) to the individual (a) an effective amount of a composition comprising nanoparticles comprising a limus drug and an albumin, wherein the nanoparticles have an average particle size of no greater than about 200 nm (such as no greater than about 150 nm); and (b) an effective amount of a DNA crosslinking agent (such as mitomycin). In some embodiments, there is provided a method of treating bladder cancer in an individual (e.g., human) comprising administering (such as intravesicularly administering (for example via urethral catheterization)) to the individual an effective amount of a composition comprising nanoparticles comprising a limus drug and an albumin, wherein the nanoparticles comprise a limus drug coated with albumin, and wherein the nanoparticles have an average particle size of no greater than about 200 nm (such as no greater than about 150 nm); and (b) an effective amount of a DNA crosslinking agent (such as mitomycin). In some embodiments, there is provided a method of treating bladder cancer in an individual (e.g., human) comprising administering (such as intravesicularly administering (for example via urethral catheterization)) to the individual (a) an effective amount of a composition comprising nanoparticles comprising sirolimus and human albumin, wherein the nanoparticles comprise sirolimus coated with the human albumin, wherein the nanoparticles have an average particle size of no greater than about 150 nm (such as no greater than about 120 nm, for example about 100 nm), wherein the weight ratio of human albumin and sirolimus in the composition is about 9:1 or less (such as about 9:1 or about 8:1); and (b) an effective amount of a DNA crosslinking agent (such as mitomycin). In some embodiments, there is provided a method of treating bladder cancer in an individual (e.g., human) comprising administering (such as intravesicularly administering (for example via urethral catheterization)) to the individual (a) an effective amount of a composition comprising Nab-sirolimus; and (b) an effective amount of a DNA crosslinking agent (such as mitomycin). In some embodiments, there is provided a method of treating bladder cancer in an individual (e.g., human) comprising administering (such as intravesicularly administering (for example via urethral catheterization)) administering to the individual (a) an effective amount of Nab-sirolimus; and (b) an effective amount of an alkylating agent (such as mitomycin). In some embodiments, the bladder cancer is non-muscle invasive bladder cancer. In some embodiments, the bladder cancer is BCG-refractory bladder cancer. In some embodiments, the bladder cancer is BCG-refractory non-muscle invasive bladder cancer.

In some embodiments, there is provided a method of treating non-muscle invasive bladder cancer in an individual (e.g., human) comprising intravesicularly administering (for example via urethral catheterization) to the individual (a) an effective amount of a composition comprising nanoparticles comprising sirolimus and human albumin, wherein the nanoparticles comprise sirolimus coated with the human albumin, wherein the nanoparticles have an average particle size of no greater than about 150 nm (such as no greater than about 120 nm, for example about 100 nm), wherein the weight ratio of human albumin and sirolimus in the composition is about 9:1 or less (such as about 9:1 or about 8:1), wherein the dose of the sirolimus in the composition is about 5 mg to about 500 mg (such as about 30 mg to about 400 mg, for example about 100 mg) weekly; and (b) an effective amount of an alkylating agent (such as mitomycin), wherein the dose of the alkylating agent (such as mitomycin) is about 8 mg to about 100 mg (such as about 25 mg to about 50 mg, for example about 40 mg) weekly. In some embodiments, there is provided a method of treating bladder cancer (such as non-muscle invasive bladder cancer) in an individual (e.g., human) comprising administering (such as intravesicularly administering (for example via urethral catheterization)) to the individual (a) an effective amount of a composition comprising Nab-sirolimus, wherein the dose of the limus drug in the composition is about 5 mg to about 500 mg (such as about 30 mg to about 400 mg, for example about 100 mg) weekly; and (b) an effective amount of an alkylating agent (such as mitomycin), wherein the dose of the alkylating agent (such as mitomycin) is about 8 mg to about 100 mg (such as about 25 mg to about 50 mg, for example about 40 mg) weekly. In some embodiments, there is provided a method of treating bladder cancer (such as non-muscle invasive bladder cancer) in an individual (e.g., human) comprising administering (such as intravesicularly administering (for example via urethral catheterization)) administering to the individual (a) an effective amount of Nab-sirolimus, wherein the dose of the limus drug in the composition is about 5 mg to about 500 mg (such as about 30 mg to about 400 mg, for example about 100 mg) weekly; and (b) an effective amount of an alkylating agent (such as mitomycin), wherein the dose of the alkylating agent (such as mitomycin) is about 8 mg to about 100 mg (such as about 25 mg to about 50 mg, for example about 40 mg) weekly. In some embodiments, the nanoparticle composition and/or the alkylating agent (such as mitomycin) are provided in a volume of about 20-ml to about 150 ml (such as about 50 ml). In some embodiments, the nanoparticle composition and/or BCG are retained in the bladder for about 30 minutes to about 4 hours (such as about 30 minutes). In some embodiments, the bladder cancer is non-muscle invasive bladder cancer. In some embodiments, the bladder cancer is BCG-refractory bladder cancer. In some embodiments, the bladder cancer is BCG-refractory non-muscle invasive bladder cancer.

In some embodiments, the other agent is an anthracycline antibiotic. Thus, for example, in some embodiments, there is provided a method of treating bladder cancer in an individual (e.g., human) comprising administering (such as intravesicularly administering (for example via urethral catheterization)) to the individual (a) an effective amount of a composition comprising nanoparticles comprising an mTOR inhibitor (such as a limus drug); and (b) an effective amount of an anthracycline (such as epirubicin and/or doxorubicin, or valrubicin). In some embodiments, there is provided a method of treating bladder cancer in an individual (e.g., human) comprising administering (such as intravesicularly administering (for example via urethral catheterization)) to the individual (a) an effective amount of a composition comprising nanoparticles comprising a limus drug and an albumin; and (b) an effective amount of an anthracycline (such as epirubicin and/or doxorubicin, or valrubicin). In some embodiments, there is provided a method of treating bladder cancer in an individual (e.g., human) comprising administering (such as intravesicularly administering (for example via urethral catheterization)) to the individual (a) an effective amount of a composition comprising nanoparticles comprising a limus drug and an albumin, wherein the limus drug in the nanoparticles is coated with the albumin; and (b) an effective amount of an anthracycline (such as epirubicin and/or doxorubicin, or valrubicin). In some embodiments, there is provided a method of treating bladder cancer in an individual (e.g., human) comprising administering (such as intravesicularly administering (for example via urethral catheterization)) to the individual (a) an effective amount of a composition comprising nanoparticles comprising a limus drug and an albumin, wherein the nanoparticles have an average particle size of no greater than about 200 nm (such as no greater than about 150 nm); and (b) an effective amount of an anthracycline (such as epirubicin and/or doxorubicin, or valrubicin). In some embodiments, there is provided a method of treating bladder cancer in an individual (e.g., human) comprising administering (such as intravesicularly administering (for example via urethral catheterization)) to the individual an effective amount of a composition comprising nanoparticles comprising a limus drug and an albumin, wherein the nanoparticles comprise a limus drug coated with albumin, and wherein the nanoparticles have an average particle size of no greater than about 200 nm (such as no greater than about 150 nm); and (b) an effective amount of an anthracycline (such as epirubicin and/or doxorubicin, or valrubicin). In some embodiments, there is provided a method of treating bladder cancer in an individual (e.g., human) comprising administering (such as intravesicularly administering (for example via urethral catheterization)) to the individual (a) an effective amount of a composition comprising nanoparticles comprising sirolimus and human albumin, wherein the nanoparticles comprise sirolimus coated with the human albumin, wherein the nanoparticles have an average particle size of no greater than about 150 nm (such as no greater than about 120 nm, for example about 100 nm), wherein the weight ratio of human albumin and sirolimus in the composition is about 9:1 or less (such as about 9:1 or about 8:1); and (b) an effective amount of an anthracycline (such as epirubicin and/or doxorubicin, or valrubicin). In some embodiments, there is provided a method of treating bladder cancer in an individual (e.g., human) comprising administering (such as intravesicularly administering (for example via urethral catheterization)) to the individual (a) an effective amount of a composition comprising Nab-sirolimus; and (b) an effective amount of an anthracycline (such as epirubicin and/or doxirubicin). In some embodiments, there is provided a method of treating bladder cancer in an individual (e.g., human) comprising administering (such as intravesicularly administering (for example via urethral catheterization)) administering to the individual (a) an effective amount of Nab-sirolimus; and (b) an effective amount of an anthracycline (such as epirubicin and/or doxorubicin, or valrubicin). In some embodiments, the bladder cancer is non-muscle invasive bladder cancer. In some embodiments, the bladder cancer is BCG-refractory bladder cancer. In some embodiments, the bladder cancer is BCG-refractory non-muscle invasive bladder cancer.

In some embodiments, the other agent is an antimetabolite. Thus, for example, in some embodiments, there is provided a method of treating bladder cancer in an individual (e.g., human) comprising administering (such as intravesicularly administering (for example via urethral catheterization)) to the individual (a) an effective amount of a composition comprising nanoparticles comprising a limus drug and an albumin; and (b) an effective amount of an antimetabolite (such as gemcitabine). In some embodiments, there is provided a method of treating bladder cancer in an individual (e.g., human) comprising administering (such as intravesicularly administering (for example via urethral catheterization)) to the individual (a) an effective amount of a composition comprising nanoparticles comprising an mTOR inhibitor (such as a limus drug); and (b) an effective amount of an antimetabolite (such as gemcitabine). In some embodiments, there is provided a method of treating bladder cancer in an individual (e.g., human) comprising administering (such as intravesicularly administering (for example via urethral catheterization)) to the individual (a) an effective amount of a composition comprising nanoparticles comprising a limus drug and an albumin, wherein the limus drug in the nanoparticles is coated with the albumin; and (b) an effective amount of an antimetabolite (such as gemcitabine). In some embodiments, there is provided a method of treating bladder cancer in an individual (e.g., human) comprising administering (such as intravesicularly administering (for example via urethral catheterization)) to the individual (a) an effective amount of a composition comprising nanoparticles comprising a limus drug and an albumin, wherein the nanoparticles have an average particle size of no greater than about 200 nm (such as no greater than about 150 nm); and (b) an effective amount of an antimetabolite (such as gemcitabine). In some embodiments, there is provided a method of treating bladder cancer in an individual (e.g., human) comprising administering (such as intravesicularly administering (for example via urethral catheterization)) to the individual an effective amount of a composition comprising nanoparticles comprising a limus drug and an albumin, wherein the nanoparticles comprise a limus drug coated with albumin, and wherein the nanoparticles have an average particle size of no greater than about 200 nm (such as no greater than about 150 nm); and (b) an effective amount of an antimetabolite (such as gemcitabine). In some embodiments, there is provided a method of treating bladder cancer in an individual (e.g., human) comprising administering (such as intravesicularly administering (for example via urethral catheterization)) to the individual (a) an effective amount of a composition comprising nanoparticles comprising sirolimus and human albumin, wherein the nanoparticles comprise sirolimus coated with the human albumin, wherein the nanoparticles have an average particle size of no greater than about 150 nm (such as no greater than about 120 nm, for example about 100 nm), wherein the weight ratio of human albumin and sirolimus in the composition is about 9:1 or less (such as about 9:1 or about 8:1); and (b) an effective amount of an antimetabolite (such as gemcitabine). In some embodiments, there is provided a method of treating bladder cancer in an individual (e.g., human) comprising administering (such as intravesicularly administering (for example via urethral catheterization)) to the individual (a) an effective amount of a composition comprising Nab-sirolimus; and (b) an effective amount of an antimetabolite (such as gemcitabine). In some embodiments, there is provided a method of treating bladder cancer in an individual (e.g., human) comprising administering (such as intravesicularly administering (for example via urethral catheterization)) administering to the individual (a) an effective amount of Nab-sirolimus; and (b) an effective amount of an antimetabolite (such as gemcitabine). In some embodiments, the bladder cancer is non-muscle invasive bladder cancer. In some embodiments, the bladder cancer is BCG-refractory bladder cancer. In some embodiments, the bladder cancer is BCG-refractory non-muscle invasive bladder cancer. In some embodiments, the antimetabolite (such as gemcitabine) is administered weekly, for example by weekly intravesicular administration at the dose of 2 grams in 50 ml, each with about 30 minutes to about 4 hours, for example about 1 hour to about 2 hours of retention time in the bladder. In some embodiments, the antimetabolite (such as gemcitabine) is administered immediately before or after the administration of the nanoparticle composition.

In some embodiments, the other agent is a taxane. Suitable taxanes include, but are not limited to, paclitaxel and docetaxel. The taxane can be provided in nanoparticle forms. In some embodiments, the second agent is Abraxane®. Thus, for example, in some embodiments, there is provided a method of treating bladder cancer in an individual (e.g., human) comprising administering (such as intravesicularly administering (for example via urethral catheterization)) to the individual (a) an effective amount of a composition comprising nanoparticles comprising an mTOR inhibitor (such as a limus drug); and (b) an effective amount of a taxane (such as paclitaxel or docetaxel). In some embodiments, there is provided a method of treating bladder cancer in an individual (e.g., human) comprising administering (such as intravesicularly administering (for example via urethral catheterization)) to the individual (a) an effective amount of a composition comprising nanoparticles comprising a limus drug and an albumin; and (b) an effective amount of a taxane (such as paclitaxel or docetaxel). In some embodiments, there is provided a method of treating bladder cancer in an individual (e.g., human) comprising administering (such as intravesicularly administering (for example via urethral catheterization)) to the individual (a) an effective amount of a composition comprising nanoparticles comprising a limus drug and an albumin, wherein the limus drug in the nanoparticles is coated with the albumin; and (b) an effective amount of a taxane (such as paclitaxel or docetaxel). In some embodiments, there is provided a method of treating bladder cancer in an individual (e.g., human) comprising administering (such as intravesicularly administering (for example via urethral catheterization)) to the individual (a) an effective amount of a composition comprising nanoparticles comprising a limus drug and an albumin, wherein the nanoparticles have an average particle size of no greater than about 200 nm (such as no greater than about 150 nm); and (b) an effective amount of a taxane (such as paclitaxel or docetaxel). In some embodiments, there is provided a method of treating bladder cancer in an individual (e.g., human) comprising administering (such as intravesicularly administering (for example via urethral catheterization)) to the individual an effective amount of a composition comprising nanoparticles comprising a limus drug and an albumin, wherein the nanoparticles comprise a limus drug coated with albumin, and wherein the nanoparticles have an average particle size of no greater than about 200 nm (such as no greater than about 150 nm); and (b) an effective amount of a taxane (such as paclitaxel or docetaxel). In some embodiments, there is provided a method of treating bladder cancer in an individual (e.g., human) comprising administering (such as intravesicularly administering (for example via urethral catheterization)) to the individual (a) an effective amount of a composition comprising nanoparticles comprising sirolimus and human albumin, wherein the nanoparticles comprise sirolimus coated with the human albumin, wherein the nanoparticles have an average particle size of no greater than about 150 nm (such as no greater than about 120 nm, for example about 100 nm), wherein the weight ratio of human albumin and sirolimus in the composition is about 9:1 or less (such as about 9:1 or about 8:1); and (b) an effective amount of a taxane (such as paclitaxel or docetaxel). In some embodiments, there is provided a method of treating bladder cancer in an individual (e.g., human) comprising administering (such as intravesicularly administering (for example via urethral catheterization)) to the individual (a) an effective amount of a composition comprising Nab-sirolimus; and (b) an effective amount of a taxane (such as paclitaxel or docetaxel). In some embodiments, there is provided a method of treating bladder cancer in an individual (e.g., human) comprising administering (such as intravesicularly administering (for example via urethral catheterization)) administering to the individual (a) an effective amount of Nab-sirolimus; and (b) an effective amount of a taxane (such as paclitaxel or docetaxel). In some embodiments, the bladder cancer is non-muscle invasive bladder cancer. In some embodiments, the bladder cancer is BCG-refractory bladder cancer. In some embodiments, the bladder cancer is BCG-refractory non-muscle invasive bladder cancer.

In some embodiments, the other agent is a platinum-based agent. Thus, for example, in some embodiments, there is provided a method of treating bladder cancer in an individual (e.g., human) comprising administering (such as intravesicularly administering (for example via urethral catheterization)) to the individual (a) an effective amount of a composition comprising nanoparticles comprising an mTOR inhibitor (such as a limus drug); and (b) an effective amount of a platinum-based agent (such as carboplatin or cisplatin). In some embodiments, there is provided a method of treating bladder cancer in an individual (e.g., human) comprising administering (such as intravesicularly administering (for example via urethral catheterization)) to the individual (a) an effective amount of a composition comprising nanoparticles comprising a limus drug and an albumin; and (b) an effective amount of a platinum-based agent (such as carboplatin or cisplatin). In some embodiments, there is provided a method of treating bladder cancer in an individual (e.g., human) comprising administering (such as intravesicularly administering (for example via urethral catheterization)) to the individual (a) an effective amount of a composition comprising nanoparticles comprising a limus drug and an albumin, wherein the limus drug in the nanoparticles is coated with the albumin; and (b) an effective amount of a platinum-based agent (such as carboplatin or cisplatin). In some embodiments, there is provided a method of treating bladder cancer in an individual (e.g., human) comprising administering (such as intravesicularly administering (for example via urethral catheterization)) to the individual (a) an effective amount of a composition comprising nanoparticles comprising a limus drug and an albumin, wherein the nanoparticles have an average particle size of no greater than about 200 nm (such as no greater than about 150 nm); and (b) an effective amount of a platinum-based agent (such as carboplatin or cisplatin). In some embodiments, there is provided a method of treating bladder cancer in an individual (e.g., human) comprising administering (such as intravesicularly administering (for example via urethral catheterization)) to the individual an effective amount of a composition comprising nanoparticles comprising a limus drug and an albumin, wherein the nanoparticles comprise a limus drug coated with albumin, and wherein the nanoparticles have an average particle size of no greater than about 200 nm (such as no greater than about 150 nm); and (b) an effective amount of a platinum-based agent (such as carboplatin or cisplatin). In some embodiments, there is provided a method of treating bladder cancer in an individual (e.g., human) comprising administering (such as intravesicularly administering (for example via urethral catheterization)) to the individual (a) an effective amount of a composition comprising nanoparticles comprising sirolimus and human albumin, wherein the nanoparticles comprise sirolimus coated with the human albumin, wherein the nanoparticles have an average particle size of no greater than about 150 nm (such as no greater than about 120 nm, for example about 100 nm), wherein the weight ratio of human albumin and sirolimus in the composition is about 9:1 or less (such as about 9:1 or about 8:1); and (b) an effective amount of a platinum-based agent (such as carboplatin or cisplatin). In some embodiments, there is provided a method of treating bladder cancer in an individual (e.g., human) comprising administering (such as intravesicularly administering (for example via urethral catheterization)) to the individual (a) an effective amount of a composition comprising Nab-sirolimus; and (b) an effective amount of a platinum-based agent (such as carboplatin or cisplatin). In some embodiments, there is provided a method of treating bladder cancer in an individual (e.g., human) comprising administering (such as intravesicularly administering (for example via urethral catheterization)) administering to the individual (a) an effective amount of Nab-sirolimus; and (b) an effective amount of a platinum-based agent (such as carboplatin or cisplatin). In some embodiments, the bladder cancer is non-muscle invasive bladder cancer. In some embodiments, the bladder cancer is BCG-refractory bladder cancer. In some embodiments, the bladder cancer is BCG-refractory non-muscle invasive bladder cancer.

The methods described herein may comprise administration of a limus nanoparticle composition in combination with two or more other agents. These two or more other agents may be of the same or different classes. For example, in some embodiments, there is provided a method of treating bladder cancer in an individual (e.g., human) comprising administering (such as intravesicularly administering (for example via urethral catheterization)) to the individual (a) an effective amount of a composition comprising nanoparticles comprising an mTOR inhibitor (such as a limus drug); (b) an effective amount of BCG; and (c) an effective amount of mitomycin. In some embodiments, there is provided a method of treating bladder cancer in an individual (e.g., human) comprising administering (such as intravesicularly administering (for example via urethral catheterization)) to the individual (a) an effective amount of a composition comprising nanoparticles comprising a limus drug and an albumin; (b) an effective amount of BCG; and (c) an effective amount of mitomycin. In some embodiments, there is provided a method of treating bladder cancer in an individual (e.g., human) comprising administering (such as intravesicularly administering (for example via urethral catheterization)) to the individual (a) an effective amount of a composition comprising nanoparticles comprising a limus drug and an albumin, wherein the limus drug in the nanoparticles is coated with the albumin; (b) an effective amount of BCG; and (c) an effective amount of mitomycin. In some embodiments, there is provided a method of treating bladder cancer in an individual (e.g., human) comprising administering (such as intravesicularly administering (for example via urethral catheterization)) to the individual (a) an effective amount of a composition comprising nanoparticles comprising a limus drug and an albumin, wherein the nanoparticles have an average particle size of no greater than about 200 nm (such as no greater than about 150 nm); (b) an effective amount of BCG; and (c) an effective amount of mitomycin. In some embodiments, there is provided a method of treating bladder cancer in an individual (e.g., human) comprising administering (such as intravesicularly administering (for example via urethral catheterization)) to the individual an effective amount of a composition comprising nanoparticles comprising a limus drug and an albumin, wherein the nanoparticles comprise a limus drug coated with albumin, and wherein the nanoparticles have an average particle size of no greater than about 200 nm (such as no greater than about 150 nm); (b) an effective amount of BCG; and (c) an effective amount of mitomycin. In some embodiments, there is provided a method of treating bladder cancer in an individual (e.g., human) comprising administering (such as intravesicularly administering (for example via urethral catheterization)) to the individual (a) an effective amount of a composition comprising nanoparticles comprising sirolimus and human albumin, wherein the nanoparticles comprise sirolimus coated with the human albumin, wherein the nanoparticles have an average particle size of no greater than about 150 nm (such as no greater than about 120 nm, for example about 100 nm), wherein the weight ratio of human albumin and sirolimus in the composition is about 9:1 or less (such as about 9:1 or about 8:1); (b) an effective amount of BCG; and (c) an effective amount of mitomycin. In some embodiments, there is provided a method of treating bladder cancer in an individual (e.g., human) comprising administering (such as intravesicularly administering (for example via urethral catheterization)) to the individual (a) an effective amount of a composition comprising Nab-sirolimus; (b) an effective amount of BCG; and (c) an effective amount of mitomycin. In some embodiments, there is provided a method of treating bladder cancer in an individual (e.g., human) comprising administering (such as intravesicularly administering (for example via urethral catheterization)) administering to the individual (a) an effective amount of Nab-sirolimus; (b) an effective amount of BCG; and (c) an effective amount of mitomycin. In some embodiments, the bladder cancer is non-muscle invasive bladder cancer. In some embodiments, the bladder cancer is BCG-refractory bladder cancer. In some embodiments, the bladder cancer is BCG-refractory non-muscle invasive bladder cancer.

Use of Biomarkers

The present application further provides methods of treatments (such as any of the treatment methods described above) based on the expression of one or more biomarkers. Biomarkers useful for methods described herein include, but are not limited to, p-S6K, pAKT, p-4EBP1, Ki67, p53, p63, Stathmin, Tau, SPARC, p73, c-myc, and cyclin D1. In some embodiments, the biomarker is selected from the group consisting of p-S6K, pAKT, p-4EBP1, Ki67, p53, p63, Stathmin, Tau, SPARC, p73, c-myc, TSC1, and cyclin D1.

PS6k encodes a member of the RSK (ribosomal s6 kinase) family of serine/threonine kinases. This kinase contains 2 non-identical kinase catalytic domains and phosphorylates several residues of the S6 ribosomal protein. The kinase activity of this protein leads to an increase in protein synthesis and cell proliferation.

Akt, also known as Protein Kinase B (PKB), is a serine/threonine-specific protein kinase that plays a key role in multiple cellular processes, including, e.g., glucose metabolism, apoptosis, cell proliferation, transcription and cell migration.

p4EBP1 is a member of a family of translation repressor proteins. p4EBP1 directly interacts with eukaryotic translation initiation factor 4E (eIF4E), which is a limiting component of the multi-subunit complex that recruits 40S ribosomal subunits to the 5' end of mRNAs. Interaction of this protein with eIF4E inhibits complex assembly and represses translation. It has been shown that mTOR signals downstream to at least S6K1 and 4EBP1/eIF4E, which themselves function in translational control to regulate mammalian cell size (Fingar et al. (2002) Genes Dev. 16: 1472-1487).

The Ki-67 protein (also known as MKI67) is a cellular marker for proliferation (Wu et al. (2003) Dev. Cell 5: 723-34). During interphase, Ki-67 can be exclusively detected within the cell nucleus, whereas in mitosis most of the protein is relocated to the surface of the chromosomes. Ki-67 is present during all active phases of the cell cycle (G1, S, G2, and mitosis), but is absent from resting cells (G0).

p53 (also known as protein 53 or tumor protein 53), is a tumor suppressor protein that in humans is encoded by the TP53 gene. p53 is a transcription factor that is crucial in multicellular organisms, where it regulates the cell cycle and, thus, functions as a tumor suppressor that is involved in preventing cancer. p63 (also known as TP63) is a member of the p53 family of transcription factors. p63 −/− mice have several developmental defects which include the lack of limbs and other tissues, such as teeth and mammary glands, which develop as a result of interactions between mesenchyme and epithelium. In humans, mutations in the TP63 gene are associated with ectrodactyly-ectodermal dysplasia-cleft syndrome, Hay-Wells syndrome, cleft lip/palate syndrome 3 (EEC3); ectrodactyly (also known as split-hand/foot malformation 4 (SHFM4)); ankyloblepharon-ectodermal defects-cleft lip/palate, ADULT syndrome (acro-dermato-ungual-lacrimal-tooth), limb-mammary syndrome, Rap-Hodgkin syndrome (RHS), and orofacial cleft 8. p73 (or TP73) was first identified as a homologue of p53. The protein product of p73 induces cell cycle arrest or apoptosis. Accordingly, p73 is classified as a tumor suppressor. However unlike p53, p73 is infrequently mutated in cancers.

Stathmin 1/oncoprotein 18, also known as STMN1, is a highly conserved 17 kDa protein that regulates microtubule dynamics. Stathmin forms a complex with dimeric $\alpha,\beta$-tubulin to form a ternary complex called the T2S complex. When stathmin sequesters tubulin into the T2S complex, tubulin becomes non-polymerizable. As a result, microtubule assembly is inhibited. Through this mechanism, stathmin promotes microtubule disassembly.

Tau proteins are highly soluble microtubule-associated proteins (MAPs). In humans, these proteins are mostly found in neurons compared to non-neuronal cells. For example, tau proteins are expressed in central nervous system astrocytes and oligodendrocytes. One of tau's main functions is to modulate the stability of axonal microtubules and promote tubulin assembly into microtubules. Six tau isoforms exist in human brain tissue.

The Myc (c-Myc) gene encodes a transcription factor that activates expression of many genes through binding on Enhancer Box sequences (E-boxes) and recruiting histone acetyltransferases (HATs). Accordingly, Myc also functions to regulate global chromatin structure. Myc is activated upon various mitogenic signals such as Wnt, Shh and EGF (via the MAPK/ERK pathway). By modifying the expression of its target genes, Myc activation results in numerous biological effects. Myc plays roles in driving cell proliferation, regulating cell growth and apoptosis, and regulating differentiation and stem cell self-renewal.

Cyclin D1 encodes the regulatory subunit of a holoenzyme that phosphorylates and inactivates the retinoblastoma protein and promotes progression through the G1-S phase of the cell cycle. Amplification or overexpression of cyclin D1 plays pivotal roles in the development of a subset of human cancers including parathyroid adenoma, breast cancer, colon cancer, lymphoma, melanoma, and prostate cancer. Of the three D-type cyclins, each of which binds cyclin-dependent kinase (CDK), it is cyclin D1 overexpression that is predominantly associated with human tumorigenesis and cellular metastases.

SPARC (Secreted Protein, Acidic and Rich in Cysteine) is a matricellular protein upregulated in several aggressive cancers. See Porter et al., J. Histochem. Cytochem. 1995; 43:791. The human SPARC gene encodes a 303 amino acid SPARC proteins, while mature SPARC is a 285 amino acid glycoprotein. After cleavage of the signal sequence a 32-kD secreted form is produced which migrates at 43 kD on SDA-PAGE because of glycosylation.

TSC1 (also referred to as Hamartin or tuberous sclerosis 1) is a peripheral membrane protein implicated as a tumor suppressor. It forms a complex with TSC2 that regulates mTORC1 signaling and may be also involved in vesicular transport and docking.

Thus, the present invention in some embodiments provides a method of treating bladder cancer in an individual (such as human) comprising administering to the individual an effective amount of a composition comprising nanoparticles comprising an mTOR inhibitor (such as a limus drug), wherein the individual is selected for treatment based on the level of one or more of: p-S6K, pAKT, p-4EBP1, Ki67, p53, p63, Stathmin, Tau, SPARC, p'73, c-myc, and cyclin D1. In some embodiments, the individual is selected for treatment based on the level of one of more of: p-S6K, pAKT, p-4EBP1, and Ki67. In some embodiments, there is provided a method of treating bladder cancer in an individual (such as human) comprising administering to the individual an effective amount of a composition comprising nanoparticles comprising an mTOR inhibitor (such as a limus drug), wherein the individual is selected for treatment based on the level of one or more of: p-S6K, pAKT, p-4EBP1, Ki67, p53, p63, Stathmin, Tau, SPARC, p73, c-myc, TSC1, and cyclin D1. In some embodiments, the individual is selected for treatment based on the level of TSC1. In some embodiments, the method comprises administering to the individual an effective amount of a composition comprising nanoparticles comprising a limus drug and an albumin. In some embodiments, the method comprises administering to the individual an effective amount of a composition comprising nanoparticles comprising a limus drug and an albumin, wherein the limus drug in the nanoparticles is coated with the albumin. In some embodiments, the method comprises administering to the individual an effective amount of a composition comprising nanoparticles comprising a limus drug and an albumin, wherein the nanoparticles have an average particle size of no greater than about 200 nm (such as no greater than about 150 nm). In some embodiments, the method comprises administering to the individual an effective amount of a composition comprising nanoparticles comprising a limus drug and an albumin, wherein the nanoparticles comprise a limus drug coated with albumin, wherein the nanoparticles have an average particle size of no greater than about 200 nm (such as no greater than about 150 nm). In some embodiments, the method comprises administering to the individual an effective amount of a composition comprising nanoparticles comprising sirolimus and human albumin, wherein the nanoparticles comprise sirolimus coated with human albumin, wherein the nanoparticles have an average particle size of no greater than about 150 nm (such as no greater than about 120 nm, for example about 100 nm), wherein the weight ratio of human albumin and sirolimus in the composition is about 9:1 or less (such as about 9:1 or about 8:1). In some embodiments, the composition comprises Nab-sirolimus. In some embodiments, the composition is Nab-sirolimus. In some embodiments, the method further comprises administering to the individual an effective amount of another agent (such as BCG and/or mitomycin).

As used herein, "based upon" or "based on" include assessing, determining, or measuring the individual's characteristics as described herein (and preferably selecting an individual suitable for receiving treatment). When a biomarker is used as a basis for selection, assessing (or aiding in assessing), measuring, or determining method of treatment as described herein, the biomarker is measured before and/or during treatment, and the values obtained are used by a clinician in assessing any of the following: (a) probable or likely suitability of an individual to initially receive treatment(s); (b) probable or likely unsuitability of an individual to initially receive treatment(s); (c) responsiveness to treatment; (d) probable or likely suitability of an individual to continue to receive treatment(s); (e) probable or likely unsuitability of an individual to continue to receive treatment(s); (f) adjusting dosage; or (g) predicting likelihood of clinical benefits.

Thus, the present invention in some embodiments provides a method of treating bladder cancer in an individual (such as human) comprising administering to the individual an effective amount of a composition comprising nanoparticles comprising an mTOR inhibitor (such as a limus drug), wherein the individual is selected for treatment based on a high level of one or more of: p-S6K, pAKT, p-4EBP1, Ki67, p53, p63, Stathmin, Tau, SPARC, p73, c-myc, and cyclin D1. In some embodiments, the individual is selected for treatment based on a high level of one of more of: p-S6K, pAKT, p-4EBP1, and Ki67. In some embodiments, the method comprises administering to the individual an effective amount of a composition comprising nanoparticles comprising a limus drug and an albumin. In some embodiments, the method comprises administering to the individual an effective amount of a composition comprising nanoparticles comprising a limus drug and an albumin, wherein the limus drug in the nanoparticles is coated with the albumin. In some embodiments, the method comprises administering to the individual an effective amount of a composition comprising nanoparticles comprising a limus drug and an albumin, wherein the nanoparticles have an average particle size of no greater than about 200 nm (such as no greater than about 150 nm). In some embodiments, the method comprises administering to the individual an effective amount of a composition comprising nanoparticles comprising a limus drug and an albumin, wherein the nanoparticles comprise a limus drug coated with albumin, wherein the nanoparticles have an average particle size of no greater than about 200 nm (such as no greater than about 150 nm). In some embodiments, the method comprises administering to the individual an effective amount of a composition comprising nanoparticles comprising sirolimus and human albumin, wherein the nanoparticles comprise sirolimus coated with human albumin, wherein the nanoparticles have an average particle size of no greater than about 150 nm (such as no greater than about 120 nm, for example about 100 nm), wherein the weight ratio of human albumin and sirolimus in the composition is about 9:1 or less (such as about 9:1 or about 8:1). In some embodiments, the composition comprises Nab-sirolimus. In some embodiments, the composition is Nab-sirolimus. In some embodiments, the composition is Nab-sirolimus. In some embodiments, the method further comprises administering to the individual an effective amount of another agent (such as BCG and/or mitomycin).

In some embodiments, there is provided a method of treating bladder cancer in an individual (such as human) comprising administering to the individual an effective amount of a composition comprising nanoparticles comprising an mTOR inhibitor (such as a limus drug), wherein the individual has a high level of one or more of: p-S6K, pAKT, p-4EBP1, Ki67, p53, p63, Stathmin, Tau, SPARC, p73, c-myc, and cyclin D1. In some embodiments, the individual has a high level of one of more of: p-S6K, pAKT, p-4EBP1, and Ki67. In some embodiments, the method comprises administering to the individual an effective amount of a composition comprising nanoparticles comprising a limus drug and an albumin. In some embodiments, the method comprises administering to the individual an effective amount of a composition comprising nanoparticles comprising a limus drug and an albumin, wherein the limus drug in the nanoparticles is coated with the albumin. In some embodiments, the method comprises administering to the individual an effective amount of a composition comprising nanoparticles comprising a limus drug and an albumin, wherein the nanoparticles have an average particle size of no greater than about 200 nm (such as no greater than about 150 nm). In some embodiments, the method comprises administering to the individual an effective amount of a composition comprising nanoparticles comprising a limus drug and an albumin, wherein the nanoparticles comprise a limus drug coated with albumin, wherein the nanoparticles have an average particle size of no greater than about 200 nm (such as no greater than about 150 nm). In some embodiments, the method comprises administering to the individual an effective amount of a composition comprising nanoparticles comprising sirolimus and human albumin, wherein the nanoparticles comprise sirolimus coated with human albumin, wherein the nanoparticles have an average particle size of no greater than about 150 nm (such as no greater than about 120 nm, for example about 100 nm), wherein the weight ratio of human albumin and sirolimus in the composition is about 9:1 or less (such as about 9:1 or about 8:1). In some embodiments, the composition comprises Nab-sirolimus. In some embodiments, the composition is Nab-sirolimus. In some embodiments, the composition is Nab-sirolimus. In some embodiments, the method further comprises administering to the individual an effective amount of another agent (such as BCG and/or mitomycin).

In some embodiments, there is provided a method of treating bladder cancer in an individual (such as human) comprising: a) determining the level of one or more biomarkers selected from the group consisting of p-S6K, pAKT, p-4EBP1, Ki67, p53, p63, Stathmin, Tau, SPARC, p73, c-myc, and cyclin D1 in the individual; and b) selecting the individual for treatment based on the individual having a high level of one of more of the biomarkers, wherein the treatment method comprises administering to the individual an effective amount of a composition comprising nanoparticles comprising an mTOR inhibitor (such as a limus drug). In some embodiments, the individual is selected for treatment based on the individual having a high level of one of more biomarkers selected from the group consisting of p-S6K, pAKT, p-4EBP1, and Ki67. In some embodiments, the method comprises administering to the individual an effective amount of a composition comprising nanoparticles comprising a limus drug and an albumin. In some embodiments, the method comprises administering to the individual an effective amount of a composition comprising nanoparticles comprising a limus drug and an albumin, wherein the limus drug in the nanoparticles is coated with the albumin. In some embodiments, the method comprises administering to the individual an effective amount of a composition comprising nanoparticles comprising a limus drug and an albumin, wherein the nanoparticles have an average particle size of no greater than about 200 nm (such as no greater than about 150 nm). In some embodiments, the method comprises administering to the individual an effective amount of a composition comprising nanoparticles comprising a limus drug and an albumin, wherein the nanoparticles comprise a limus drug coated with albumin, wherein the nanoparticles have an average particle size of no greater than about 200 nm (such as no greater than about 150 nm). In some embodiments, the method comprises administering to the individual an effective amount of a composition comprising nanoparticles comprising sirolimus and human albumin, wherein the nanoparticles comprise sirolimus coated with human albumin, wherein the nanoparticles have an average particle size of no greater than about 150 nm (such as no greater than about 120 nm, for example about 100 nm), wherein the weight ratio of human albumin and sirolimus in the composition is about 9:1 or less (such as about 9:1 or about 8:1). In some embodiments, the composition comprises Nab-sirolimus. In some embodiments, the composition is Nab-sirolimus. In some embodiments, the composition is Nab-sirolimus. In some embodiments, the method further comprises administering to the individual an effective amount of another agent (such as BCG and/or mitomycin).

In some embodiments, there is provided a method of treating bladder cancer in an individual (such as human) comprising: a) selecting the individual for treatment based on the individual having a high level of one of more of the biomarkers selected from the group consisting of p-S6K, pAKT, p-4EBP1, Ki67, p53, p63, Stathmin, Tau, SPARC, p73, c-myc, and cyclin D1 in the individual; b) administering to the selected individual an effective amount of a composition comprising nanoparticles comprising an mTOR inhibitor (such as a limus drug). In some embodiments, the individual is selected for treatment based on the individual having a high level of one of more biomarkers selected from the group consisting of p-S6K, pAKT, p-4EBP1, and Ki67. In some embodiments, the method comprises administering to the individual an effective amount of a composition comprising nanoparticles comprising a limus drug and an albumin. In some embodiments, the method comprises administering to the individual an effective amount of a composition comprising nanoparticles comprising a limus drug and an albumin, wherein the limus drug in the nanoparticles is coated with the albumin. In some embodiments, the method comprises administering to the individual an effective amount of a composition comprising nanoparticles comprising a limus drug and an albumin, wherein the nanoparticles have an average particle size of no greater than about 200 nm (such as no greater than about 150 nm). In some embodiments, the method comprises administering to the individual an effective amount of a composition comprising nanoparticles comprising a limus drug and an albumin, wherein the nanoparticles comprise a limus drug coated with albumin, wherein the nanoparticles have an average particle size of no greater than about 200 nm (such as no greater than about 150 nm). In some embodiments, the method comprises administering to the individual an effective amount of a composition comprising nanoparticles comprising sirolimus and human albumin, wherein the nanoparticles comprise sirolimus coated with human albumin, wherein the nanoparticles have an average particle size of no greater than about 150 nm (such as no greater than about 120 nm, for example about 100 nm), wherein the weight ratio of human albumin and sirolimus in the composition is about 9:1 or less (such as about 9:1 or about 8:1). In some embodiments, the composition comprises Nab-sirolimus. In some embodiments, the composition is Nab-sirolimus. In some embodiments, the composition is Nab-sirolimus. In some embodiments, the method further comprises administering to the individual an effective amount of another agent (such as BCG and/or mitomycin).

In some embodiments, there is provided a method of treating bladder cancer in an individual (such as human) comprising: a) determining the level of one or more biomarkers selected from the group consisting of p-S6K, pAKT, p-4EBP1, Ki67, p53, p63, Stathmin, Tau, SPARC, p73, c-myc, and cyclin D1 in the individual; and b) selecting the individual for treatment based on the individual having a high level of one of more of the biomarkers, c) administering to the selected individual an effective amount of a composition comprising nanoparticles comprising an mTOR inhibitor (such as a limus drug). In some embodiments, the individual is selected for treatment based on the individual having a high level of one or more biomarkers selected from the group consisting of p-S6K, pAKT, p-4EBP1, and Ki67. In some embodiments, the method comprises administering to the individual an effective amount of a composition comprising nanoparticles comprising a limus drug and an albumin. In some embodiments, the method comprises administering to the individual an effective amount of a composition comprising nanoparticles comprising a limus drug and an albumin, wherein the limus drug in the nanoparticles is coated with the albumin. In some embodiments, the method comprises administering to the individual an effective amount of a composition comprising nanoparticles comprising a lupus drug and an albumin, wherein the nanoparticles have an average particle size of no greater than about 200 nm (such as no greater than about 150 nm). In some embodiments, the method comprises administering to the individual an effective amount of a composition comprising nanoparticles comprising a limus drug and an albumin, wherein the nanoparticles comprise a limus drug coated with albumin, wherein the nanoparticles have an average particle size of no greater than about 200 nm (such as no greater than about 150 nm). In some embodiments, the method comprises administering to the individual an effective amount of a composition comprising nanoparticles comprising sirolimus and human albumin, wherein the nanoparticles comprise sirolimus coated with human albumin, wherein the nanoparticles have an average particle size of no greater than about 150 nm (such as no greater than about 120 nm, for example about 100 nm), wherein the weight ratio of human albumin and sirolimus in the composition is about 9:1 or less (such as about 9:1 or about 8:1). In some embodiments, the composition comprises Nab-sirolimus. In some embodiments, the composition is Nab-sirolimus. In some embodiments, the composition is Nab-sirolimus. In some embodiments, the method further comprises administering to the individual an effective amount of another agent (such as BCG and/or mitomycin).

In some embodiments, there is provided a method of assessing whether an individual with bladder cancer is more likely to respond to a treatment comprising administering to the selected individual an effective amount of a composition comprising nanoparticles comprising an mTOR inhibitor (such as a limus drug), the method comprising assessing the level of one or more biomarkers selected from the group consisting of p-S6K, pAKT, p-4EBP1, Ki67, p53, p63, Stathmin, Tau, SPARC, p73, c-myc, and cyclin D1 in the individual; wherein a low level of one or more of the biomarkers indicates that the individual is less likely to respond to the treatment, wherein a high level of one of more of the biomarkers indicates that the individual is more likely to respond to the treatment. In some embodiments, the method further comprises selecting the individual for treatment based on the individual having a high level of one of more of the biomarkers. In some embodiments, the method further comprises administering to the selected individual an effective amount of a composition comprising nanoparticles comprising an mTOR inhibitor (such as a limus drug). In some embodiments, the individual is selected for treatment based on the individual having a high level of one or more biomarkers selected from the group consisting of p-S6K, pAKT, p-4EBP1, and Ki67. In some embodiments, the treatment method comprises administering to the individual an effective amount of a composition comprising nanoparticles comprising a limus drug and an albumin. In some embodiments, the treatment method comprises administering to the individual an effective amount of a composition comprising nanoparticles comprising a limus drug and an albumin, wherein the limus drug in the nanoparticles is coated with the albumin. In some embodiments, the treatment method comprises administering to the individual an effective amount of a composition comprising nanoparticles comprising a limus drug and an albumin, wherein the nanoparticles have an average particle size of no greater than about 200 nm (such as no greater than about 150 nm). In some embodiments, the treatment method comprises administering to the individual an effective amount of a composition comprising nanoparticles comprising a limus drug and an albumin, wherein the nanoparticles comprise a limus drug coated with albumin, wherein the nanoparticles have an average particle size of no greater than about 200 nm (such as no greater than about 150 nm). In some embodiments, the treatment method comprises administering to the individual an effective amount of a composition comprising nanoparticles comprising sirolimus and human albumin, wherein the nanoparticles comprise sirolimus coated with human albumin, wherein the nanoparticles have an average particle size of no greater than about 150 nm (such as no greater than about 120 nm, for example about 100 nm), wherein the weight ratio of human albumin and sirolimus in the composition is about 9:1 or less (such as about 9:1 or about 8:1). In some embodiments, the composition comprises Nab-sirolimus. In some embodiments, the composition is Nab-sirolimus. In some embodiments, the composition is Nab-sirolimus. In some embodiments, the treatment method further comprises administering to the individual an effective amount of another agent (such as BCG and/or mitomycin).

In some embodiments, there is provided a method of determining whether an individual with bladder cancer has responded to a treatment comprising administering to the selected individual an effective amount of a composition comprising nanoparticles comprising an mTOR inhibitor (such as a limus drug), the method comprising assessing the level of one or more biomarkers selected from the group consisting of p-S6K, pAKT, p-4EBP1, Ki67, p53, p63, Stathmin, Tau, SPARC, p73, c-myc, and cyclin D1 in the individual prior to and after the treatment; wherein a decreased level of one or more of the biomarkers after the treatment indicates that the individual has responded to the treatment. In some embodiments, the method further comprises continue to administer to the individual who has responded to the treatment an effective amount of a composition comprising nanoparticles comprising an mTOR inhibitor (such as a limus drug). In some embodiments, the method comprises adjusting the dosage of the mTOR nanoparticle composition. In some embodiments, the biomarker is selected from the group consisting of p-S6K, pAKT, p-4EBP1, and Ki67. In some embodiments, the treatment method comprises administering to the individual an effective amount of a composition comprising nanoparticles comprising a limus drug and an albumin. In some embodiments, the treatment method comprises administering to the individual an effective amount of a composition comprising nanoparticles comprising a limus drug and an albumin, wherein the limus drug in the nanoparticles is coated with the albumin. In some embodiments, the treatment method comprises administering to the individual an effective amount of a composition comprising nanoparticles comprising a limus drug and an albumin, wherein the nanoparticles have an average particle size of no greater than about 200 nm (such as no greater than about 150 nm). In some embodiments, the treatment method comprises administering to the individual an effective amount of a composition comprising nanoparticles comprising a limus drug and an albumin, wherein the nanoparticles comprise a limus drug coated with albumin, wherein the nanoparticles have an average particle size of no greater than about 200 nm (such as no greater than about 150 nm). In some embodiments, the treatment method comprises administering to the individual an effective amount of a composition comprising nanoparticles comprising sirolimus and human albumin, wherein the nanoparticles comprise sirolimus coated with human albumin, wherein the nanoparticles have an average particle size of no greater than about 150 nm (such as no greater than about 120 nm, for example about 100 nm), wherein the weight ratio of human albumin and sirolimus in the composition is about 9:1 or less (such as about 9:1 or about 8:1). In some embodiments, the composition comprises Nab-sirolimus. In some embodiments, the composition is Nab-sirolimus. In some embodiments, the composition is Nab-sirolimus. In some embodiments, the treatment method further comprises administering to the individual an effective amount of another agent (such as BCG and/or mitomycin).

In some embodiments, there is provided a method of treating an individual having bladder cancer, comprising (i) administering to the individual an effective amount of a composition comprising nanoparticles comprising an mTOR inhibitor (such as a limus drug), (ii) assessing the level of one or more biomarkers selected from the group consisting of p-S6K, pAKT, p-4EBP1, Ki67, p53, p63, Stathmin, Tau, SPARC, p73, c-myc, and cyclin D1 in the individual after the treatment; (iii) comparing the levels of the one or more biomarkers with the level of the biomarkers prior to the treatment, and (iv) continue to administer to the individual an effective amount of a composition comprising nanoparticles comprising an mTOR inhibitor (such as a limus drug) if the individual has a decreased level of one or more of the biomarkers after the treatment. In some embodiments, the method comprises adjusting the dosage of the mTOR nanoparticle composition. In some embodiments, the biomarker is selected from the group consisting of p-S6K, pAKT, p-4EBP1, and Ki67. In some embodiments, the treatment method comprises administering to the individual an effective amount of a composition comprising nanoparticles comprising a limus drug and an albumin. In some embodiments, the treatment method comprises administering to the individual an effective amount of a composition comprising nanoparticles comprising a limus drug and an albumin, wherein the limus drug in the nanoparticles is coated with the albumin. In some embodiments, the treatment method comprises administering to the individual an effective amount of a composition comprising nanoparticles comprising a limus drug and an albumin, wherein the nanoparticles have an average particle size of no greater than about 200 nm (such as no greater than about 150 nm). In some embodiments, the treatment method comprises administering to the individual an effective amount of a composition comprising nanoparticles comprising a limus drug and an albumin, wherein the nanoparticles comprise a limus drug coated with albumin, wherein the nanoparticles have an average particle size of no greater than about 200 nm (such as no greater than about 150 nm). In some embodiments, the treatment method comprises administering to the individual an effective amount of a composition comprising nanoparticles comprising sirolimus and human albumin, wherein the nanoparticles comprise sirolimus coated with human albumin, wherein the nanoparticles have an average particle size of no greater than about 150 nm (such as no greater than about 120 nm, for example about 100 nm), wherein the weight ratio of human albumin and sirolimus in the composition is about 9:1 or less (such as about 9:1 or about 8:1). In some embodiments, the composition comprises Nab-sirolimus. In some embodiments, the composition is Nab-sirolimus. In some embodiments, the composition is Nab-sirolimus. In some embodiments, the treatment method further comprises administering to the individual an effective amount of another agent (such as BCG and/or mitomycin).

In some embodiments, there is provided a method of treating an individual having bladder cancer, comprising: (i) assessing the level of one or more biomarkers selected from the group consisting of p-S6K, pAKT, p-4EBP1, Ki67, p53, p63, Stathmin, Tau, SPARC, p73, c-myc, and cyclin D1 in the individual prior to treatment; (ii) administering to the individual an effective amount of a composition comprising nanoparticles comprising an mTOR inhibitor (such as a limus drug), (iii) assessing the level of one or more biomarkers selected from the group consisting of p-S6K, pAKT, p-4EBP1, Ki67, p53, p63, Stathmin, Tau, SPARC, p73, c-myc, and cyclin D1 in the individual after the treatment; (iv) comparing the levels of the one or more biomarkers with the level of the biomarkers prior to the treatment, and (v) continue to administer to the individual an effective amount of a composition comprising nanoparticles comprising an mTOR inhibitor (such as a limus drug) if the individual has a decreased level of one or more of the biomarkers after the treatment. In some embodiments, the method comprises adjusting the dosage of the mTOR nanoparticle composition. In some embodiments, the biomarker is selected from the group consisting of p-S6K, pAKT, p-4EBP1, and Ki67. In some embodiments, the treatment method comprises administering to the individual an effective amount of a composition comprising nanoparticles comprising a limus drug and an albumin. In some embodiments, the treatment method comprises administering to the individual an effective amount of a composition comprising nanoparticles comprising a limus drug and an albumin, wherein the limus drug in the nanoparticles is coated with the albumin. In some embodiments, the treatment method comprises administering to the individual an effective amount of a composition comprising nanoparticles comprising a limus drug and an albumin, wherein the nanoparticles have an average particle size of no greater than about 200 nm (such as no greater than about 150 nm). In some embodiments, the treatment method comprises administering to the individual an effective amount of a composition comprising nanoparticles comprising a limus drug and an albumin, wherein the nanoparticles comprise a limus drug coated with albumin, wherein the nanoparticles have an average particle size of no greater than about 200 nm (such as no greater than about 150 nm). In some embodiments, the treatment method comprises administering to the individual an effective amount of a composition comprising nanoparticles comprising sirolimus and human albumin, wherein the nanoparticles comprise sirolimus coated with human albumin, wherein the nanoparticles have an average particle size of no greater than about 150 nm (such as no greater than about 120 nm, for example about 100 nm), wherein the weight ratio of human albumin and sirolimus in the composition is about 9:1 or less (such as about 9:1 or about 8:1). In some embodiments, the composition comprises Nab-sirolimus. In some embodiments, the composition is Nab-sirolimus. In some embodiments, the composition is Nab-sirolimus. In some embodiments, the treatment method further comprises administering to the individual an effective amount of another agent (such as BCG and/or mitomycin).

The methods described herein in some embodiments comprise determining the levels of one or more biomarkers in an individual. In some embodiments, the level is the activity level of a biomarker in a sample. In some embodiments the level is an expression level. In some embodiments the level is a measure of a protein present in a cell (for example the surface of a cell), a sample, or a tumor. In some embodiments, the level is based on a mutation or polymorphism in the biomarker gene that correlates with the protein or mRNA level of a biomarker. In some embodiments, the level is the protein expression level. In some embodiments, the level is the mRNA level.

Levels of biomarker in an individual may be determined based on a sample (e.g., sample from the individual or reference sample). In some embodiments, the sample is from a tissue, organ, cell, or tumor. In some embodiments, the sample is a biological sample. In some embodiments, the biological sample is a biological fluid sample or a biological tissue sample. In further embodiments, the biological fluid sample is a bodily fluid. Bodily fluids include, but are not limited to, blood, urine, lymph, saliva, semen, peritoneal fluid, cerebrospinal fluid, breast milk, and pleural effusion. In some embodiments, the sample is a blood sample which includes, for example, platelets, lymphocytes, polymorphonuclear cells, macrophages, and erythrocytes. In some embodiments, the sample is a urine sample.

In some embodiments, the sample is a tumor tissue, normal tissue adjacent to said tumor, normal tissue distal to said tumor, blood sample, or other biological sample. In some embodiments, the sample is a fixed sample. Fixed samples include, but are not limited to, a formalin fixed sample, a paraffin-embedded sample, or a frozen sample. In some embodiments, the sample is a biopsy containing cancer cells. In some embodiments, the sample is a biopsy sample obtained from a cystoscopy. In some embodiments, the sample is a biopsy sample obtained from a trans urethral resection of the bladder tumor (TURBT). In a further embodiment, the biopsy is a fine needle aspiration of bladder cancer cells. In a further embodiment, the biopsy is laparoscopy obtained bladder cancer cells. In some embodiments, the biopsied cells are centrifuged into a pellet, fixed, and embedded in paraffin. In some embodiments, the biopsied cells are flash frozen. In some embodiments, the biopsied cells are mixed with an antibody that recognizes the biomarker. In some embodiments, a biopsy is taken to determine whether an individual has cancer and is then used as a sample. In some embodiments, the sample comprises surgically obtained tumor cells. In some embodiments, samples may be obtained at different times than when the determining of biomarker levels occurs.

In some embodiments, the sample comprises a circulating metastatic bladder cancer cell. In some embodiments, the sample is obtained by sorting bladder circulating tumor cells (CTCs) from blood. In a further embodiment, the CTCs have detached from a primary tumor and circulate in a bodily fluid. In yet a further embodiment, the CTCs have detached from a primary tumor and circulate in the bloodstream. In a further embodiment, the CTCs are an indication of metastasis.

In some embodiments, the level of one biomarker (such as p-S6K) is determined. In some embodiments, the levels of two or more biomarkers are determined; for example, one or more biomarkers selected from the group consisting of p-S6K, pAKT, p-4EBP1, and Ki67 can be determined. The one or more biomarkers include, for example, at least two or more biomarkers, at least three or more biomarkers, at least four or more biomarkers, at least five or more biomarkers, or at least six or more biomarkers described herein. In some embodiments, the one or more biomarkers include p-S6K.

In some embodiments, the protein expression level of the biomarker is determined. In some embodiments, the mRNA level of the biomarker is determined. In some embodiments, the level of the biomarker is determined by an immunohistochemistry method.

The levels of a biomarker may be a high level or a low level as compared to a control sample. In some embodiments, the level of the biomarker in an individual is compared to the level of the biomarker in a control sample. In some embodiments the level of the biomarker in a subject is compared to the level of the biomarker in multiple control samples. In some embodiments, multiple control samples are used to generate a statistic that is used to classify the level of the biomarker in an individual with cancer.

In some embodiments, the DNA copy number is determined, and a high DNA copy number for the gene encoding the biomarker (for example a high DNA copy number as compared to a control sample) is indicative of a high level of the biomarker.

The classification or ranking of the biomarker level (i.e., high or low) may be determined relative to a statistical distribution of control levels. In some embodiments, the classification or ranking is relative to a control sample obtained from the individual. In some embodiment the levels of the biomarker (such as p-S6K) is classified or ranked relative to a statistical distribution of control levels. In some embodiments, the level of the biomarker (such as p-S6K1) is classified or ranked relative to the level from a control sample obtained from the subject.

Control samples can be obtained using the same sources and methods as non-control samples. In some embodiments, the control sample is obtained from a different individual (for example an individual not having cancer and/or an individual sharing similar ethnic, age, and gender identity). In some embodiments when the sample is a tumor tissue sample, the control sample may be a non-cancerous sample from the same individual. In some embodiments, multiple control samples (for example from different individuals) are used to determine a range of levels of biomarkers in a particular tissue, organ, or cell population. In some embodiments, the control sample is a cultured tissue or cell that has been determined to be a proper control. In some embodiments, the control is a cell that does not express the biomarker. In some embodiments, a clinically accepted normal level in a standardized test is used as a control level for determining the biomarker level. In some embodiments, the reference level of biomarker (e.g., p-S6K1) in the subject is classified as high, medium or low according to a scoring system, such as an immunohistochemistry-based scoring system. In some embodiments, the reference level of biomarker (e.g., p-S6K1) in the subject is classified as a low sample when the score is less than or equal to the overall median score.

In some embodiments, the biomarker level is determined by measuring the level of a biomarker in an individual and comparing to a control or reference (e.g., the median level for the given patient population or level of a second individual). For example, if the level of a biomarker (e.g., p-S6K1) for the single individual is determined to be above the median level of the patient population, that individual is determined to have a high level of the biomarker. Alternatively, if the level of a biomarker for the single individual is determined to be below the median level of the patient population, that individual is determined to have a low level of the biomarker. In some embodiments, the individual is compared to a second individual and/or a patient population which is responsive to treatment. In some embodiments, the individual is compared to a second individual and/or a patient population which is not responsive to treatment. In any of the embodiments herein, the levels can be determined by measuring the level of a nucleic acid encoding a biomarker (e.g., p-S6K1). For example, if the level of an mRNA encoding a biomarker for the single individual is determined to be above the median level of the patient population, that individual is determined to have a high level of an mRNA encoding the biomarker. Alternatively, if the level of mRNA encoding the biomarker for the single individual is determined to be below the median level of the patient population, that individual is determined to have a low level of an mRNA encoding the biomarker.

In some embodiments, the reference level of a biomarker is determined by obtaining a statistical distribution of biomarker levels.

In some embodiments, bioinformatics methods are used for the determination and classification of the levels of the biomarker. Numerous alternative bioinformatics approaches have been developed to assess gene set expression profiles using gene expression profiling data. Methods include but are not limited to those described in Segal, E. et al. Nat. Genet. 34:66-176 (2003); Segal, E. et al. Nat. Genet. 36:1090-1098 (2004); Barry, W. T. et al. Bioinformatics 21:1943-1949 (2005); Tian, L. et al. Proc Nat'l Acad Sci USA 102:13544-13549 (2005); Novak B A and Jain A N. Bioinformatics 22:233-41 (2006); Maglietta R et al. Bioinformatics 23:2063-72 (2007); Bussemaker H J, BMC Bioinformatics 8 Suppl 6:S6 (2007).

In some embodiments, mRNA level is determined, and a low level is an mRNA level less than about 1.1, 1.2, 1.3, 1.5, 1.7, 2, 2.2, 2.5, 2.7, 3, 5, 7, 10, 20, 50, 70, 100, 200, 500, 1000 times or less than 1000 times to that of what is considered as clinically normal or to the level obtained from a control. In some embodiments, high level is an mRNA level more than about 1.1, 1.2, 1.3, 1.5, 1.7, 2, 2.2, 2.5, 2.7, 3, 5, 7, 10, 20, 50, 70, 100, 200, 500, 1000 times or more than 1000 times to that of what is considered as clinically normal or to the level obtained from a control.

In some embodiments, protein expression level is determined, for example by immunohistochemistry. For example, the criteria for low or high levels can be made based on the number of positive staining cells and/or the intensity of the staining, for example by using an antibody that specifically recognizes the biomarker protein (e.g., p-S6K). In some embodiments, the level is low if less than about 1%, 5%, 10%, 15%, 20%, 25%, 30%, 35%, 40%, 45%, or 50% cells have positive staining. In some embodiments, the level is low if the staining is 1%, 5%, 10%, 15%, 20%, 25%, 30%, 35%, 40%, 45%, or 50% less intense than a positive control staining.

In some embodiments, the level is high if more than about 40%, 45%, 50%, 55%, 60%, 65%, 70%, 75%, 80%, 85%, or 90%, cells have positive staining. In some embodiments, the level is high if the staining is as intense as positive control staining. In some embodiments, the level is high if the staining is 80%, 85%, or 90% as intense as positive control staining.

In some embodiments, strong staining, moderate staining, and weak staining are calibrated levels of staining, wherein a range is established and the intensity of staining is binned within the range. In some embodiments, strong staining is staining above the 75th percentile of the intensity range, moderate staining is staining from the 25th to the 75th percentile of the intensity range, and low staining is staining is staining below the 25th percentile of the intensity range. In some aspects one skilled in the art, and familiar with a particular staining technique, adjusts the bin size and defines the staining categories.

Further provided herein are methods of directing treatment of a bladder cancer by delivering a sample to a diagnostic lab for determination of biomarker levels; providing a control sample with a known level of a biomarker; providing an antibody to a biomarker (e.g., p-S6K1 antibody); subjecting the sample and control sample to binding by the antibody, and/or detecting a relative amount of antibody binding, wherein the level of the sample is used to provide a conclusion that a patient should receive a treatment with any one of the methods described herein.

Also provided herein are methods of directing treatment of a disease, further comprising reviewing or analyzing data relating to the presence (or level) of a biomarker (e.g., p-S6K1) in a sample; and providing a conclusion to an individual about the likelihood or suitability of the individual to respond to a treatment, a health care provider or a health care manager, the conclusion being based on the review or analysis of data. In one aspect of the invention a conclusion is the transmission of the data over a network.

Dosing and Method of Administering the Nanoparticle Compositions

The dose of the mTOR nanoparticles (such as a limus nanoparticle compositions) administered to an individual (such as a human) may vary with the particular composition, the mode of administration, and the type of bladder cancer being treated. In some embodiments, the amount of the composition is effective to result in an objective response (such as a partial response or a complete response). In some embodiments, the amount of the mTOR nanoparticle composition (such as a limus nanoparticle composition) is sufficient to result in a complete response in the individual. In some embodiments, the amount of the mTOR nanoparticle composition (such as a limus nanoparticle composition) is sufficient to result in a partial response in the individual. In some embodiments, the amount of the mTOR nanoparticle composition (such as a limus nanoparticle composition) administered (for example when administered alone) is sufficient to produce an overall response rate of more than about any of 20%, 30%, 40%, 50%, 60%, or 64% among a population of individuals treated with the mTOR nanoparticle composition (such as a limus nanoparticle composition). Responses of an individual to the treatment of the methods described herein can be determined, for example, based on RECIST levels, cystoscopy (with or without biopsy), biopsy, cytology, and CT imaging.

In some embodiments, the amount of the mTOR nanoparticle composition (such as a limus nanoparticle composition) is sufficient to produce a negative biopsy in the individual. In some embodiments, the amount of the mTOR nanoparticle composition (such as a limus nanoparticle composition) is sufficient to produce a response (partial or complete) based on urine cytology. In some embodiments, the amount of the mTOR nanoparticle composition (such as a limus nanoparticle composition) is sufficient to produce both a negative biopsy and a response (partial or complete) based on urine cytology.

In some embodiments, the amount of the mTOR nanoparticle composition (such as a limus nanoparticle composition) is not sufficient to cause systemic toxicity, such as cystitis, hematuria, dysuria, urinary retention, urinary frequency/urgency, or bladder spasm.

In some embodiments, the amount of the composition is sufficient to prolong progress-free survival of the individual. In some embodiments, the amount of the composition is sufficient to prolong overall survival of the individual. In some embodiments, the amount of the composition (for example when administered alone) is sufficient to produce clinical benefit of more than about any of 50%, 60%, 70%, or 77% among a population of individuals treated with the mTOR nanoparticle composition (such as a limus nanoparticle composition).

In some embodiments, the amount of the composition is an amount sufficient to decrease the size of a tumor, decrease the number of cancer cells, or decrease the growth rate of a tumor by at least about any of 10%, 20%, 30%, 40%, 50%, 60%, 70%, 80%, 90%, 95% or 100% compared to the corresponding tumor size, number of bladder cancer cells, or tumor growth rate in the same subject prior to treatment or compared to the corresponding activity in other subjects not receiving the treatment. Standard methods can be used to measure the magnitude of this effect, such as in vitro assays with purified enzyme, cell-based assays, animal models, or human testing.

In some embodiments, the amount of the mTOR inhibitor (such as a limus drug, for example sirolimus) in the composition is below the level that induces a toxicological effect (i.e., an effect above a clinically acceptable level of toxicity) or is at a level where a potential side effect can be controlled or tolerated when the composition is administered to the individual.

In some embodiments, the amount of the composition is close to a maximum tolerated dose (MTD) of the composition following the same dosing regime. In some embodiments, the amount of the composition is more than about any of 80%, 90%, 95%, or 98% of the MTD.

In some embodiments, the amount of an mTOR inhibitor (such as a limus drug, e.g., sirolimus) in the composition is included in any of the following ranges: about 0.1 mg to about 1000 mg, about 0.1 mg to about 2.5 mg, about 0.5 mg to about 5 mg, about 5 mg to about 10 mg, about 10 mg to about 15 mg, about 15 mg to about 20 mg, about 20 mg to about 25 mg, about 20 mg to about 50 mg, about 25 mg to about 50 mg, about 50 mg to about 75 mg, about 50 mg to about 100 mg, about 75 mg to about 100 mg, about 100 mg to about 125 mg, about 125 mg to about 150 mg, about 150 mg to about 175 mg, about 175 mg to about 200 mg, about 200 mg to about 225 mg, about 225 mg to about 250 mg, about 250 mg to about 300 mg, about 300 mg to about 350 mg, about 350 mg to about 400 mg, about 400 mg to about 450 mg, or about 450 mg to about 500 mg, about 500 mg to about 600 mg, about 600 mg to about 700 mg, about 700 mg to about 800 mg, about 800 mg to about 900 mg, or about 900 mg to about 1000 mg. In some embodiments, the amount of an mTOR inhibitor (such as a limus drug, e.g., sirolimus) in the effective amount of the composition (e.g., a unit dosage form) is in the range of about 5 mg to about 500 mg, such as about 30 mg to about 400 mg, 30 mg to about 300 mg, or about 50 mg to about 200 mg. In some embodiments, the amount of an mTOR inhibitor (such as a limus drug, e.g., sirolimus) in the effective amount of the composition (e.g., a unit dosage form) is in the range of about 150 mg to about 500 mg, including for example, about 150 mg, about 225 mg, about 250 mg, about 300 mg, about 325 mg, about 350 mg, about 375 mg, about 400 mg, about 425 mg, about 450 mg, about 475 mg, or about 500 mg. In some embodiments, the concentration of the mTOR inhibitor (such as a limus drug, e.g., sirolimus) in the composition is dilute (about 0.1 mg/ml) or concentrated (about 100 mg/ml), including for example any of about 0.1 mg/ml to about 50 mg/ml, about 0.1 mg/ml to about 20 mg/ml, about 1 mg/ml to about 10 mg/ml, about 2 mg/ml to about 8 mg/ml, about 4 mg/ml to about 6 mg/ml, or about 5 mg/ml. In some embodiments, the concentration of the mTOR inhibitor (such as a limus drug, e.g., sirolimus) is at least about any of 0.5 mg/ml, 1.3 mg/ml, 1.5 mg/ml, 2 mg/ml, 3 mg/ml, 4 mg/ml, 5 mg/ml, 6 mg/ml, 7 mg/ml, 8 mg/ml, 9 mg/ml, 10 mg/ml, 15 mg/ml, 20 mg/ml, 25 mg/ml, 30 mg/ml, 40 mg/ml, or 50 mg/ml.

In some embodiments of any of the above aspects, the amount of an mTOR inhibitor (such as a limus drug, e.g., sirolimus) in the composition includes at least about any of 1 mg/kg, 2.5 mg/kg, 3.5 mg/kg, 5 mg/kg, 6.5 mg/kg, 7.5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 55 mg/kg, or 60 mg/kg. In various embodiments, the effective amount of an mTOR inhibitor (such as a limus drug, e.g., sirolimus) in the composition includes less than about any of 350 mg/kg, 300 mg/kg, 250 mg/kg, 200 mg/kg, 150 mg/kg, 100 mg/kg, 50 mg/kg, 25 mg/kg, 20 mg/kg, 10 mg/kg, 7.5 mg/kg, 6.5 mg/kg, 5 mg/kg, 3.5 mg/kg, 2.5 mg/kg, or 1 mg/kg of an mTOR inhibitor (such as a limus drug, e.g., sirolimus).

Exemplary dosing frequencies for the administration of the nanoparticle compositions include, but are not limited to, daily, every two days, every three days, every four days, every five days, every six days, weekly without break, three out of four weeks, once every three weeks, once every two weeks, or two out of three weeks. In some embodiments, the composition is administered about once every 2 weeks, once every 3 weeks, once every 4 weeks, once every 6 weeks, or once every 8 weeks. In some embodiments, the composition is administered at least about any of 1×, 2×, 3×, 4×, 5×, 6×, or 7× (i.e., daily) a week. In some embodiments, the intervals between each administration are less than about any of 6 months, 3 months, 1 month, 20 days, 15, days, 14 days, 13 days, 12 days, 11 days, 10 days, 9 days, 8 days, 7 days, 6 days, 5 days, 4 days, 3 days, 2 days, or 1 day. In some embodiments, the intervals between each administration are more than about any of 1 month, 2 months, 3 months, 4 months, 5 months, 6 months, 8 months, or 12 months. In some embodiments, there is no break in the dosing schedule. In some embodiments, the interval between each administration is no more than about a week. In some embodiments, the composition is administered weekly. In some embodiments, the composition is administered twice every week.

The administration of the composition can be extended over an extended period of time, such as from about a month up to about seven years. In some embodiments, the composition is administered over a period of at least about any of 2, 3, 4, 5, 6, 7, 8, 9, 10, 11, 12, 18, 24, 30, 36, 48, 60, 72, or 84 months. In some embodiments, the composition is administered weekly for 6 weeks, optionally followed by monthly maintenance thereafter.

In some embodiments, the individual is treated for at least about any of one, two, three, four, five, six, seven, eight, nine, or ten treatment cycles.

The mTOR nanoparticle composition (such as a limus nanoparticle composition) can be administered to an individual (such as human) via various routes, including, for example, intravenous, intra-arteri al, intraperitoneal, intrapulmonary, oral, inhalation, intravesicular, intramuscular, intra-tracheal, subcutaneous, intraocular, intrathecal, transmucosal, and transdermal. In some embodiments, sustained continuous release formulation of the composition may be used. In some embodiments, the composition is administered intravenously. In some embodiments, the composition is administered intravesicularly. In some embodiments, the composition is administered intraarterially. In some embodiments, the composition is administered intraperitoneally.

In some embodiments when the limus nanoparticle composition is administered intravesicularly, the dosage of an mTOR inhibitor (such as a limus drug, e.g., sirolimus) in a nanoparticle composition can be in the range of about 30 mg to about 400 mg in volume of about 20 ml to about 150 ml, for example retained in the bladder for about 30 minutes to about 4 hours. In some embodiments, the nanoparticle composition is retained in the bladder for about 30 minutes to about 4 hours, including for example about 30 minutes to about 1 hour, about 1 hour to about 2 hours, about 2 hours to about 3 hours, or about 3 hours to about 4 hours.

In some embodiments, the dosage of an mTOR inhibitor (such as a limus drug, e.g., sirolimus) is about 100 mg to about 400 mg, for example about 100 mg, about 200 mg, about 300 mg, or about 400 mg. In some embodiments, the limus drug is administered at about 100 mg weekly, about 200 mg weekly, about 300 mg weekly, about 100 mg twice weekly, or about 200 mg twice weekly. In some embodiments, the administration is further followed by a monthly maintenance dose (which can be the same or different from the weekly doses).

In some embodiments when the limus nanoparticle composition is administered intravenously, the dosage of an mTOR inhibitor (such as a limus drug, e.g., sirolimus) in a nanoparticle composition can be in the range of about 30 mg to about 400 mg. The compositions described herein allow infusion of the composition to an individual over an infusion time that is shorter than about 24 hours. For example, in some embodiments, the composition is administered over an infusion period of less than about any of 24 hours, 12 hours, 8 hours, 5 hours, 3 hours, 2 hours, 1 hour, 30 minutes, 20 minutes, or 10 minutes. In some embodiments, the composition is administered over an infusion period of about 30 minutes to about 40 minutes.

Modes of Administration of Combination Therapies

The dosing regimens described in the section above apply to both monotherapy and combination therapy settings. The modes of administration for combination therapy methods are further described below.

In some embodiments, the nanoparticle composition and the other agent (including the specific chemotherapeutic agents described herein) are administered simultaneously. When the drugs are administered simultaneously, the drug in the nanoparticles and the other agent may be contained in the same composition (e.g., a composition comprising both the nanoparticles and the other agent) or in separate compositions (e.g., the nanoparticles are contained in one composition and the other agent is contained in another composition).

In some embodiments, the nanoparticle composition and the other agent are administered sequentially. Either the nanoparticle composition or the other agent may be administered first. The nanoparticle composition and the other agent are contained in separate compositions, which may be contained in the same or different packages.

In some embodiments, the administration of the nanoparticle composition and the other agent are concurrent, i.e., the administration period of the nanoparticle composition and that of the other agent overlap with each other. In some embodiments, the nanoparticle composition is administered for at least one cycle (for example, at least any of 2, 3, or 4 cycles) prior to the administration of the other agent. In some embodiments, the other agent is administered for at least any of one, two, three, or four weeks. In some embodiments, the administrations of the nanoparticle composition and the other agent are initiated at about the same time (for example, within any one of 1, 2, 3, 4, 5, 6, or 7 days). In some embodiments, the administrations of the nanoparticle composition and the other agent are terminated at about the same time (for example, within any one of 1, 2, 3, 4, 5, 6, or 7 days). In some embodiments, the administration of the other agent continues (for example for about any one of 1, 2, 3, 4, 5, 6, 7, 8, 9, 10, 11, or 12 months) after the termination of the administration of the nanoparticle composition. In some embodiments, the administration of the other agent is initiated after (for example after about any one of 1, 2, 3, 4, 5, 6, 7, 8, 9, 10, 11, or 12 months) the initiation of the administration of the nanoparticle composition. In some embodiments, the administrations of the nanoparticle composition and the other agent are initiated and terminated at about the same time. In some embodiments, the administrations of the nanoparticle composition and the other agent are initiated at about the same time and the administration of the other agent continues (for example for about any one of 1, 2, 3, 4, 5, 6, 7, 8, 9, 10, 11, or 12 months) after the termination of the administration of the nanoparticle composition. In some embodiments, the administration of the nanoparticle composition and the other agent stop at about the same time and the administration of the other agent is initiated after (for example after about any one of 1, 2, 3, 4, 5, 6, 7, 8, 9, 10, 11, or 12 months) the initiation of the administration of the nanoparticle composition.

In some embodiments, the administration of the nanoparticle composition and the other agent are non-concurrent. For example, in some embodiments, the administration of the nanoparticle composition is terminated before the other agent is administered. In some embodiments, the administration of the other agent is terminated before the nanoparticle composition is administered. The time period between these two non-concurrent administrations can range from about two to eight weeks, such as about four weeks.

The dosing frequency of the drug-containing nanoparticle composition and the other agent may be adjusted over the course of the treatment, based on the judgment of the administering physician. When administered separately, the drug-containing nanoparticle composition and the other agent can be administered at different dosing frequency or intervals. For example, the drug-containing nanoparticle composition can be administered weekly, while a chemotherapeutic agent can be administered more or less frequently. In some embodiments, sustained continuous release formulation of the drug-containing nanoparticle and/or chemotherapeutic agent may be used. Various formulations and devices for achieving sustained release are known in the art. A combination of the administration configurations described herein can also be used.

The nanoparticle composition and the other agent can be administered using the same route of administration or different routes of administration. In some embodiments (for both simultaneous and sequential administrations), the limus drug in the nanoparticle composition and the other agent are administered at a predetermined ratio. For example, in some embodiments, the ratio by weight of the limus drug in the nanoparticle composition and the other agent is about 1 to 1. In some embodiments, the weight ratio may be between about 0.001 to about 1 and about 1000 to about 1, or between about 0.01 to about 1 and 100 to about 1. In some embodiments, the ratio by weight of the limus drug in the nanoparticle composition and the other agent is less than about any of 100:1, 50:1, 30:1, 10:1, 9:1, 8:1, 7:1, 6:1, 5:1, 4:1, 3:1, 2:1, and 1:1 In some embodiments, the ratio by weight of the limus drug in the nanoparticle composition and the other agent is more than about any of 1:1, 2:1, 3:1, 4:1, 5:1, 6:1, 7:1, 8:1, 9:1, 30:1, 50:1, 100:1. Other ratios are contemplated.

The doses required for the limus drug and/or the other agent may (but not necessarily) be lower than what is normally required when each agent is administered alone. Thus, in some embodiments, a subtherapeutic amount of the drug in the nanoparticle composition and/or the other agent is administered. "Subtherapeutic amount" or "subtherapeutic level" refer to an amount that is less than the therapeutic amount, that is, less than the amount normally used when the drug in the nanoparticle composition and/or the other agent are administered alone. The reduction may be reflected in terms of the amount administered at a given administration and/or the amount administered over a given period of time (reduced frequency).

In some embodiments, enough chemotherapeutic agent is administered so as to allow reduction of the normal dose of the drug in the nanoparticle composition required to effect the same degree of treatment by at least about any of 5%, 10%, 20%, 30%, 50%, 60%, 70%, 80%, 90%, or more. In some embodiments, enough drug in the nanoparticle composition is administered so as to allow reduction of the normal dose of the other agent required to effect the same degree of treatment by at least about any of 5%, 10%, 20%, 30%, 50%, 60%, 70%, 80%, 90%, or more.

In some embodiments, the dose of both the limus drug in the nanoparticle composition and the other agent are reduced as compared to the corresponding normal dose of each when administered alone. In some embodiments, both the limus drug in the nanoparticle composition and the other agent are administered at a subtherapeutic, i.e., reduced, level. In some embodiments, the dose of the nanoparticle composition and/or the other agent is substantially less than the established maximum toxic dose (MTD). For example, the dose of the nanoparticle composition and/or the other agent is less than about 50%, 40%, 30%, 20%, or 10% of the MTD.

A combination of the administration configurations described herein can be used. The combination therapy methods described herein may be performed alone or in conjunction with another therapy, such as chemotherapy, radiation therapy, surgery, hormone therapy, gene therapy, immunotherapy, chemoimmunotherapy, hepatic artery-based therapy, cryotherapy, ultrasound therapy, liver transplantation, local ablative therapy, radiofrequency ablation therapy, photodynamic therapy, and the like. Additionally, a person having a greater risk of developing the bladder cancer may receive treatments to inhibit and/or delay the development of the disease.

The other agent described herein can be administered to an individual (such as human) via various routes, such as parenterally, including intravenous, intra-arterial, intraperitoneal, intrapulmonary, oral, inhalation, intravesicular, intramuscular, intra-tracheal, subcutaneous, intraocular, intrathecal, or transdermal. In some embodiments, the other agent is administrated intravenously. In some embodiments, the nanoparticle composition is administered orally.

The dosing frequency of the other agent can be the same or different from that of the nanoparticle composition. Exemplary frequencies are provided above. As further example, the other agent can be administered three times a day, two times a day, daily, 6 times a week, 5 times a week, 4 times a week, 3 times a week, two times a week, weekly. In some embodiments, the other agent is administered twice daily or three times daily. Exemplary amounts of the other agent include, but are not limited to, any of the following ranges: about 0.5 mg to about 5 mg, about 5 mg to about 10 mg, about 10 mg to about 15 mg, about 15 mg to about 20 mg, about 20 mg to about 25 mg, about 20 mg to about 50 mg, about 25 mg to about 50 mg, about 50 mg to about 75 mg, about 50 mg to about 100 mg, about 75 mg to about 100 mg, about 100 mg to about 125 mg, about 125 mg to about 150 mg, about 150 mg to about 175 mg, about 175 mg to about 200 mg, about 200 mg to about 225 mg, about 225 mg to about 250 mg, about 250 mg to about 300 mg, about 300 mg to about 350 mg, about 350 mg to about 400 mg, about 400 mg to about 450 mg, or about 450 mg to about 500 mg. For example, the other agent can be administered at a dose of about 1 mg/kg to about 200 mg/kg (including for example about 1 mg/kg to about 20 mg/kg, about 20 mg/kg to about 40 mg/kg, about 40 mg/kg to about 60 mg/kg, about 60 mg/kg to about 80 mg/kg, about 80 mg/kg to about 100 mg/kg, about 100 mg/kg to about 120 mg/kg, about 120 mg/kg to about 140 mg/kg, about 140 mg/kg to about 200 mg/kg).

In some embodiments the other agent is BCG. In some embodiments, the dose of BCG is about 1 mg to about 5 mg, about 5 mg to about 10 mg, about 10 mg to about 20 mg, about 20 mg to about 30 mg, about 30 mg to about 40 mg, about 40 mg to about 50 mg, about 50 mg to about 60 mg, about 60 mg to about 70 mg, about 70 mg to about 80 mg, about 80 mg to about 90 mg. In some embodiments, the dose of BCG is about $1 \times 10^5$ CFU/ml to about $1 \times 10^7$ CFU/ml, including for example about $1$-$8 \times 10^6$ CFU/ml, such as about $2 \times 10^6$, about $3 \times 10^6$, about $4 \times 10^6$, about $5 \times 10^6$, about $6 \times 10^6$, about $7 \times 10^6$, or about $8 \times 10^6$ CFU/ml. In some embodiments, the BCG is administered intravesicularly. In some embodiments, the BCG is administered weekly. In some embodiments, the amount of limus drug useful for combination with the BCG is about 5 mg to about 500 mg, including for example about 30 mg to about 400 mg, such as about 100 mg to about 200 mg.

In some embodiments, the amount of the mTOR inhibitor (such as limus drug, e.g., sirolimus) in the nanoparticle composition is between about 5 mg to about 500 mg and the amount of the other agent is about 1 mg/kg to about 200 mg/kg (including for example about 1 mg/kg to about 20 mg/kg, about 20 mg/kg to about 40 mg/kg, about 40 mg/kg to about 60 mg/kg, about 60 mg/kg to about 80 mg/kg, about 80 mg/kg to about 100 mg/kg, about 100 mg/kg to about 120 mg/kg, about 120 mg/kg to about 140 mg/kg, about 140 mg/kg to about 200 mg/kg). In some embodiments, the amount of 1 mTOR inhibitor (such as limus drug, e.g., sirolimus) in the nanoparticle composition is between about 30 mg to about 400 mg and the amount of the other agent is about 1 mg/kg to about 200 mg/kg (including for example about 1 mg/kg to about 20 mg/kg, about 20 mg/kg to about 40 mg/kg, about 40 mg/kg to about 60 mg/kg, about 60 mg/kg to about 80 mg/kg, about 80 mg/kg to about 100 mg/kg, about 100 mg/kg to about 120 mg/kg, about 120 mg/kg to about 140 mg/kg, about 140 mg/kg to about 200 mg/kg). In some embodiments, the amount of mTOR inhibitor (such as limus drug, e.g., sirolimus) in the nanoparticle composition is between about 100 mg to about 200 mg and the amount of the other agent is about 1 mg/kg to about 200 mg/kg (including for example about 1 mg/kg to about 20 mg/kg, about 20 mg/kg to about 40 mg/kg, about 40 mg/kg to about 60 mg/kg, about 60 mg/kg to about 80 mg/kg, about 80 mg/kg to about 100 mg/kg, about 100 mg/kg to about 120 mg/kg, about 120 mg/kg to about 140 mg/kg, about 140 mg/kg to about 200 mg/kg).

In some embodiments, the appropriate doses of other agents are approximately those already employed in clinical therapies wherein the other agent are administered alone or in combination with other agents.

Nanoparticle Compositions

The nanoparticle compositions described herein comprise nanoparticles comprising (in various embodiments consisting essentially of) an mTOR inhibitor (such as a limus drug, for example sirolimus). The nanoparticles may further comprise a carrier protein (e.g., an albumin such as human serum albumin or human albumin). Nanoparticles of poorly water soluble drugs have been disclosed in, for example, U.S. Pat. Nos. 5,916,596; 6,506,405; 6,749,868, 6,537,579, 7,820,788, and also in U.S. Pat. Pub. Nos. 2006/0263434, and 2007/0082838; PCT Patent Application WO 08/137148, each of which is incorporated by reference in their entirety.

In some embodiments, the composition comprises nanoparticles with an average or mean diameter of no greater than about 1000 nanometers (nm), such as no greater than about (or less than about) any of 900, 800, 700, 600, 500, 400, 300, 200, and 100 nm. In some embodiments, the average or mean diameters of the nanoparticles is no greater than about 200 nm (such as no greater than about 150 nm). In some embodiments, the average or mean diameters of the nanoparticles is no greater than about 150 nm. In some embodiments, the average or mean diameters of the nanoparticles is no greater than about 100 nm. In some embodiments, the average or mean diameter of the nanoparticles is about 20 nm to about 400 nm. In some embodiments, the average or mean diameter of the nanoparticles is about 40 nm to about 200 nm. In some embodiments, the nanoparticles are sterile-filterable.

In some embodiments, the nanoparticles in the composition described herein have an average diameter of no greater than about 200 nm, including for example no greater than about any one of 190, 180, 170, 160, 150, 140, 130, 120, 110, 100, 90, 80, 70, or 60 nm. In some embodiments, at least about 50% (for example at least about any one of 60%, 70%, 80%, 90%, 95%, or 99%) of the nanoparticles in the composition have a diameter of no greater than about 200 nm, including for example no greater than about any one of 190, 180, 170, 160, 150, 140, 130, 120, 110, 100, 90, 80, 70, or 60 nm. In some embodiments, at least about 50% (for example at least any one of 60%, 70%, 80%, 90%, 95%, or 99%) of the nanoparticles in the composition fall within the range of about 20 nm to about 400 nm, including for example about 20 nm to about 200 nm, about 40 nm to about 200 nm, about 30 nm to about 180 nm, about 40 nm to about 150 nm, about 50 nm to about 120 nm, and about 60 nm to about 100 nm.

In some embodiments, the carrier protein (e.g., an albumin) has sulfhydryl groups that can form disulfide bonds. In some embodiments, at least about 5% (including for example at least about any one of 10%, 15%, 20%, 25%, 30%, 40%, 50%, 60%, 70%, 80%, or 90%) of carrier protein (e.g., an albumin) in the nanoparticle portion of the composition are crosslinked (for example crosslinked through one or more disulfide bonds).

In some embodiments, the nanoparticles comprising the mTOR inhibitor (such as a limus drug, e.g., sirolimus) are coated with a carrier protein (e.g., an albumin such as human albumin or human serum albumin). In some embodiments, the composition comprises an mTOR inhibitor (such as a limus drug, for example sirolimus) in both nanoparticle and non-nanoparticle forms (e.g., in the form of solutions or in the form of soluble carrier protein/nanoparticle complexes), wherein at least about any one of 50%, 60%, 70%, 80%, 90%, 95%, or 99% of the mTOR inhibitor (such as a limus drug, e.g., sirolimus) in the composition are in nanoparticle form. In some embodiments, the mTOR inhibitor (such as a limus drug, e.g., sirolimus) in the nanoparticles constitutes more than about any one of 50%, 60%, 70%, 80%, 90%, 95%, or 99% of the nanoparticles by weight. In some embodiments, the nanoparticles have a non-polymeric matrix. In some embodiments, the nanoparticles comprise a core of an mTOR inhibitor (such as a limus drug, for example sirolimus) that is substantially free of polymeric materials (such as polymeric matrix).

In some embodiments, the composition comprises a carrier protein (e.g., an albumin) in both nanoparticle and non-nanoparticle portions of the composition, wherein at least about any one of 50%, 60%, 70%, 80%, 90%, 95%, or 99% of the carrier protein (e.g., an albumin) in the composition are in non-nanoparticle portion of the composition.

In some embodiments, the weight ratio of an albumin (such as human albumin or human serum albumin) and a mTOR inhibitor in the nanoparticle composition is about 18:1 or less, such as about 15:1 or less, for example about 10:1 or less. In some embodiments, the weight ratio of an albumin (such as human albumin or human serum albumin) and an mTOR inhibitor (such as a limus drug, for example sirolimus) in the composition falls within the range of any one of about 1:1 to about 18:1, about 2:1 to about 15:1, about 3:1 to about 13:1, about 4:1 to about 12:1, about 5:1 to about 10:1. In some embodiments, the weight ratio of an albumin and an mTOR inhibitor (such as a limus drug, for example sirolimus) in the nanoparticle portion of the composition is about any one of 1:2, 1:3, 1:4, 1:5, 1:9, 1:10, 1:15, or less. In some embodiments, the weight ratio of the albumin (such as human albumin or human serum albumin) and the mTOR inhibitor (such as a limus drug, e.g., sirolimus) in the composition is any one of the following: about 1:1 to about 18:1, about 1:1 to about 15:1, about 1:1 to about 12:1, about 1:1 to about 10:1, about 1:1 to about 9:1, about 1:1 to about 8:1, about 1:1 to about 7:1, about 1:1 to about 6:1, about 1:1 to about 5:1, about 1:1 to about 4:1, about 1:1 to about 3:1, about 1:1 to about 2:1, about 1:1 to about 1:1.

In some embodiments, the nanoparticle composition comprises one or more of the above characteristics.

The nanoparticles described herein may be present in a dry formulation (such as lyophilized composition) or suspended in a biocompatible medium. Suitable biocompatible media include, but are not limited to, water, buffered aqueous media, saline, buffered saline, optionally buffered solutions of amino acids, optionally buffered solutions of proteins, optionally buffered solutions of sugars, optionally buffered solutions of vitamins, optionally buffered solutions of synthetic polymers, lipid-containing emulsions, and the like.

In some embodiments, the pharmaceutically acceptable carrier comprises a carrier protein (e.g., an albumin such as human albumin or human serum albumin). Examples of suitable carrier proteins include proteins normally found in blood or plasma, which include, but are not limited to, an albumin, immunoglobulin including IgA, lipoproteins, apolipoprotein B, α-acid glycoprotein, β-2-macroglobulin, thyroglobulin, transferrin, fibronectin, factor VII, factor VIII; factor IX, factor X, and the like. In some embodiments, the carrier protein is non-blood protein, such as casein, α-lactalbumin, β-lactoglobulin. The proteins may either be natural in origin or synthetically prepared. In some embodiments, the protein is an albumin, such as human albumin or human serum albumin. In some embodiments, the albumin is a recombinant albumin.

Human serum albumin (HSA) is a highly soluble globular protein of $M_r$ 65K and consists of 585 amino acids. HSA is the most abundant protein in the plasma and accounts for 70-80% of the colloid osmotic pressure of human plasma. The amino acid sequence of HSA contains a total of 17 disulfide bridges, one free thiol (Cys 34), and a single tryptophan (Trp 214). Intravenous use of HSA solution has been indicated for the prevention and treatment of hypovolumic shock (see, e.g., Tullis, *JAMA*, 237: 355-360, 460-463, (1977)) and Houser et al., *Surgery, Gynecology and Obstetrics*, 150: 811-816 (1980)) and in conjunction with exchange transfusion in the treatment of neonatal hyperbilirubinemia (see, e.g., Finlayson, Seminars in Thrombosis and Hemostasis, 6, 85-120, (1980)). Other albumins are contemplated, such as bovine serum albumin. Use of such non-human albumins could be appropriate, for example, in the context of use of these compositions in non-human mammals, such as the veterinary (including domestic pets and agricultural context). Human serum albumin (HSA) has multiple hydrophobic binding sites (a total of eight for fatty acids, an endogenous ligand of HSA) and binds a diverse set of drugs, especially neutral and negatively charged hydrophobic compounds (Goodman et al., *The Pharmacological Basis of Therapeutics*, 9th ed, McGraw-Hill N.Y. (1996)). Two high affinity binding sites have been proposed in subdomains IIA and IIIA of HSA, which are highly elongated hydrophobic pockets with charged lysine and arginine residues near the surface which function as attachment points for polar ligand features (see, e.g., Fehske et al., *Biochem. Pharmcol.*, 30, 687-92 (198a), Vorum, *Dan. Med. Bull.*, 46, 379-99 (1999), Kragh-Hansen, *Dan. Med. Bull.*, 1441, 131-40 (1990), Curry et al., *Nat. Struct. Biol.*, 5, 827-35 (1998), Sugio et al., *Protein. Eng.*, 12, 439-46 (1999), He et al., *Nature*, 358, 209-15 (199b), and Carter et al., *Adv. Protein. Chem.*, 45, 153-203 (1994)). Sirolimus and propofol have been shown to bind HSA (see, e.g., Paal et al., *Eur. J. Biochem.*, 268(7), 2187-91 (200a), Purcell et al., *Biochim. Biophys. Acta*, 1478(a), 61-8 (2000), Altmayer et al., *Arzneimittelforschung*, 45, 1053-6 (1995), and Garrido et al., *Rev. Esp. Anestestiol. Reanim.*, 41, 308-12 (1994)). In addition, docetaxel has been shown to bind to human plasma proteins (see, e.g., Urien et al., *Invest. New Drugs*, 14(b), 147-51 (1996)).

The carrier protein (e.g., an albumin such as human albumin or human serum albumin) in the composition generally serves as a carrier for the mTOR inhibitor, i.e., the albumin in the composition makes the mTOR inhibitor (such as a limus drug, e.g., sirolimus) more readily suspendable in an aqueous medium or helps maintain the suspension as compared to compositions not comprising a carrier protein. This can avoid the use of toxic solvents (or surfactants) for solubilizing the mTOR inhibitor, and thereby can reduce one or more side effects of administration of the mTOR inhibitor (such as a limus drug, e.g., sirolimus) into an individual (such as a human). Thus, in some embodiments, the composition described herein is substantially free (such as free) of surfactants, such as Cremophor (or polyoxyethylated castor oil, including Cremophor EL® (BASF)). In some embodiments, the nanoparticle composition is substantially free (such as free) of surfactants. A composition is "substantially free of Cremophor" or "substantially free of surfactant" if the amount of Cremophor or surfactant in the composition is not sufficient to cause one or more side effect(s) in an individual when the nanoparticle composition is administered to the individual. In some embodiments, the nanoparticle composition contains less than about any one of 20%, 15%, 10%, 7.5%, 5%, 2.5%, or 1% organic solvent or surfactant. In some embodiments, the carrier protein is an albumin. In some embodiments, the albumin is human albumin or human serum albumin. In some embodiments, the albumin is recombinant albumin.

The amount of a carrier protein such as an albumin in the composition described herein will vary depending on other components in the composition. In some embodiments, the composition comprises a carrier protein such as an albumin in an amount that is sufficient to stabilize the mTOR inhibitor (such as a limus drug, e.g., sirolimus) in an aqueous suspension, for example, in the form of a stable colloidal suspension (such as a stable suspension of nanoparticles). In some embodiments, the carrier protein such as an albumin is in an amount that reduces the sedimentation rate of the mTOR inhibitor (such as a limus drug, e.g., sirolimus) in an aqueous medium. For particle-containing compositions, the amount of the carrier protein such as an albumin also depends on the size and density of nanoparticles of the mTOR inhibitor.

An mTOR inhibitor (such as a limus drug, for example sirolimus) is "stabilized" in an aqueous suspension if it remains suspended in an aqueous medium (such as without visible precipitation or sedimentation) for an extended period of time, such as for at least about any of 0.1, 0.2, 0.25, 0.5, 1, 2, 3, 4, 5, 6, 7, 8, 9, 10, 11, 12, 24, 36, 48, 60, or 72 hours. The suspension is generally, but not necessarily, suitable for administration to an individual (such as human). Stability of the suspension is generally (but not necessarily) evaluated at a storage temperature (such as room temperature (such as 20-25° C.) or refrigerated conditions (such as 4° C.)). For example, a suspension is stable at a storage temperature if it exhibits no flocculation or particle agglomeration visible to the naked eye or when viewed under the optical microscope at 1000 times, at about fifteen minutes after preparation of the suspension. Stability can also be evaluated under accelerated testing conditions, such as at a temperature that is higher than about 40° C.

In some embodiments, the carrier protein (e.g., an albumin) is present in an amount that is sufficient to stabilize the mTOR inhibitor (such as a limus drug, e.g., sirolimus) in an aqueous suspension at a certain concentration. For example, the concentration of the mTOR inhibitor (such as a limus drug, e.g., sirolimus) in the composition is about 0.1 mg/ml to about 100 mg/ml, including for example any of about 0.1 mg/ml to about 50 mg/ml, about 0.1 mg/ml to about 20 mg/ml, about 1 mg/ml to about 10 mg/ml, about 2 mg/ml to about 8 mg/ml, about 4 mg/ml to about 6 mg/ml, or about 5 mg/ml. In some embodiments, the concentration of the mTOR inhibitor (such as a limus drug, e.g., sirolimus) is at least about any of 1.3 mg/ml, 1.5 mg/ml, 2 mg/ml, 3 mg/ml, 4 mg/ml, 5 mg/ml, 6 mg/ml, 7 mg/ml, 8 mg/ml, 9 mg/ml, 10 mg/ml, 15 mg/ml, 20 mg/ml, 25 mg/ml, 30 mg/ml, 40 mg/ml, and 50 mg/ml. In some embodiments, the carrier protein (e.g., an albumin) is present in an amount that avoids use of surfactants (such as Cremophor), so that the composition is free or substantially free of surfactant (such as Cremophor).

In some embodiments, the composition, in liquid form, comprises from about 0.1% to about 50% (w/v) (e.g. about 0.5% (w/v), about 5% (w/v), about 10% (w/v), about 15% (w/v), about 20% (w/v), about 30% (w/v), about 40% (w/v), or about 50% (w/v)) of carrier protein (e.g., an albumin). In some embodiments, the composition, in liquid form, comprises about 0.5% to about 5% (w/v) of carrier protein (e.g., an albumin).

In some embodiments, the weight ratio of a carrier protein (e.g., an albumin) to the mTOR inhibitor (such as a limus drug, e.g., sirolimus) in the nanoparticle composition is such that a sufficient amount of mTOR inhibitor binds to, or is transported by, the cell. While the weight ratio of a carrier protein (e.g., an albumin) to mTOR inhibitor will have to be optimized for different carrier protein (e.g., an albumin) and mTOR inhibitor combinations, generally the weight ratio of carrier protein (e.g., an albumin), to mTOR inhibitor (such as a limus drug, e.g., sirolimus) (w/w) is about 0.01:1 to about 100:1, about 0.02:1 to about 50:1, about 0.05:1 to about 20:1, about 0.1:1 to about 20:1, about 1:1 to about 18:1, about 2:1 to about 15:1, about 3:1 to about 12:1, about 4:1 to about 10:1, about 5:1 to about 9:1, or about 9:1. In some embodiments, the carrier protein (e.g., an albumin) to mTOR inhibitor weight ratio is about any of 18:1 or less, 15:1 or less, 14:1 or less, 13:1 or less, 12:1 or less, 11:1 or less, 10:1 or less, 9:1 or less, 8:1 or less, 7:1 or less, 6:1 or less, 5:1 or less, 4:1 or less, and 3:1 or less. In some embodiments, the carrier protein is an albumin. In some embodiments, the weight ratio of the albumin (such as human albumin or human serum albumin) to the mTOR inhibitor in the composition is any one of the following: about 1:1 to about 18:1, about 1:1 to about 15:1, about 1:1 to about 12:1, about 1:1 to about 10:1, about 1:1 to about 9:1, about 1:1 to about 8:1, about 1:1 to about 7:1, about 1:1 to about 6:1, about 1:1 to about 5:1, about 1:1 to about 4:1, about 1:1 to about 3:1, about 1:1 to about 2:1, about 1:1 to about 1:1.

In some embodiments, the carrier protein (e.g., an albumin) allows the composition to be administered to an individual (such as human) without significant side effects. In some embodiments, the carrier protein (e.g., an albumin such as human serum albumin or human albumin) is in an amount that is effective to reduce one or more side effects of administration of the mTOR inhibitor (such as a limus drug, e.g., sirolimus) to a human. The term "reducing one or more side effects" of administration of the mTOR inhibitor (such as a limus drug, e.g., sirolimus) refers to reduction, alleviation, elimination, or avoidance of one or more undesirable effects caused by the mTOR inhibitor, as well as side effects caused by delivery vehicles (such as solvents that render the limus drugs suitable for injection) used to deliver the mTOR inhibitor. Such side effects include, for example, myelosuppression, neurotoxicity, hypersensitivity, inflammation, venous irritation, phlebitis, pain, skin irritation, peripheral neuropathy, neutropenic fever, anaphylactic reaction, venous thrombosis, extravasation, and combinations thereof. These side effects, however, are merely exemplary and other side effects, or combination of side effects, associated with limus drugs (such as sirolimus) can be reduced.

In some embodiments, the nanoparticle compositions described herein comprises nanoparticles comprising an mTOR inhibitor (such as a limus drug, for example sirolimus) and an albumin (such as human albumin or human serum albumin), wherein the nanoparticles have an average diameter of no greater than about 200 nm. In some embodiments, the nanoparticle compositions described herein comprises nanoparticles comprising an mTOR inhibitor (such as a limus drug, for example sirolimus) and an albumin (such as human albumin or human serum albumin), wherein the nanoparticles have an average diameter of no greater than about 150 nm. In some embodiments, the nanoparticle compositions described herein comprises nanoparticles comprising an mTOR inhibitor (such as a limus drug, for example sirolimus) and an albumin (such as human albumin or human serum albumin), wherein the nanoparticles have an average diameter of no greater than about 150 nm (for example about 100 nm). In some embodiments, the nanoparticle compositions described herein comprises nanoparticles comprising sirolimus and human albumin (such as human serum albumin), wherein the nanoparticles have an average diameter of no greater than about 150 nm (for example about 100 nm).

In some embodiments, the nanoparticle compositions described herein comprises nanoparticles comprising an mTOR inhibitor (such as a limus drug, for example sirolimus) and an albumin (such as human albumin or human serum albumin), wherein the nanoparticles have an average diameter of no greater than about 200 nm, wherein the weight ratio of the albumin and the mTOR inhibitor in the composition is no greater than about 9:1 (such as about 9:1 or about 8:1). In some embodiments, the nanoparticle compositions described herein comprises nanoparticles comprising an mTOR inhibitor (such as a limus drug, for example sirolimus) and an albumin (such as human albumin or human serum albumin), wherein the nanoparticles have an average diameter of no greater than about 150 nm, wherein the weight ratio of the albumin and the mTOR inhibitor in the composition is no greater than about 9:1 (such as about 9:1 or about 8:1). In some embodiments, the nanoparticle compositions described herein comprises nanoparticles comprising an mTOR inhibitor (such as a limus drug, for example sirolimus) and an albumin (such as human albumin or human serum albumin), wherein the nanoparticles have an average diameter of about 150 nm, wherein the weight ratio of the albumin and the mTOR inhibitor in the composition is no greater than about 9:1 (such as about 9:1 or about 8:1). In some embodiments, the nanoparticle compositions described herein comprises nanoparticles comprising sirolimus and human albumin (such as human serum albumin), wherein the nanoparticles have an average diameter of no greater than about 150 nm (for example about 100 nm), wherein the weight ratio of albumin and sirolimus inhibitor in the composition is about 9:1 or about 8:1.

In some embodiments, the nanoparticle compositions described herein comprises nanoparticles comprising an mTOR inhibitor (such as a limus drug, for example sirolimus) coated with an albumin (such as human albumin or human serum albumin). In some embodiments, the nanoparticle compositions described herein comprises nanoparticles comprising an mTOR inhibitor (such as a limus drug, for example sirolimus) coated with an albumin (such as human albumin or human serum albumin), wherein the nanoparticles have an average diameter of no greater than about 200 nm. In some embodiments, the nanoparticle compositions described herein comprises nanoparticles comprising an mTOR inhibitor (such as a limus drug, for example sirolimus) coated with an albumin (such as human albumin or human serum albumin), wherein the nanoparticles have an average diameter of no greater than about 150 nm. In some embodiments, the nanoparticle compositions described herein comprises nanoparticles comprising an mTOR inhibitor (such as a limus drug, for example sirolimus) coated with an albumin (such as human albumin or human serum albumin), wherein the nanoparticles have an average diameter of no greater than about 150 nm (for example about 100 nm). In some embodiments, the nanoparticle compositions described herein comprises nanoparticles comprising sirolimus coated with human albumin (such as human serum albumin), wherein the nanoparticles have an average diameter of no greater than about 150 nm (for example about 100 nm).

In some embodiments, the nanoparticle compositions described herein comprises nanoparticles comprising an mTOR inhibitor (such as a limus drug, for example sirolimus) coated with an albumin (such as human albumin or human serum albumin), wherein the weight ratio of the albumin and the mTOR inhibitor in the composition is no greater than about 9:1 (such as about 9:1 or about 8:1). In some embodiments, the nanoparticle compositions described herein comprises nanoparticles comprising an mTOR inhibitor (such as a limus drug, for example sirolimus) coated with an albumin (such as human albumin or human serum albumin), wherein the nanoparticles have an average diameter of no greater than about 200 nm, wherein the weight ratio of the albumin and the mTOR inhibitor in the composition is no greater than about 9:1 (such as about 9:1 or about 8:1). In some embodiments, the nanoparticle compositions described herein comprises nanoparticles comprising an mTOR inhibitor (such as a limus drug, for example sirolimus) coated with an albumin (such as human albumin or human serum albumin), wherein the nanoparticles have an average diameter of no greater than about 150 nm, wherein the weight ratio of the albumin and the mTOR inhibitor in the composition is no greater than about 9:1 (such as about 9:1 or about 8:1). In some embodiments, the nanoparticle compositions described herein comprises nanoparticles comprising an mTOR inhibitor (such as a limus drug, for example sirolimus) coated with an albumin (such as human albumin or human serum albumin), wherein the nanoparticles have an average diameter of about 150 nm, wherein the weight ratio of the albumin and the mTOR inhibitor in the composition is no greater than about 9:1 (such as about 9:1 or about 8:1). In some embodiments, the nanoparticle compositions described herein comprises nanoparticles comprising sirolimus coated with human albumin (such as human serum albumin), wherein the nanoparticles have an average diameter of no greater than about 150 nm (for example about 100 nm), wherein the weight ratio of albumin and the sirolimus in the composition is about 9:1 or about 8:1.

In some embodiments, the nanoparticle compositions described herein comprises nanoparticles comprising an mTOR inhibitor (such as a limus drug, for example sirolimus) stabilized by an albumin (such as human albumin or human serum albumin). In some embodiments, the nanoparticle compositions described herein comprises nanoparticles comprising an mTOR inhibitor (such as a limus drug, for example sirolimus) stabilized by an albumin (such as human albumin or human serum albumin), wherein the nanoparticles have an average diameter of no greater than about 200 nm. In some embodiments, the nanoparticle compositions described herein comprises nanoparticles comprising an mTOR inhibitor (such as a limus drug, for example sirolimus) stabilized by an albumin (such as human albumin or human serum albumin), wherein the nanoparticles have an average diameter of no greater than about 150 nm. In some embodiments, the nanoparticle compositions described herein comprises nanoparticles comprising an mTOR inhibitor (such, as a limus drug, for example sirolimus) stabilized by an albumin (such as human albumin or human serum albumin), wherein the nanoparticles have an average diameter of no greater than about 150 nm (for example about 100 nm). In some embodiments, the nanoparticle compositions described herein comprises nanoparticles comprising sirolimus stabilized by human albumin (such as human serum albumin), wherein the nanoparticles have an average diameter of no greater than about 150 nm (for example about 100 nm).

In some embodiments, the nanoparticle compositions described herein comprises nanoparticles comprising an mTOR inhibitor (such as a limus drug, for example sirolimus) stabilized by an albumin (such as human albumin or human serum albumin), wherein the weight ratio of the albumin and the mTOR inhibitor in the composition is no greater than about 9:1 (such as about 9:1 or about 8:1). In some embodiments, the nanoparticle compositions described herein comprises nanoparticles comprising an mTOR inhibitor (such as a limus drug, for example sirolimus) stabilized by an albumin (such as human albumin or human serum albumin), wherein the nanoparticles have an average diameter of no greater than about 200 nm, wherein the weight ratio of the albumin and the mTOR inhibitor in the composition is no greater than about 9:1 (such as about 9:1 or about 8:1). In some embodiments, the nanoparticle compositions described herein comprises nanoparticles comprising an mTOR inhibitor (such as a limus drug, for example sirolimus) stabilized by an albumin (such as human albumin or human serum albumin), wherein the nanoparticles have an average diameter of no greater than about 150 nm, wherein the weight ratio of the albumin and the mTOR inhibitor in the composition is no greater than about 9:1 (such as about 9:1 or about 8:1). In some embodiments, the nanoparticle compositions described herein comprises nanoparticles comprising an mTOR inhibitor (such as a limus drug, for example sirolimus) stabilized by an albumin (such as human albumin or human serum albumin), wherein the nanoparticles have an average diameter of about 150 nm, wherein the weight ratio of the albumin and the mTOR inhibitor in the composition is no greater than about 9:1 (such as about 9:1 or about 8:1). In some embodiments, the nanoparticle compositions described herein comprises nanoparticles comprising sirolimus stabilized by human albumin (such as human serum albumin), wherein the nanoparticles have an average diameter of no greater than about 150 nm (for example about 100 nm), wherein the weight ratio of albumin and the sirolimus in the composition is about 9:1 or about 8:1.

In some embodiments, the nanoparticle composition comprises Nab-sirolimus. In some embodiments, the nanoparticle composition is Nab-sirolimus. Nab-sirolimus is a formulation of sirolimus stabilized by human albumin USP, which can be dispersed in directly injectable physiological solution. The weight ratio of human albumin and sirolimus is about 8:1 to about 9:1. When dispersed in a suitable aqueous medium such as 0.9% sodium chloride injection or 5% dextrose injection, Nab-sirolimus forms a stable colloidal suspension of sirolimus. The mean particle size of the nanoparticles in the colloidal suspension is about 100 nanometers. Since HSA is freely soluble in water, Nab-sirolimus can be reconstituted in a wide range of concentrations ranging from dilute (0.1 mg/ml sirolimus) to concentrated (20 mg/ml sirolimus), including for example about 2 mg/ml to about 8 mg/ml, or about 5 mg/ml.

Methods of making nanoparticle compositions are known in the art. For example, nanoparticles containing mTOR inhibitor (such as a limus drug, e.g., sirolimus) and carrier protein (e.g., an albumin such as human serum albumin or human albumin) can be prepared under conditions of high shear forces (e.g., sonication, high pressure homogenization, or the like). These methods are disclosed in, for example, U.S. Pat. Nos. 5,916,596; 6,506,405; 6,749,868, 6,537,579 and 7,820,788 and also in U.S. Pat. Pub. Nos. 2007/0082838, 2006/0263434 and PCT Application WO 08/137148.

Briefly, the mTOR inhibitor (such as a limus drug, e.g., sirolimus) is dissolved in an organic solvent, and the solution can be added to a carrier protein solution such as an albumin solution. The mixture is subjected to high pressure homogenization. The organic solvent can then be removed by evaporation. The dispersion obtained can be further lyophilized. Suitable organic solvent include, for example, ketones, esters, ethers, chlorinated solvents, and other solvents known in the art. For example, the organic solvent can be methylene chloride or chloroform/ethanol (for example with a ratio of 1:9, 1:8, 1:7, 1:6, 1:5, 1:4, 1:3, 1:2, 1:1, 2:1, 3:1, 4:1, 5:1, 6:1, 7:1, 8:1, or 9:1).

mTOR Inhibitor

The methods described herein in some embodiments comprise administration of nanoparticle compositions of mTOR inhibitors. "mTOR inhibitor" used herein refers to an inhibitor of mTOR. mTOR is a serine/threonine-specific protein kinase downstream of the phosphatidylinositol 3-kinase (PI3K)/Akt (protein kinase B) pathway, and a key regulator of cell survival, proliferation, stress, and metabolism. mTOR pathway dysregulation has been found in many human carcinomas, and mTOR inhibition produced substantial inhibitory effects on tumor progression.

The mammalian target of rapamycin (mTOR) (also known as mechanistic target of rapamycin or FK506 binding protein 12-rapamycin associated protein 1 (FRAP1)) is an atypical serine/threonine protein kinase that is present in two distinct complexes, mTOR Complex 1 (mTORC1) and mTOR Complex 2 (mTORC2). mTORC1 is composed of mTOR, regulatory-associated protein of mTOR (Raptor), mammalian lethal with SEC13 protein 8 (MLST8), PRAS40 and DEPTOR (Kim et al. (2002). Cell 110: 163-75; Fang et al. (2001). Science 294 (5548): 1942-5). mTORC1 integrates four major signal inputs: nutrients (such as amino acids and phosphatidic acid), growth factors (insulin), energy and stress (such as hypoxia and DNA damage). Amino acid availability is signaled to mTORC1 via a pathway involving the Rag and Ragulator (LAMTOR1-3) Growth factors and hormones (e.g. insulin) signal to mTORC1 via Akt, which inactivates TSC2 to prevent inhibition of mTORC1. Alternatively, low ATP levels lead to the AMPK-dependent activation of TSC2 and phosphorylation of raptor to reduce mTORC1 signaling proteins.

Active mTORC1 has a number of downstream biological effects including translation of mRNA via the phosphorylation of downstream targets (4E-BP1 and p70 S6 Kinase), suppression of autophagy (Atg13, ULK1), ribosome biogenesis, and activation of transcription leading to mitochondrial metabolism or adipogenesis. Accordingly, mTORC1 activity promotes either cellular growth when conditions are favorable or catabolic processes during stress or when conditions are unfavorable.

mTORC2 is composed of mTOR, rapamycin-insensitive companion of mTOR (RICTOR), GβL, and mammalian stress-activated protein kinase interacting protein 1 (mSIN1). In contrast to mTORC1, for which many upstream signals and cellular functions have been defined (see above), relatively little is known about mTORC2 biology. mTORC2 regulates cytoskeletal organization through its stimulation of F-actin stress fibers, paxillin, RhoA, Racl, Cdc42, and protein kinase C a (PKCa). It had been observed that knocking down mTORC2 components affects actin polymerization and perturbs cell morphology (Jacinto et al. (2004). Nat. Cell Biol. 6, 1122-1128; Sarbassov et al. (2004). Curr. Biol. 14, 1296-1302). This suggests that mTORC2 controls the actin cytoskeleton by promoting protein kinase Cα (PKCα) phosphorylation, phosphorylation of paxillin and its relocalization to focal adhesions, and the GTP loading of RhoA and Rac 1. The molecular mechanism by which mTORC2 regulates these processes has not been determined.

In some embodiments, the mTOR inhibitor is an inhibitor of mTORC1. In some embodiments, the mTOR inhibitor is an inhibitor of mTORC2.

In some embodiments, the mTOR inhibitor is a limus drug, which includes sirolimus and its analogues. Examples of limus drugs include, but are not limited to, temsirolimus (CCI-779), everolimus (RAD001), ridaforolimus (AP-23573), deforolimus (MK-8669), zotarolimus (ABT-578), pimecrolimus, and tacrolimus (FK-506). In some embodiments, the limus drug is selected from the group consisting of temsirolimus (CCI-779), everolimus (RAD001), ridaforolimus (AP-23573), deforolimus (MK-8669), zotarolimus (ABT-578), pimecrolimus, and tacrolimus (FK-506).

In some embodiments, the mTOR inhibitor is sirolimus. Sirolimus is macrolide antibiotic that complexes with FKBP-12 and inhibits the mTOR pathway by binding mTORC1.

In some embodiments, the mTOR inhibitor is selected from the group consisting of sirolimus (rapamycin), BEZ235 (NVP-BEZ235), everolimus (also known as RAD001 and sold under the trademarks Zortress®, Certican®, and Afinitor®), AZD8055, temsirolimus (also known as CCI-779 and sold under the trademark Torisel®), PI-103, Ku-0063794, INK 128, AZD2014, NVP-BGT226, PF-04691502, CH5132799, GDC-0980 (RG7422), Torin 1, WAY-600, WYE-125132, WYE-687, GSK2126458, PF-05212384 (PKI-587), PP-121, OSI-027, Palomid 529, PP242, XL765, GSK1059615, WYE-354, and eforolimus (also known as ridaforolimus or deforolimus).

BEZ235 (NVP-BEZ235) is an imidazoquilonine derivative that is an mTORC1 catalytic inhibitor (Roper J, et al. PLoS One. 2011, 6(9), e25132). Everolimus is the 40-O-(2-hydroxyethyl) derivative of rapamycin and binds the cyclophilin FKBP-12, and this complex also mTORC1. AZD8055 is a small molecule that inhibits the phosphorylation of mTORC1 (p70S6K and 4E-BP1). Temsirolimus is a small molecule that forms a complex with the FK506-binding protein and prohibits the activation of mTOR when it resides in the mTORC1 complex. PI-103 is a small molecule that inhibits the activation of the rapamycin-sensitive (mTORC1) complex (Knight et al. (2006) Cell. 125: 733-47). KU-0063794 is a small molecule that inhibits the phosphorylation of mTORC1 at Ser2448 in a dose-dependent and time-dependent manner. INK 128, AZD2014, NVP-BGT226, CH5132799, WYE-687, and are each small molecule inhibitors of mTORC1. PF-04691502 inhibits mTORC1 activity. GDC-0980 is an orally bioavailable small molecule that inhibits Class I PI3 Kinase and TORC1. Torin 1 is a potent small molecule inhibitor of mTOR. WAY-600 is a potent, ATP-competitive and selective inhibitor of mTOR. WYE-125132 is an ATP-competitive small molecule inhibitor of mTORC1. GSK2126458 is an inhibitor of mTORC1. PKI-587 is a highly potent dual inhibitor of PI3Kα, PI3Kγ and mTOR. PP-121 is a multi-target inhibitor of PDGFR, Hck, mTOR, VEGFR2, Src and Abl. OSI-027 is a selective and potent dual inhibitor of mTORC1 and mTORC2 with IC50 of 22 nM and 65 nM, respectively. Palomid 529 is a small molecule inhibitor of mTORC1 that lacks affinity for ABCB1/ABCG2 and has good brain penetration (Lin et al. (2013) Int J Cancer DOI: 10.1002/ijc.28126 (e-published ahead of print). PP242 is a selective mTOR inhibitor. XL765 is a dual inhibitor of mTOR/PI3k for mTOR, p110α, p110β, p110γ and p110δ. GSK1059615 is a novel and dual inhibitor of PI3Kα, PI3Kβ, PI3Kδ, PI3Kγ and mTOR. WYE-354 inhibits mTORC1 in HEK293 cells (0.2 μM-5 μM) and in HUVEC cells (10 nM-1 μM). WYE-354 is a potent, specific and ATP-competitive inhibitor of mTOR. Deforolimus (Ridaforolimus, AP23573, MK-8669) is a selective mTOR inhibitor.

Other Components in the Nanoparticle Compositions

The nanoparticles described herein can be present in a composition that include other agents, excipients, or stabilizers. For example, to increase stability by increasing the negative zeta potential of nanoparticles, certain negatively charged components may be added. Such negatively charged components include, but are not limited to bile salts of bile acids consisting of glycocholic acid, cholic acid, chenodeoxycholic acid, taurocholic acid, glycochenodeoxycholic acid, taurochenodeoxycholic acid, litocholic acid, ursodeoxycholic acid, dehydrocholic acid and others; phospholipids including lecithin (egg yolk) based phospholipids which include the following phosphatidylcholines: palmitoyloleoylphosphatidylcholine, palmitoyllinoleoylphosphatidylcholine, stearoyllinoleoylphosphatidylcholine stearoyloleoylphosphatidylcholine, stearoylarachidoylphosphatidylcholine, and dipalmitoylphosphatidylcholine. Other phospholipids including L-α-dimyristoylphosphatidylcholine (DMPC), dioleoylphosphatidylcholine (DOPC), distearyolphosphatidylcholine (DSPC), hydrogenated soy phosphatidylcholine (HSPC), and other related compounds. Negatively charged surfactants or emulsifiers are also suitable as additives, e.g., sodium cholesteryl sulfate and the like.

In some embodiments, the composition is suitable for administration to a human. In some embodiments, the composition is suitable for administration to a mammal such as, in the veterinary context, domestic pets and agricultural animals. There are a wide variety of suitable formulations of the nanoparticle composition (see, e.g., U.S. Pat. Nos. 5,916,596 and 6,096,331). The following formulations and methods are merely exemplary and are in no way limiting. Formulations suitable for oral administration can consist of (a) liquid solutions, such as an effective amount of the compound dissolved in diluents, such as water, saline, or orange juice, (b) capsules, sachets or tablets, each containing a predetermined amount of the active ingredient, as solids or granules, (c) suspensions in an appropriate liquid, and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

Examples of suitable carriers, excipients, and diluents include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline solution, syrup, methylcellulose, methyl- and propylhydroxybenzoates, talc, magnesium stearate, and mineral oil. The formulations can additionally include lubricating agents, wetting agents, emulsifying and suspending agents, preserving agents, sweetening agents or flavoring agents.

Formulations suitable for parenteral administration include aqueous and non-aqueous, isotonic sterile injection solutions, which can contain anti-oxidants, buffers, bacteriostats, and solutes that render the formulation compatible with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described. Injectable formulations are preferred.

In some embodiments, the composition is formulated to have a pH range of about 4.5 to about 9.0, including for example pH ranges of any of about 5.0 to about 8.0, about 6.5 to about 7.5, and about 6.5 to about 7.0. In some embodiments, the pH of the composition is formulated to no less than about 6, including for example no less than about any of 6.5, 7, or 8 (such as about 8). The composition can also be made to be isotonic with blood by the addition of a suitable tonicity modifier, such as glycerol.

Kits, Medicines, and Compositions

The invention also provides kits, medicines, compositions, and unit dosage forms for use in any of the methods described herein.

Kits of the invention include one or more containers comprising limus drug-containing nanoparticle compositions (or unit dosage forms and/or articles of manufacture) and/or another agent (such as the agents described herein), and in some embodiments, further comprise instructions for use in accordance with any of the methods described herein. The kit may further comprise a description of selection an individual suitable or treatment. Instructions supplied in the kits of the invention are typically written instructions on a label or package insert (e.g., a paper sheet included in the kit), but machine-readable instructions (e.g., instructions carried on a magnetic or optical storage disk) are also acceptable.

For example, in some embodiments, the kit comprises a) a composition comprising nanoparticles comprising mTOR inhibitor (such as a limus drug) and an albumin (such as human serum albumin), and b) instructions for administering the nanoparticle composition for treatment of bladder cancer. In some embodiments, the kit comprises a) a composition comprising nanoparticles comprising mTOR inhibitor (such as a limus drug) and an albumin (such as human serum albumin), b) an effective amount of another agent, wherein the other agent inhibits microtubule disassembly, and c) instructions for administering (such as administering intravesicularly or intravenously) the nanoparticle composition and the other agents for treatment of bladder cancer. The nanoparticles and the other agents can be present in separate containers or in a single container. For example, the kit may comprise one distinct composition or two or more compositions wherein one composition comprises nanoparticles and one composition comprises another agent.

The kits of the invention are in suitable packaging. Suitable packaging include, but is not limited to, vials, bottles, jars, flexible packaging (e.g., seled Mylar or plastic bags), and the like. Kits may optionally provide additional components such as buffers and interpretative information. The present application thus also provides articles of manufacture, which include vials (such as sealed vials), bottles, jars, flexible packaging, and the like.

The instructions relating to the use of the nanoparticle compositions generally include information as to dosage, dosing schedule, and route of administration for the intended treatment. The containers may be unit doses, bulk packages (e.g., multi-dose packages) or subunit doses. For example, kits may be provided that contain sufficient dosages of the mTOR inhibitor (such as a limus drug, e.g., sirolimus) as disclosed herein to provide effective treatment of an individual for an extended period, such as any of a week, 8 days, 9 days, 10 days, 11 days, 12 days, 13 days, 2 weeks, 3 weeks, 4 weeks, 6 weeks, 8 weeks, 3 months, 4 months, 5 months, 7 months, 8 months, 9 months, or more. Kits may also include multiple unit doses of the mTOR inhibitor (such as a limus drug) and pharmaceutical compositions and instructions for use and packaged in quantities sufficient for storage and use in pharmacies, for example, hospital pharmacies and compounding pharmacies.

Also provided are medicines, compositions, and unit dosage forms useful for the methods described herein. In some embodiments, there is provided a medicine (or composition) for use in treating bladder cancer, comprising nanoparticles comprising an mTOR inhibitor (such as a limus drug) and an albumin (such as human serum albumin). In some embodiments, there is provided a medicine (or composition or a unit dosage form) for use in treating bladder cancer in conjunction with another agent, comprising nanoparticles comprising a limus drug and an albumin (such as human serum albumin), wherein the other agent inhibits microtubule disassembly. In some embodiments, there is provided a medicine (or composition or a unit dosage form) for use in treating bladder cancer, comprising nanoparticles comprising a limus drug and an albumin (such as human serum albumin) and another agent, wherein the other agent inhibits microtubule disassembly.

Exemplary Embodiments

The present application in some embodiments provides a method of treating bladder cancer in an individual, comprising administering to the individual an effective amount of a composition comprising nanoparticles comprising a limus drug and an albumin.

In some embodiments according to (e.g., as applied to) the method above, the nanoparticle composition is administered intravesicularly.

In some embodiments according to (e.g., as applied to) any one of the methods above, the bladder cancer is non-muscle-invasive bladder cancer.

In some embodiments according to (e.g., as applied to) any one of the methods above, the bladder cancer is refractory to treatment with BCG, mitomycin C, or interferon.

In some embodiments according to (e.g., as applied to) any one of the methods above, the nanoparticle composition is administered at least once weekly.

In some embodiments according to (e.g., as applied to) any one of the methods above, the dose of limus drug in the nanoparticle composition is about 5 mg to about 500 mg (such as about 30 mg to about 400 mg).

In some embodiments according to (e.g., as applied to) any one of the methods above, the nanoparticle composition is administered at a volume of about 20 ml to about 150 ml.

In some embodiments according to (e.g., as applied to) any one of the methods above, the nanoparticle composition is administered intravesicularly, and wherein the composition is retained in the bladder for about 30 minutes to about 4 hours.

In some embodiments according to (e.g., as applied to) any one of the methods above, further comprising administering an effective amount of a second therapeutic agent.

In some embodiments according to (e.g., as applied to) any one of the methods above, the second therapeutic agent is an immununotherapeutic agent, such as BCG. In some embodiments, the BCG is administered intravesicularly, e.g., at the dose of about 8 mg to about 100 mg.

In some embodiments according to (e.g., as applied to) any one of the methods above, the method further comprises administering to the individual a therapeutic agent. In some embodiments, the therapeutic agent is selected from the group consisting of an alkylating agent, an anthracycline antibiotic, an antimetabolite, an indolequinone, a taxane, and a platinum-based agent. In some embodiments, the therapeutic agent is selected from the group consisting of mitomycin, epirubicin, doxorubicin, vairubicin, gemcitabine, apaziquone, docetaxel, paclitaxel, and cisplatin.

In some embodiments according to (e.g., as applied to) any one of the methods above, the limus drug is sirolimus.

In some embodiments according to (e.g., as applied to) any one of the methods above, the nanoparticles in the composition have an average diameter of no greater than about 200 nm.

In some embodiments according to (e.g., as applied to) any one of the methods above, the limus drug in the nanoparticles are coated with albumin.

In some embodiments according to (e.g., as applied to) any one of the methods above, the bladder cancer is urothelial carcinoma.

In some embodiments according to (e.g., as applied to) any one of the methods above, the bladder cancer is a high grade bladder cancer.

In some embodiments according to (e.g., as applied to) any one of the methods above, the individual is human.

In some embodiments according to (e.g., as applied to) any one of the methods above, the individual is selected for treatment based on the level of one of more of: p-S6K, pAKT, p-4EBP1, Ki67, p53, p63, Stathmin, Tau, SPARC, p73, c-myc, and cyclin D1.

In some embodiments according to (e.g., as applied to) any one of the methods above, further comprising determining the level of one of more of: p-S6K, pAKT, p-4EBP1, Ki67, p53, p63, Stathmin, Tau, SPARC, p73, c-myc, and cyclin D1 prior to treatment. In some embodiments, the method further comprises selecting the individual for treatment based on a high level of one or more of: p-S6K, pAKT, p-4EBP1, Ki67, p53, p63, Stathmin, Tau, SPARC, p73, c-myc, and cyclin D1.

In some embodiments according to (e.g., as applied to) any one of the methods above, further comprising determining the level of one of more of: p-S6K, pAKT, p-4EBP1, Ki67, p53, p63, Stathmin, Tau, SPARC, p'73, c-myc, and cyclin D1 after the treatment.

Those skilled in the art will recognize that several embodiments are possible within the scope and spirit of this invention. The invention will now be described in greater detail by reference to the following non-limiting examples. The following examples further illustrate the invention but, of course, should not be construed as in any way limiting its scope.

EXAMPLES

Example 1: Phase 1 Clinical Trial for Establishing the Maximum Delivered Dose (MDD) and Safety of Nab-sirolimus (mTOR Inhibitor) for Intravesicular Treatment of BCG-Refractory Non-Muscle Invasive Bladder Cancer (NMIBC)

Patients with BCG-refractory NMIBC receive Nab-sirolimus intravesicularly by sterile urethral catheterization following resection of visible tumors during cystoscopy. This study enrolls 15 patients, 3 per cohort: 100 mg/week, 100 mg 2×/week (total weekly dose 200 mg), 300 mg/week, 200 mg 2×/week (total weekly dose 400 mg), and 400 mg/week for 6 weeks of treatment. For each treatment, nab-sirolimus is reconstituted with 100 ml 0.9% sodium chloride. Patients are instructed to keep the drug in the bladder for 2 hours before voiding. If a National Cancer Institute Common Toxicity Criteria (NCI CTC) v3.0 grade 2 local toxicity develops, treatment is delayed for 1 dose and resume if the toxicity resolves to grade 1 or less. A DLT (dose limiting toxicity) is considered any grade 3 or 4 event, and the patient is immediately removed from the trial. Dose escalation follows the 3+3 rule to establish the MDD. Six weeks after the last treatment, patients undergo a cystoscopy and biopsy. A complete response (CR) is defined as a cancer-negative biopsy at the 6-week post-treatment.

If a patient has a CR, the patient receives additional monthly maintenance instillations at the maximum dose that particular patient received. Cystoscopic examinations are every 3 months, and the patient will receive therapy until disease progression for a maximum of 6 additional instillations.

Systemic and local bladder toxicities are monitored throughout treatment and maintenance therapy.

Collection and Processing of Samples: Physical exams and collection of urine and blood samples are performed at enrollment, treatment days, end of treatment, and 6-week follow up. Biopsies of tumor and normal bladder tissue are taken pretreatment, once during treatment prior to day 14 dosing, and at the 6-week post-treatment cystoscopy.

Analysis: At each visit, patients are monitored for local bladder toxicity as defined by the NCI CTC v3.0. At every visit, patients' vitals (weight, blood pressure, and pulse) and updated medical history are obtained. Urine samples are checked by dipstick for pH and sent to the laboratory for analysis. Four hours after the nab-sirolimus treatment, blood samples are taken for analysis of serum sirolimus levels. Complete blood count, basic metabolic panel, hepatic functional panel, lipid panel, and coagulation profile are checked for signs of systemic toxicity.

Example 2: Efficacy of the Combination of Intravesicular Nab-sirolimus and BCG in a Genetically Engineered Mouse Model of Bladder Cancer This preclinical study uses an animal model of progressive bladder cancer. These genetically engineered mice have a targeted deletion of p53 and PTEN in the bladder epithelium. This combined deletion of p53 and PTEN in the bladder epithelium after the delivery of Adeno-Cre results in CIS development at ~6 weeks after injection, resembling the human disease. Thus, we initiate treatment at 6 weeks after Adeno-Cre injection. We use only female mice in our study as an angiocatheter can be easily passed through the urethra compared to male mice whose urethras are more convoluted.

Surgery: After adequate sedation is achieved with inhalational anesthesia, a lubricated angiocatheter (24G) is passed through the urethra. The bladder is irrigated with sterile PBS to ensure return of urine and thus, proper positioning in the bladder. Urine will be removed and discarded. Treatment will be delivered via the angiocatheter and into the bladder. Silk suture (5-0) is secured around the urethra to prevent intravesicular treatment from being expelled. Suture remains in place be until a treatment time of 2 hours is achieved.

Doses: A preliminary in vitro study determines if Nab-sirolimus has any effect on BCG viability. A pilot study is performed to determine tolerable dosage of single agents and combination therapy. We start with a BCG dose of $2 \times 10^6$ CFU/ml based on the clinically used dose ($1-8 \times 10^6$ CFU/ml), and the dose used in a previous preclinical study with BCG-based combination therapy. For Nab-sirolimus, we start with an initial intravesicular dose of 15 mg/kg. After the conclusion of the pilot study, we establish the specific study dose in mice (n=15/group). Treatment duration is 6 weeks. The single agent cohort undergoes once weekly treatments of either BCG or nab-sirolimus, with a total indwell time of 2 hours. The combination cohort receives BCG on Monday, then Nab-sirolimus on Thursday. A control group receives vehicle once weekly. Biweekly weights are utilized to assess drug toxicity. Mice with body weight loss of 10-15% or sick appearance is euthanized for humane reasons. As an endpoint, if the tumor is greater than 1.5 cm, the mice is euthanized.

Collection and Processing of Samples: Periodic ultrasonography will be performed prior to treatment and every 2 weeks thereafter to monitor presence of tumor and tumor size. Throughout the course of the preclinical trial, we observe the mice for any physical signs of distress or loss of body weight (10-15%), which could indicate toxicity or infection.

Analysis: All surviving mice are sacrificed after 6 weeks of intravesicular treatment for evaluation of bladder size, weight, and immunohistochemistry (IHC) analysis. IHC analysis includes hematoxylin and eosin (H&E) staining, markers of the mTOR pathway (pS6, p-AKT, p-4EBP1), and markers of immune cells (to identify macrophages, dendritic cells, T-cells, etc).

Example 3: Evaluation of the Systemic and Target Tissue Drug Exposure of Intravesicular Nab-sirolimus in Patients with NMIBC During phase 1/2 clinical trials, blood samples are taken 4 hours after nab-sirolimus administration, collected in EDTA-treated tubes, and stored at −80° C. until analysis. The bladder tissue biopsy samples for measuring sirolimus levels (5 samples per patient) are taken via cystoscopy just prior to dosing on day 14. The tissue samples are collected into 15 ml cryovials, flash frozen on dry ice, and stored at −80° C. until analysis.

Analysis: Sirolimus levels in serum and in bladder tissue samples are measured by liquid chromatography/mass spectrometry (LC/NIS). Sirolimus concentrations in the target bladder tissue are correlated with clinical efficacy data, and pharmacodynamic biomarkers to help establish effective biological dose.

Example 4: Evaluation of Target Biomarker Suppression and Other Relevant Molecular Markers in Patient Tissue Samples We evaluate the activated mTOR levels at baseline and at 6-week post-treatment, which help to determine the clinical value for pretreatment screening of patient population. Demonstration of mTOR pathway suppression following treatment can provide clear indication of the specificity and efficacy of nab-sirolimus and potentially predict clinical response. Several biomarkers are particular relevant to the mTOR pathway (p-S6K, p-AKT, p-4EBP1), and bladder cancer (Ki67) and will be examined. P-S6 is a biomarker of mTOR pathway activation, which is expected to be reduced when mTOR activity is inhibited. Ki67 is a cellular marker for proliferation and is elevated in bladder cancer. Following inhibition of mTORC1 by sirolimus and its analogues, the p-Akt is increased through feedback activation with mTORC2, which may result in side effects and resistance of sirolimus treatment. Other potential molecular markers would include p53, p63, Stathmin, Tau, Ki67, and SPARC.

Collection and Processing of Samples: Prior to treatment, tumor and normal tissues samples are collected by resection of visible tumors during cystoscopy. Additional normal tissue samples (and tumor samples if available) are collected prior to the 14-day treatment and at 6-weeks post-treatment cystoscopy. The samples are immediately frozen and sectioned.

Analysis: The samples are analyzed by immunohistochemistry (H&E staining, and with antibodies against p-S6K, p-AKT, p-4EBP1, etc). The slides are scored by a pathologist for staining intensity of different biomarkers. Quantification of proliferating cells are done as described previously. The biomarker status at baseline and during treatment are correlated with clinical responses with Fisher's exact test to investigate the predictive value of these biomarkers for NMIBC patients treated with intravesicular Nab-sirolimus therapy.

Example 5: Phase 2 Clinical Study to Evaluate the Efficacy, Safety, and Potential Predictive Biomarkers of Intravesicular Nab-sirolimus in BCG-Refractory NMIBC Research Design: The clinical phase 1 dose escalation study is expanded into this clinical phase 2 study with up to 29 patients enrolled at the MDD to evaluate the utility of nab-sirolimus in the treatment of BCG-refractory NMIBC as measured by rate of complete responders. We enroll 10 patients in the first stage (Simon 2-stage method). If 2 or more patients respond, we enroll an additional 19 in the second stage. If only 1 or no response is observed in the first stage, we terminate the study for lack of efficacy. Based on our operating characteristic of 5% type I error and 20% type II error, the number of patients that is expected to be enrolled will be 15 on average with a maximum total of 29 in order to sufficiently power the study. Patient treatment protocol is the same as the phase 1 study. If a patient has a CR, the patient receive additional monthly maintenance instillations at the MDD. Cystoscopic examinations will be performed every 3 months, and the patient continue therapy until disease progression or for a maximum 6 additional instillations. Patients are monitored for local and systemic toxicities throughout the study and maintenance therapy.

Collection and Processing of Samples: Patient tumor and normal bladder tissue samples are taken prior to, during, and after treatment. Blood and urine samples will also be taken at multiple time points as described preciously.

Analysis: Patient samples are evaluated following procedures described above. A CR is defined as a cancer-negative biopsy at the 6-week post-treatment cystoscopy. Safety assessment is per standard NCI criteria.

Example 6: Phase 2 Clinical Study to Evaluate the Efficacy, Safety, and Potential Predictive Biomarkers of Intravesicular Nab-sirolimus Plus BCG in BCG-Refractory NMIBC Research Design: BCG is dosed at the clinically used weekly intravesicular dose of 81 mg BCG in 50 ml saline. BCG can also be used at half or one third of the standard 81 mg dose. With the established MDD of Nab-sirolimus, up to 20 patients are treated with a combination of intravesicular nab-sirolimus plus BCG. Patient enrollment and statistical considerations are similar to the study above, with 2 stages of enrollment. Scheduling of the combination treatment (drugs given together or sequentially) are determined from Example 2.

Collection and Processing of Samples: Patient tumor and bladder tissue samples are taken prior to, during, and after treatment. Blood and urine samples (for cytokine levels as indicators of local immune response) are also taken at multiple time points.

Analysis: Patient samples are evaluated following procedures listed above. Patients are evaluated for efficacy by cystoscopy and biopsy 6 weeks post-treatment. A CR is defined as a cancer-negative biopsy at the 6-week post-treatment cystoscopy.

Example 7: Phase 2 Clinical Study to Evaluate the Efficacy and Safety of Intravesicular Nab-sirolimus and Mitomycin C Combination in BCG-Refractory NMIBC Design: Appropriate dose of nab-sirolimus is reconstituted in 80-100 mL saline and administered through intravesicular catheters for a weekly 1-2 hour treatment of 6 weeks. Mitomycin C is dosed intravesicularly at 40 mg in 40 mL of sterile water for injection, once weekly for 6 weeks. Up to 20 patients are treated with a combination of intravesicular nab-sirolimus and mitomycin C. Scheduling of the combination treatment is determined from outcomes of Aims 1 and 3. The drugs are given sequentially on the same day, each with 2 hours retention in the bladder. If a patient has a CR, the patient receives additional monthly maintenance instillations of Nab-sirolimus and mitomycin C. Cystoscopic examinations are performed every 3 months, and the patient continue therapy until disease progression or for a maximum 6 additional instillations. Patients are monitored for local and systemic toxicities throughout the study and maintenance therapy Collection and Processing of Samples: Physical exams and collection of urine and blood samples are performed at enrollment, treatment days, end of treatment, and 6-week follow up. Biopsies of tumor and normal bladder tissue will be taken by cystoscopy pretreatment, once during treatment prior to day 14 dosing, and at the 6-week post-treatment.

Analysis: Patient samples are evaluated following procedures above. Patients will be evaluated for efficacy by cystoscopy and biopsy 6 weeks post-treatment.

Example 8: Efficacy of the Combination of Nab-sirolimus and Various Agents in a Xenograft Model (T24) of Bladder Cancer T24 human bladder cancer cells are cultured at 37° C. and 5% CO2 in RPMI 1640 supplemented with 10% FBS, 100 U/mL penicillin and 100 µg/mL streptomycin, 800 mg/L NaHCO3 and 3.6 g HEPES. Male NCr nu/nu nude mice will be used. The study will require 100 mice, 5 to 6 weeks old. Animal weight will be 20-30 grams on the day of implantation. Animals are identified by cage number and ear punch. Approximately one hundred mice are used for the study once the average tumor volumes reach approximately 100 mm$^3$. The mice will be randomly assigned to 10 study groups with 10 animals in each group prior to dosing. The study groups and treatment schedules are listed in the Table below.

| Group | Treatment (N = 10) | Dosing Schedule |
| --- | --- | --- |
| A | Saline | weekly for 3 weeks, IV |
| B | nab-sirolimus (nab-S) | 40 mg/kg, weekly for 3 weeks, IV |
| C | Mitomycin C (MMC) | 1 mg/kg, weekly for 3 weeks, IP |
| D | Cisplatin (Cis) | 3 mg/kg, weekly for 3 weeks, IP |
| E | Gemcitabine (Gem) | 50 mg/kg, weekly for 3 weeks, IP |
| F | Valrubicin (Val) | 30 mg/kg, weekly for 3 weeks, IP |
| G | MMC + nab-S | Mitomycin C administered immediately prior to nab-S |
| H | Cis + nab-S | Cisplatin administered immediately prior to nab-S |
| I | Gem + nab-S | Gemcitabine administered immediately prior to nab-S |
| J | Val + nab-S | Valrubicin administered immediately prior to nab-S |

To compare the antitumor activity of the combination treatment versus single agents, 10 treatment groups with mice bearing T24 human bladder cancer xenografts are used, including saline control, nab-sirolimus, mitomycin C, cisplatin, gemcitabine, valrubicin, and the combination treatment groups of mitomycin C, cisplatin, gemcitabine, or valrubicin each in combination with nab-sirolimus. The mice are treated for 4 weeks, and the tumors are measured with a digital caliper twice weekly until the end of study. Animal body weights are measured twice weekly, and animals are monitored for any physical signs of distress or significant loss of body weight (10-15%).

Analysis: Tumor size data are analyzed for tumor growth inhibition by each treatment regimen. Statistical analysis of tumor growth curves are performed using ANOVA.

Example 9: Phase 2 Clinical Study to Evaluate the Efficacy and Safety of Intravesicular Nab-sirolimus and Gemcitabine Combination in BCG-Refractory NMIBC Design: Appropriate dose of nab-sirolimus is reconstituted in 100 mL saline and administered through intravesicular catheters for a treatment of 6 weeks. Gemcitabine is dosed intravesically at a dose of 2 g in approx 50 ml once weekly for 6 weeks for 1-2 hours. Up to 20 patients are treated with a combination of intravesicular nab-sirolimus and mitomycin C. The drugs are given sequentially on the same day, each with 2 hours retention in the bladder. If a patient has a CR, the patient receives additional monthly maintenance instillations of Nab-sirolimus and mitomycin C. Cystoscopic examinations are performed every 3 months, and the patient continues therapy until disease progression or for a maximum 6 additional instillations. Patients are monitored for local and systemic toxicities throughout the study and maintenance therapy Collection and Processing of Samples: Physical exams and collection of urine and blood samples are performed at enrollment, treatment days, end of treatment, and 6-week follow up. Biopsies of tumor and normal bladder tissue will be taken by cystoscopy pretreatment, once during treatment prior to day 14 dosing, and at the 6-week post-treatment.

Analysis: Patient samples are evaluated following procedures above. Patients will be evaluated for efficacy by cystoscopy and biopsy 6 weeks post-treatment.

What is claimed is:

1. A method of treating bladder cancer in an individual, comprising administering to the individual a) an effective amount of a composition comprising nanoparticles comprising rapamycin and an albumin and b) an effective amount of Bacillus Calmette-Guérin (BCG), wherein the nanoparticle composition is administered intravesicularly.

2. The method of claim 1, wherein the bladder cancer is non-muscle-invasive bladder cancer.

3. The method of claim 1, wherein the bladder cancer is refractory to treatment with BCG, mitomycin C, or interferon.

4. The method of claim 1, wherein the nanoparticle composition is administered at least once weekly.

5. The method of claim 1, wherein the dose of rapamycin in the nanoparticle composition is about 5 mg to about 500 mg.

6. The method of claim 5, wherein the dose of rapamycin in the nanoparticle composition is about 30 mg to about 400 mg.

7. The method of claim 5, wherein the nanoparticle composition is administered at a volume of about 20 ml to about 150 ml.

8. The method of claim 5, wherein the nanoparticle composition is retained in the bladder for about 30 minutes to about 4 hours.

9. The method of claim 1, wherein the BCG is administered intravesicularly.

10. The method of claim 9, wherein the BCG is administered at the dose of about 8 mg to about 100 mg.

11. The method of claim 1, wherein the nanoparticles in the composition have an average diameter of no greater than about 200 nm.

12. The method of claim 1, wherein the nanoparticles comprise rapamycin coated with albumin.

13. The method of claim 1, wherein the bladder cancer is urothelial carcinoma.

14. The method of claim 1, wherein the bladder cancer is a high grade bladder cancer.

15. The method of claim 1, wherein the individual is human.

16. The method of claim 1, wherein the individual is selected for treatment based on the level of one of more of: p-S6K, pAKT, p-4EBP1, Ki67, p53, p63, Stathmin, Tau, SPARC, p73, c-myc, and cyclin D1.

17. The method of claim 16, further comprising determining the level of one of more of: p-S6K, pAKT, p-4EBP1, Ki67, p53, p63, Stathmin, Tau, SPARC, p73, c-myc, and cyclin D1 prior to treatment.

18. The method of claim 16, further comprising selecting the individual for treatment based on a high level of one or more of: p-S6K, pAKT, p-4EBP1, Ki67, p53, p63, Stathmin, Tau, SPARC, p73, c-myc, and cyclin D1.

19. The method of claim 1, further comprising determining the level of one of more of: p-S6K, pAKT, p-4EBP1, Ki67, p53, p63, Stathmin, Tau, SPARC, p73, c-myc, and cyclin D1 after the treatment.

* * * * *

UNITED STATES PATENT AND TRADEMARK OFFICE
CERTIFICATE OF CORRECTION

PATENT NO. : 10,413,531 B2
APPLICATION NO. : 15/938952
DATED : September 17, 2019
INVENTOR(S) : Neil P. Desai It is certified that error appears in the above-identified patent and that said Letters Patent is hereby corrected as shown below:

On the Title Page

On page 3, Column 1, under OTHER PUBLICATIONS, Line 39, please replace "Cystalloids" with -- Crystalloids --;

On page 4, Column 1, under OTHER PUBLICATIONS, Line 9, please replace "Glcoprotein,"" with -- Glycoprotein," --;

On page 4, Column 2, under OTHER PUBLICATIONS, Line 13, please replace ""Recommandations" with -- "Recommendations --;

In the Specification

On Column 3, Line 47, please replace "(BCG)" with -- (BCG)) --;

On Column 3, Line 48, please replace "ECG-" with -- BCG- --;

On Column 5, Line 40, please replace "Magentic" with -- Magnetic --;

On Column 7, Line 32, please replace "(PBK)/Akt" with -- (PI3K)/Akt --;

On Column 7, Line 48, please replace "eforolimus" with -- everolimus --;

On Column 8, Line 61, please replace "NFL" with -- NF1. --;

On Column 9, Line 37, please replace "chromosome ip." with -- chromosome 1p. --;

On Column 21, Line 55, please replace "immnunotherapeutic" with -- immunotherapeutic --;

On Column 28, Line 36, please replace "vairubicin," with -- valrubicin, --;

Signed and Sealed this
Tenth Day of August, 2021

Drew Hirshfeld
*Performing the Functions and Duties of the
Under Secretary of Commerce for Intellectual Property and
Director of the United States Patent and Trademark Office*

On Column 31, Line 37, please replace "20-ml" with -- 20 ml --;

On Column 32, Line 45, please replace "doxirubicin)." with -- doxorubicin). --;

On Column 39, Line 24, please replace "p'73," with -- p73, --;

On Column 41, Line 65, please replace "limns" with -- limus --;

On Column 43, Line 33, please replace "lupus" with -- limus --;

On Column 53, Line 12, please replace "intra-arteri al," with -- intra-arterial, --;

On Column 57, Line 35, please replace "WO 08/137148," with -- WO08/137148, --;

On Column 59, Lines 28-29, please replace "hypovolumic" with -- hypovolemic --;

On Column 65, Lines 15-16, please replace "WO 08/137148." with -- WO08/137148. --;

On Column 66, Line 11, please replace "Racl," with -- Rac1, --;

On Column 66, Line 12, please replace "C a (PKCa)." with -- C α (PKCα). --;

On Column 66, Line 20, please replace "Rac 1." with -- Rac1. --;

On Column 66, Line 50, please replace "eforolimus" with -- everolimus --;

On Column 66, Line 52, please replace "imidazoquilonine" with -- imidazoquinoline --;

On Column 67, Line 34, please replace "litocholic" with -- lithocholic --;

On Column 67, Line 44, please replace "distearyolphosphatidylcholine" with -- distearoylphosphatidylcholine --;

On Column 69, Line 14, please replace "seled" with -- sealed --;

On Column 70, Line 24, please replace "immununotherapeutic" with -- immunotherapeutic --;

On Column 70, Line 35, please replace "vairubicin," with -- valrubicin, --;

On Column 71, Line 4, please replace "p'73," with -- p73, --;

On Column 73, Line 7, please replace "(LC/NIS)." with -- (LC/MS). --;

In the Claims

On Column 76, Claim number 16, Line 65, please replace "one of" with -- one or --;

CERTIFICATE OF CORRECTION (continued)
U.S. Pat. No. 10,413,531 B2

On Column 77, Claim number 17, Line 2, please replace "one of" with -- one or --; and On Column 77, Claim number 19, Line 10, please replace "one of" with -- one or --.